US007767880B2

(12) United States Patent
McGrath et al.

(10) Patent No.: US 7,767,880 B2
(45) Date of Patent: Aug. 3, 2010

(54) METHODS OF SCREENING AGENTS FOR ACTIVITY USING TELEOSTS

(75) Inventors: Patricia McGrath, Cambridge, MA (US); Chuenlei Parng, Lexington, MA (US); George N. Serbedzija, Sudbury, MA (US)

(73) Assignee: Phylonix Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/927,473

(22) Filed: Oct. 29, 2007

(65) Prior Publication Data

US 2008/0152591 A1 Jun. 26, 2008

Related U.S. Application Data

(63) Continuation of application No. 11/515,355, filed on Sep. 1, 2006.

(51) Int. Cl.
*A61K 49/00* (2006.01)
*G01N 33/00* (2006.01)
*A01K 67/00* (2006.01)
*A01K 67/033* (2006.01)
*A01K 67/027* (2006.01)

(52) U.S. Cl. .............................. 800/13; 800/3; 800/20; 424/9.2

(58) Field of Classification Search ...................... 800/3, 800/14, 20
See application file for complete search history.

(56) References Cited

U.S. PATENT DOCUMENTS

| | | | |
|---|---|---|---|
| 4,220,858 A | 9/1980 | Ikeguchi et al. |
| 4,286,983 A | 9/1981 | Van Gilse et al. |
| 4,329,424 A | 5/1982 | Machlowitz et al. |
| 4,816,392 A | 3/1989 | Hokama |
| 4,964,615 A | 10/1990 | Mueller et al. |
| 5,326,692 A | 7/1994 | Brinkley et al. |
| 5,424,209 A | 6/1995 | Kearney |
| 5,491,084 A | 2/1996 | Chalfie et al. |
| 5,506,208 A | 4/1996 | Eyal et al. |
| 5,510,099 A | 4/1996 | Short et al. |
| 5,565,187 A | 10/1996 | Zikria et al. |
| 5,573,909 A | 11/1996 | Singer et al. |
| 5,593,678 A | 1/1997 | Evans et al. |
| 5,658,751 A | 8/1997 | Yue et al. |
| 5,672,470 A | 9/1997 | Hengstenberg et al. |
| 5,681,703 A | 10/1997 | Tomei |
| 5,712,395 A | 1/1998 | App et al. |
| 5,744,499 A | 4/1998 | Quash et al. |
| 5,830,730 A | 11/1998 | German et al. |
| 5,932,418 A | 8/1999 | Yager |
| 6,299,858 B1 | 10/2001 | Serbedzija et al. |
| 6,380,458 B1 | 4/2002 | Lin |
| 6,656,449 B1 | 12/2003 | Serbedzija et al. |
| 6,867,349 B2 | 3/2005 | Ekker et al. |
| 7,041,276 B2 | 5/2006 | Serbedzija et al. |
| 2004/0062712 A1 | 4/2004 | Serbedzija et al. |
| 2004/0133114 A1 | 7/2004 | Macrae et al. |
| 2005/0155087 A1 | 7/2005 | Zon et al. |
| 2005/0188426 A1 | 8/2005 | Serbedzija et al. |
| 2006/0104905 A1 | 5/2006 | Serbedzija et al. |
| 2006/0123487 A1 | 6/2006 | Serbedzija et al. |
| 2006/0193776 A1 | 8/2006 | Goldsmith et al. |
| 2007/0143865 A1 | 6/2007 | McGrath et al. |

FOREIGN PATENT DOCUMENTS

| | | |
|---|---|---|
| AU | 749688 | 10/2002 |
| DE | 4113393 A1 | 10/1992 |
| EP | 1 066 402 B1 | 5/2005 |
| EP | 1 644 733 B1 | 4/2007 |
| GB | 2080948 A | 2/1982 |
| WO | WO 95/11989 A1 | 5/1995 |
| WO | WO 96/03034 A1 | 2/1996 |
| WO | WO 98/31787 A1 | 7/1998 |
| WO | WO 99/42606 A1 | 8/1999 |
| WO | WO 01/92874 A1 | 12/2001 |
| WO | WO 03/052106 A1 | 6/2003 |
| WO | WO 2004/047634 A1 | 6/2004 |
| WO | WO 2005/080974 A1 | 9/2005 |
| WO | WO 2008/028162 A2 | 3/2008 |

OTHER PUBLICATIONS

Lieberoth, B et al, Double labelin of neurons by retrograde axonal tracing and non-radioactive in situ hybridization in the CNS of adult zebrafish, Methods in Cell Science, 2003, 25:65-70.*
Baraban et al., "Pentylenetetrazole Induced Changes in Zebrafish Behavior, Neural Activity and C-FOS Expression", *Neuroscience*, 131:759-768 (2005).
Seng et al., "Use of a monoclonal antibody specific for activated endothelial cells to quantitate angiogenesis in vivo in zebrafish after drug treatment," *Angiogenesis*, 7: 243-253, (2004).
Non-Final Office Action mailed May 6, 2008 for U.S. Appl. No. 11/320,251.
Notice of Allowance mailed May 8, 2008 for U.S. Appl. No. 11/114,712.
Notice of Allowance mailed Jun. 6, 2008 for U.S. Appl. No. 11/280,849.
Notice of Allowance mailed Sep. 9, 2008 for U.S. Appl. No. 11/114,712.
Final Office Action mailed Nov. 4, 2008 for U.S. Appl. No. 10/678,765.
U.S. Appl. No. 60/075,783, filed Feb. 23, 1998, Serbedzija.
U.S. Appl. No. 60/100,950, filed Sep. 18, 1998, Serbedzija.
U.S. Appl. No. 11/927,473, filed Oct. 29, 2007, McGrath.

(Continued)

*Primary Examiner*—Valarie Bertoglio
(74) *Attorney, Agent, or Firm*—Townsend and Townsend and Crew LLP

(57) ABSTRACT

The present invention provides methods of screening an agent for activity using teleosts. Methods of screening an agent for angiogenesis activity, toxic activity and an effect cell death activity in teleosts are provided. Methods of screening an agent for an activity in the brain or central nervous system in zebrafish are provided. The invention further provides high throughput methods of screening agents in multi-well plates.

18 Claims, 21 Drawing Sheets

OTHER PUBLICATIONS

Akimenko et al., "Rapid Communication: Anterior Duplication of the Sonic Hedgehog Expression Pattern in the Pectoral Fin Buds of Zebrafish Treated with Retinoic Acid,"*Dev. Biol*, 170:243-247 (1995).

Alexandre et al., "Somatotopy of the lateral line projection in larval zebrafish," *PNAS*, 96:7558-7562 (1999).

Amsterdam et al., "Requirements for green fluorescent proteing detection in transgnic zebrafish embryos" *Gene* 17: 99-103 (1996).

Anichtchik et al., "Neurochemical and behavioural changes in zebrafish *Danio rerio* after systemic administration of 6-hydroxydopamine and 1-methyl-4-phenyl-1,2,3,6-tetrahydropyridine," *Journal of Neurochemistry*, 88:443-453 (2004).

Ankley et al., "Small Fish Models for Identifying and Assessing the Effects of Endocrine-disrupting Chemicals," *ILAR Journal*, 45(4):469-483 (2004).

Armant et al., "Exposure of Embryonic Cells to Alcohol: Contrasting Effects During Preimplantation and Postimplantation Development", *Seminars in Perinatology*, 20(2): 127-139 (Apr. 1996).

Bakkers, et al ., "An important development role for oligosaccharides during early embryogenesis of cyprinid fish", *Pro. Natl. Acad. Sci. USA*, 94: 7982-7983 (Jul. 1997).

Baumann et al.,"Bipartite Axiation Follows Incomplete Epiboly in Zebrafish Embryos Treated with Chemical Teratogens", The Journal of Experimental Zoology, 230: 363-376 (1984).

Bechter et al., "Teratogenicity of arotinoids (retinoids): comparision of the who embryo culture system with the in vivo mouse model and the limb bud cell culture assay", *Teratol*, 44: 29A (1991).

Becker et al., "Teratogenic Actions of Ethanol in the Mouse: A Minireview", *Pharmacol. Biochem. Behav.* 55 (4) 501-513 (1996).

Behra et al., "The Use of Zebrafish Mutants to Identify Secondary Target Effects of Acetylcholine Esterase Inhibitors," *Toxicological Sciences*, 77:325-333 (2004).

Bernstein et al, "The Blood-Brain Barrier of Fish," *Experimental Neurolooy*, 11:464-473 (1965).

Birge et al., "Acetaminophen Hepatotoxicity: Correspondence of Selectiove Protein Arylation in Human and Mouse Liver in Vitro, in Culture, and in Vivo", *Toxicol. Applied Pharmacol.*, 105: 472-482 (1990).

Black, "Carcinogenicity tests with rainbow trout embryos: a review," *Aquatic Toxicology*, 11:129-142 (1988).

Boehm, et al., "Antiangoigenic therapy of experimental cancer does not induce acquired drug resistance", *Nature*, 390: 404-407 (1997).

Bonn, "Blocking angiogensis in diabetic reinopathy", Lancet, 348: 604 (1996).

Brier et al., "Angiogenises in Embryos and Ischemic Diseases", Thromb. Haemost., 78:(1): 678-683 (1997).

Bresch, "Early Life-Stage Test in Sebrafish versus a Growth Test in Rainbow Trout to Evaluate Toxic Effect", *Bull. Environ, Contam Toxicol.*, 46:641-648 (1991).

Bretaud et al., "Sensitivity of zebrafish to environmental toxins implicated in Parkinson's disease," *Neurotoxicology and Teratology*, 26:857-864 (2004).

Brustein et al , ""In vivo" monitoring of neuronal network activity in zebrafish by two-photon $Ca^{2+}$ imaging," *Eur J Physiol*, 446:766-773 (2003).

Buchmann et al., "Immunohistochemical Localization of the Cytochrom P450 Isozymes LMC3 and LM4B (P4501A1) in 2,3,7,8-Tetrachlorodibenzo-*p*-dioxin Treated Zebrafish (*brachyan rerio*)", *Toxicol. Appl Parmacol*. 123: 160-169 (1993).

Chang et a l., "Developmental Toxicity of Arecolin, the Major Alkaloid in Betel Nuts, in Zebrafish Embryos," *Birth Defects Research*, (Part A) 70:28-36 (2004).

Chen et al., "Mutations affecting the cardiovascular system and other internal organs in zebrafish", Development, 123: 293-302 (1996).

Chatot et al., "Successful Culture of Rat Embryos on Human Serum: Use in the Detection of Teratogens", *Science* 207: 1471-1473 (1980).

Chow et al., "The nuclear receptor transcription factor, retinoid-related orphan receptor β, regulate retinal progenotor proliferation", Mech. Dev., 77 (2):149-164 (1998).

Cicurel et al., "Post-implanation embryo culture: validation with selected compounds for teratogenicity testing", Xenobiotica, 18(6): 617-624 (1998).

Clarke "Development cell death: morphological diversity and multiple mechanisms", Anat. Embryol., 181:195-213 (1990).

Colloidi et al., "Induction of Zebrafish (*Brachydanio rerio*) P450 in vivo and in cell culture", *Xenobiotica*, 24(6): 487-493 (1994).

Couffinhal et al., Animal Model, Mouse Model of Angiogensis, Am. J. Pathol., 152 (6): 1667-1679 (Jun. 1998).

Cserr et al., "Blood-brain interfaces in vertebrates: a comparative approach," *Am J Physiol*, 246:R277-R288 (1984).

Currie, "Zebrafish genetics: Mutant cornucopia, " *Current Biology*, 6(12): 1548-1552 (1996).

Darland et al., "Behavioral screening for cocaine sensitivity in mutagenized zebrafish," *PNAS*, 98(20):11691-11696 (2001).

Dawson, "Additive Incidence of Development of Malformation for Xenopus Embryos Exposed to a Mixture of Ten Aliphatic Carboxylic Acids", Teratology, 44:531-546 (1991).

Debus et al., "Nematode Test to Estimate the hazard Potential of Solved Contaminations", Chemosphere, 29(3) 611-621(1994).

Den Hertog, Jeroen, "Chemical Genetics: Drug Screens in Zebrafish," *Bioscience Reports*, 25(5/6):289-297 (2005).

Dong et al., "Role of Aryl Hydrocarbon Receptor in Mesencephalic Circulation Failure and Apoptosis in Zebrafish Embryos Exposed to 2,3,7,8-Tetrachlorodibenzo-p-Dioxin," *Toxicological Sciences*, 77:109-116 (2004).

Dong et al., "2,3,7,8-Tetrachlorodibenzo-p-dioxin Toxicity in the Zebrafish Embryo: Local Circulation Failure in the Dorsal midbrain is Associated with Increased Apoptosis," *Toxicological Sciences*, 69:191-201 (2002).

Drake et al., "Exogenous vascular endothelial growth factor induces malformed and hyperfused vessels during embryonic neovascularization", Proc. National Acad. Sci. U.S.A., 92: 7657-7661 (Aug. 1995).

Driever et al., "Zebrafish: genetic tools for studying vertebrate development", Trends in Genetics, 10:152-159 (1994).

Dubois et al., "DNA adducts and P450 induction I nhuman, rat and avian liver cells after exposure to polychlorobiphenyls", Mutation Res., 345: 181-190 (1995).

Dumont et al., "Vascularization of the Mouse Embryo: A Study of *flk*-1, *tek, tie*, and Vascular Endothelial Growth Factor Expression During Development", Development Dynamics, 203: 80-92 (1995).

Eisses, "teratogenicity and Toxicity of Ethylene Glycol Monomethyl Ether (2-Methoxyethanol) in *Drosophila melanogaster*: Involvement of Alcohol Dehydrogenase Activity", Teratog, Carcinog, Mutagen., 9: 315-325 (1989).

Ellies et al., "Specific craniofacial cartilage dysmorphogenesis coincides with a loss of *dlx* gene expression in retinoic acid-treated zebrafish embryos", Mechanisms of Development, 61:23-26 (1997).

Ensenbach et al., "Toxicity of Complex Chemical Mixtures: Acute and Long-Term Effects on Different Life Stages of Zebrafish (*Brachydanio rerio*)", Ecotoxicology and Environmental Safety, 30: 151-157 (1995).

Fetcho et al., "Visualization of Active Neural Circuitry in the Spinal Cord of Intact Zebrafish," *Journal of Neurophysiology*, 73(1):399-406 (1995).

Feucht et al., "VEGF Induces Cardiovascular Malformation and Embryonic Lethality", Am G. Pathology, 151 (5): 1407-1416 (Nov. 1997).

Folkman, "Clinical Applications of Research on Angiogenesis", N. Eng. J. Med., 333(26): 1757-1763 (Dec. 28, 1995).

Fort et al., Phase III Interlaboratory Stude of Fetax, Part 2: Interlaboratory Validiation of an Exogenous Metabolic Activation system for Frogg Embryo Teratogensis Assay-Xenopus (Fetax), Drug and Chem Toxicol., 21(1): 1-14 (1998).

Fouquet et al, "Vessel Patterning in the Embryo of the Zebrafish: Guidance by Notochord", Development Biology, 183: 37-48 (1997).

Frank et al, "Residues of Insecticides, Fungicides, and Herbicides on Ontario-Grown Vegetables, 1980-1985", Assoc, Off. Anal. Chem., 70(6): 1081-1086 (1987).

Friedland el al, "Development or an Anti-Aβ Monoclonal Antibody for In Vivo Imaging of Amyloid Angiopathy in Alzheimer's Disease," *Molecular Neurobiology*, 9:107-113 (1994).

Gaiano et al., *Introducting genes into Zebrafish*, Elsevier, pp. O11-O14 (1996).

Gavrieli et al., "Identification of Programmed Cell Death in Situ via Specific Labeling of Neclear DNA Fragmentation", J. Cell Biol., 119(3): 493-501 (Nov. 1992).

Geling et al, "A γ-secretase inhibitor blocks Notch signaling in vivo and causes a severe neurogenic phenotype in zebrafish," *EMBO Reports*, 3(7):688-694 (2002).

Gerlai et al., "Drinks like a fish: zebra fish (*Danio rerio*) as a behavior genetic model to study alcohol effects," *Pharmacology, Biochemistry, and Behavior*, 67:773-782 (2000).

Ghosh et al, "Rational design of potent and selective EGFR tyrosine kinase as anticancer agents," *Curr. Cancer Drug Targets*, 1(2)129-140, abstract only (2001).

Granato et al., "Fishing for genes controlling development", Cur. Op. Gen. Dev., 6: 461-468 (1996).

Guest et al., "Evaluation of the rat embryo culture system as a predictive test for human teratogens", *Can J. Physiol. Pharmacol.*, 72: 57-62 (1994).

Guiney et al., "Correlation of 2, 3, 7, 8-Tetrachlordibenzo-*p*-dioxin Induction of Cytochrome P4501A in vascular Endothlium with Toxicity in Early Life Stages of Lake Trout," *Toxicology and Applied Pharmocol.*, 143:256-273 (1997).

Gupta et al., "Neuroprotective Role of Melatonin in Oxidative Stress Vulnerable Brain," *Indian J. Physiol Pharmacol*, 47(4):373-386 (2003).

Hammerschmidt et al., "Genetic analysis of dorsoventral pattern formation in the sebrafish: requirement of a BMP-like ventralizing activity and its dorsal repressor" Genes and Devel., 10:2452-2461 (1996).

Hanahan, "Signaling Vascular Morphogenesis and Maintenance", Science, 277: 48-50 (Jul. 4, 1997).

Heller et al., "Discovery and analysis of inflammatory diesase-related genes using cDNA microarrays", Proc. Natl. Acad. Sci. USA, 94: 2150-2155 (Mar. 1997).

Henry et al., "Early Life Stage Toxicity of 2,3,7,8-Tetrachlorodibenzo-p-dioxin in Zebrafish (*Danio rerio*)," *Toxicology and Applied Pharmacology*, 142:56-68 (1997).

Herbst et al., "Differential Effects of Liminin, Intact Type IV Collagen, and Specific Domains of Type IV Collagen on Endothelial Cell Adhesion and Migration", J. Cell Biol. 106: 1365-1373 (Apr. 1988).

Hetts, "To Die or Not to Die: An Overview of Apoptosis and its Role in Disease", JAMA, 279 (4): 300-307 (Jan. 28, 1998).

Higashijima et al., "High-Frequency Generation of Transgenic Zebrafish Which Reliably Express GFP in Whole Muscles or the Whole Body by Using Promoters of Zebrafish Origin," Developmental Biology, 192 289-299 (1997).

Hill et al., "Neurodevelopmental Defects in Zebrafish (*Danio rerio*) at Environmentally Relevant Dioxin (TCDD) Concentrations," *Toxicological Sciences*, 76:392-399 (2003).

Hitchcock et al., "Investigations into Using the Nematode *Caenorhabditis elegans* for Muncipal and Industrial Wastewater Toxicity Testing", Arch. Environ. Contam, Toxical., 33: 252-260 (1997).

Hunt et al., "A distinct Hox code for the branchial region of the vertebrate head", Nature, 353: 861-864 (Oct. 31, 1991).

Iida et al, "Suppression of the arachidonic acid casecade-mediated apoptosis in aflatoxin B1-induced rate hepatoma cells by glucocorticoids", Carcinogenesis, 19(7): 1191-1202 (1998).

Jain et al., "Quantitative angiogenesis assays: Progress and problems", Nat. Med., 390: 335-336 (Nov. 27, 1997).

Jowett, T., "Transgenic Zebrafish," *Methods in Molecular Biology*, 97:461-486 (1999).

Kerbel, "A cancer therapy resistant to resistance", Nature, 390: 335-336 (Nov. 27, 1997).

Kerr et al., "Apoptosis: A Basic Biological Phenomenon with Wide-Ranging Implication in Tissue Kinetics", Br. J. Cancer, 26: 239-257 (1972).

Khan et al., "Role of Serotonin in Fish Immunomodulation," *The Journal of Experimental Biology*, 200:1833-1838 (1997).

Khersonsky at al., "Facilitated Forward Chemical Genetics Using a Tagged Triazine Library and Zebrafish Embryo Screening," *J. Am. Chem. Soc.*, 125:11804-11085 (2003).

Kim et al., "Requirement for Specific Proteases in Cancer Cell Intravasation as Revealed by a Novel Semiquantitative PCR-Based Assay", Cell, 94: 353-362 (1998).

Knight, "Adverse Drug Reactions in Neonate", *J. Clin. Pharmacol.* 34:128-135 (1994).

Kurlandsky et al., "Plasma Delivery of Retinoic Acid to Tissues in the Rat," *J. Biol. Chem.*, 270(30):17850-17857 (1995).

Kuwada, J. Y., "Development of the zebrafish nervous system: genetic analysis and manipulation," *Current Opinion in Neurobiology*, 5:50-54 (1995).

Law et al., "Hepatotoxicity of the drinking water disinfection by-product, dichloroacetic acid, in the medaka small fish model", Toxicol. Letters, 94: 19-27 (1998).

Liao et al., "The zebrafish gene cloche acts upstream of a homologue to regulate endothelial cell differentiation", Development, 124: 381-389 (1997).

Liepins et al., "Cell Injury and Apoptosis", Scanning Microscopy, 8(3): 631-643 (1994).

Lin et al., "*lacZ* Expression in Germline Transgenic Zebrafish Can Be Detected in Living Embryos," *Developmental Biology*, 161:77-83 (1994).

Long et al., "GATA-1 expression pattern can be recapitulated in living transgenic zebrafish using GFP reporter gene", Development, 124: 4105-4111 (1997).

Losordo et al., "Gene Therapy for Myocardial Angiogenesis: Initial Clinical Results with Direct Myocardial Injection of phVEGF165 as Sole Therapy for Myocardial Ischemia", Circulatio, 98: 2800-2804 (1998).

Lundquist, Frank. "The Blood-Brain-Barrier in Some Freshwater Teleosts," *Acta Physiologica Scandinavica*, 4(3-4):201-206 (1942).

MacCubbin, "Passive perchronic carcinogen bioassay using rainbow trout (*Salmo gairdneri*) embryos," *Aquatic Toxicology*, 9:277-286 (1986).

Marret et al., "Caffeine-induced distrubances of early neurogenesis in whole mouse embryo cultures", Brain Research, 773:213-216 (1997).

Marty et al., "Age-dependent changes in toxicity of N-nitroso compounds in Japanese medaka (*Oryzias latiipes*) embryos," *Aquatic Toxicology*, 17:45-62 (1990).

McDanell et al., "Effect of Dietary Fat on the In Vitro Hepatotoxicity of Paracetamol", Biochemical Pharmacology, 44 (7): 1303-1306 (1992).

McGrath, P., "Introducing a new era in animal testing," *Analytical &Research Technology*, p. 51 (2002).

Macrae et al., "Zebrafish-Based Small Molecule Discovery," *Chemistry &Biology*, 10:901-908 (2003).

Meng et al., "Promoter analysis in living Zebrafish embryos identifies a cis-acting motif required for neuronal expression of GATA-2, " *PNAS*, 94:6267-6272 (1997).

Milan et al., "Drugs that induce Repolarization Abnormalities Cause Bradycardia in Zebrafish," *Circulation*, 107:1355-1358 (2003).

Miller et al., "Xenobiotic efflux pumps in insolated fish brain capillaries," *Am J Physiol Regulatory Integrative Comp Physiol*, 282:R191-198 (2002).

Mizell et al., "The aquatic vertebrate embryo as a sentinel for toxins: zebrafish embryo dechorionation and pervitelline space microinjection", Int. J. Dev. Biol., 41: 411-423 (1997).

Monteith et al., "Comparison of Tacrine-Induced Cytoxicity in Primiary Cultures of Rat, Mouse, Monkey, Dog, Rabbit, and Human Hepatocytes", Drug and Chem. Toxicol., 19 (1&2): 59-70 (1997).

Moore et al., "Murine Cerebral Microvascular Endothelium Incorporate and Metabolize 12-Hydroxyeicosatetraenoic Acid," *Journal of Cellular Physiology*,137:785-85 (1988).

Moos et at., "Cerebrovascular permeability to azo dyes and plasma proteins in rodents of different ages," *Neuropathology and Applied Neurobiology*, 19:120-127 (1993).

Muller et al., "Towards 3D structures of G protien-couples receptors: a multidisciplinary apporoach," Curr. Med. Chem., 7(9):861-888 abstract only (2000).

Muller et al., "Effect of Concentration on the cytotoxic Mechanism of Doxorubicine-Apoptosis and Oxidative DNA Damage", Biochem. Biophys. Res. Comm., 230(2): 254-257 (1997).

Mullins et al., "Large-scale Mutagenesis in the Zebrafish: In Search of Genes Controlling Development in a Vertebrate," *Current Biology, Current Science*, 4(3):189-202 (1994).

Mundle et al., "Two in Situ Labeling Techniquest Reveal Different Patterns of DNA Fragmentation during Spontaneous Apoptosis in Vivo and induct Apoptois In Vitro", Anticancer Res., 15: 254-257 (1997).

Opposition Brief dated Jan. 11, 2008 flied by opponent during opposition proceedings for EP 1 644 733.

O'Reilly et al., "Endostatin: An EndoGenous Inhibitor of Angiogenesis and Tumor Growth", Cell, 88: 277-285 (Jan. 24, 1997).

Ozato at al., "Production of transgenic fish: introduction and expression of chicken 8.- 122 0 229 Nb! crystallin gene in meclaka embryos", Cell Differentiation, 19:237-244 (1986). 0 61362582 v1.

Ozato et al., "Production of transgenic fish: introduction and expression of chicken ∂-crystallin gene in medaka embryos", *Cell Differentiation*, 19:237-244 (1986).

Parng et al., "Zebrafish: A Preclinical Model for Drug Screening," *Assay and Drug Development Technologies*, 1(1-1):41-48 (2002).

Peitsaro et al., "Modulation of the histaminergic system and behaviour by α-fluoromethylhistidine in zebrafish," *Journal of Neurochemistry*, 86:432-441 (2003).

Peters et al., "Green Fluorescent Fusion proteins: Powerful Tools for Monitoring Protein Expression in Live Zebrafish Embryos," *Development Biology*, 171:252-257 (1995).

Peterson et al., "Small molecule developmental screens reveal the logic and timing of vertebrate development," *PNAS*, 97:12965-12969 (2000).

Pradel et al., "Inhibition of Memory Consolidation by Antibodies against Cell Adhesion Molecules after Active Avoidance Conditioning in Zebrafish," *J. Neurobiol.*, 39:197-206 (1999).

Ransom et al., "characterization of Zebrafish mutants with defects in embryonic hematopoiesus, " *Development*, 123:311-319 (1996).

Relou et al., "Effect of culture condistions on the endothelial cell growth and responsiveness", Tissue & Cell, 30(5): 525-530 (1998).

Renier et al., "Genomic and functional conservation of sedative-hypnotic targets in the zebrafish," *Pharmacogenetics and Genomics*, 17:237-253 (2007).

Ritter et al., "In Vivo Imaging of Zebrafish Reveals Differences in the Spinal Networks for Escape and Swimming Movements," *The Journal of Neuroscience*, 21(22):8956-8965 (2001).

Rivard et al., "Age-Dependent Impairment of Angiogenesis", Circulation, 99: 111-120 (1999).

Roebuck et al., "A Review of the Neuroanatomical Findings in Children with Fetal Alcohol Syndrome or Prenatal Exposure to Alcohol", *Alcoholism: Clin. Exper. Res.*, 22 (2): 339-344 (Apr. 1998).

Seng et al., "A High Throughput In Vivo Zebrafish Angiogenesis Assay," *DrugPlus International*, pp. 22-24 (Nov. 2002).

Serbedzija et al., "Regulation in the heart field of zebrafish", *Development*, 125: 1095-1101 (1998).

Serbedzija et al., Analysis of Neural Crest Cell Migration in Splotch Mice Using A neural Crest-Specific LaeZ Report, Development Biology, 185: 139-147 (1997).

Serbedzija et al., Cell Death in the CNS of Wnt-1 Mutant Mouse, *J. Neurobio.*, 31(3): 275-282 (1996).

Serbedzija et al., Vital dye analysis of cranial neural crest cells in the mouse, *Development*, 116: 297-307 (1992).

Serbedzija et al., Development potential of trunk neural crest cells in the mouse, *Development*, 120: 1709-1718 (1994).

Semino et al., "Synthesis of Nod-like chitin oligosaccharides by the Xenopus development protein DG42", Proc. Natl. Acad. Sci USA, 92:3498-3501 (Apr. 1995).

Semino et al., "Expression of *Rhizobium* Chitin Oligosaccharide Fucosyltransferase in Zebrafish Embryos Disrupts Normal Development", *Annuals New York Academy of Sciences*, 842: 49-54 (1998).

Semino C. et al., "Homologs of the *Xenopus* development gene DDG-42 are present in zebrafish and mouse and are involved in the synthesis of Nod-like chitin oligosaccharides during early embryogenesis", Proc. Natl. Acad. Sci. USA, 93: 4548-4553 (May 1996).

Singer, "Sensitive Fluorescent Stains for Detecting Nucleic Acids in Gels and Solutions", Biotechnol. Intl., 1: 267-276 (1997).

Skov et al., "The blood volumes of the primary and secondary circulatory system in the Atlantic cod *Gadus morhua* L., using plasma bound Evans Blue and compartmental analysis," *The Journal of Experimental Biology*, 206:591-599 (2003).

Stainer et al., "Mutations affecting the formation and function of the cardiovascular system in the zebrafish embryo", *Development*, 123: 285-292 (1996).

Stainer et al., "The Zebrafish as a Model System to Study Cardiovascular Development", Trends Cardiosasc. Med., 45(5): 207-212 (1994).

Stellar, "Mechanisms and Genes of Cellular Suicide", Science, 267: 1445-1449 (Mar. 10, 1995).

Stopa et al., Albumin binds self-assembling dyes as specific polymolecular ligands, *International Journal of Biological Macromolecules*, 40:1-8 (2006).

Stringer et al., "Rapid Measuremen of Toxicity Using Electrochromic Dyes and Frog Embryos", *Bull. Environ. Contam. Toxicol.*, 51: 557-563 (1993).

Stuart et al., "Stable lines of transgenic zebrafish exhibit reproducible patterns of transgene expression,"*Development*, 109:577-584 (1990).

Stuermer et al., "Development of the Retinotectal Projection in Zebrafish Embryos under TTX-induced Neural -Impulse Blockade," *The Journal of Neuroscience*, 10(11):3615-3626 (1990).

Svoboda et al., "Nicotinic Receptors Mediate Changes in Spinal Motoneuron Development and Axonal Pathfinding in Embryonic Zebrafish Exposed to Nicotine," *The Journal of Neuroscience*, 22(24):10731-10741 (2002).

Terse et al., "Comparsion of In Vitro and In Vivo Biological Activity of Mycotoxins,"*Toxicon*, 31(7):913-919 (1993).

Thompson, C.B., "Apoptosis in the Pathogenesis and Treatment of Disease", Science 267: 145601462 (Mar. 10, 1995).

Thompson, M.A.et al., "The *cloche* and *spadetail* Genes Differentially Affect Hematopoiesis and Vasulogenesis", Dev. Biol., 197: 248-269 (1998), Science 267: 145601462 (Mar. 10, 1995).

Turk et al., "Synthetic Analogues of TNP-470 and Ovalicing Reveal a Common Molecular Basis for Inhibition of Angiogenesis and Immunosuppression", Bioorganic & Medicinal Chemistry, 6: 1163-1169 (1998).

Ungvary et al., "Combined Embryotoxic Action of Toluene, a Widely Used Industrial Chemical and Acetylsalicylic Acid (Aspirin)", Teratology 27:261-269 (1983).

Van De Waterbeemd et al., "Estimation of Blood-Brain Barrier Crossing of Drugs Using Molecular Size and Shape, and H-Bonding Descriptors," *Journal of Drug Targeting*, 6(2):151-165 (1998).

Van Eeden et al., "Chapter 2: Developmental Mutant Screens in the Zebrafish," *Methods in Cell Biology*, 60:21-41 (1999).

Van Leeuwen et al., "Fish Embryos as Teratogenicity Screens: A Comparison of Embryotoxicity between Fish and Birds", Ecotoxicol. Environ. Safety, 20: 42-52 (1990).

Weinstein et al., "*gridlock*, a localized heritable vascular patterning defect in the zebrafish", Nature Med., 1(11): 1143-1147 (Nov. 1995).

Westerfield, *The Zebrafish Book: A Guide for the Laboratory Use of Zebrafish (Danio rerio\*)*, 3d edition, (1993).

Wylie, Zebrafish Issue, Title page and Table of Contents, *i-ii, Development*, 123: 1-481 (1996).

Wolff et al., "Dexamethasone Increases Hepatotoxicity in MTX in Children with Brain Tumors", Anticancer Res., 18: 2895-2900 (1998).

Zetter, "Angiogenesis and Tumor Metastasis" *Annual Rev. Med.*, 49: 407-424 (1998).

Zhdanova et al., "Melatonin promotes sleep-like state in zebrafish," *Brain Research*, 903:263-268 (2001).

Restriction Requirement mailed Jun. 8, 2007 for U.S. Appl. No. 11/114,712.

Restriction Requirement mailed Aug. 22, 2007 for U.S. Appl. No. 11/280,849.

Restriction Requirement mailed Jan. 11, 2008 for U.S. Appl. No. 11/320,251.

Non-Final Office Action mailed Jan. 4, 2000 for U.S. Appl. No. 09/255,397, now US Patent No. 6,299,858.

Non-Final Office Action mailed Dec. 26, 2001 for U.S. Appl. No. 09/645,432, now US Patent No. 6,656,449.

Non-Final Office Action mailed Dec. 26, 2001 for U.S. Appl. No. 09/947,635, now US Patent No. 7,041,276.
Non-Final Office Action mailed Oct. 22, 2002 for U.S. Appl. No. 09/947,635, now US Patent No. 7,041,276.
Non-Final Office Action mailed Oct. 28, 2004 for U.S. Appl. No. 09/947,635, now US Patent No. 7,041,276.
Non-Final Office Action mailed Aug. 3, 2006 for U.S. Appl. No. 10/678,765.
Non-Final Office Action mailed Aug. 22, 2007 for U.S. Appl. No. 11/114,712.
Non-Final Office Action mailed Nov. 28, 2007 for U.S. Appl. No. 11/280,849.
Non-Final Office Action mailed Feb. 8, 2008 for U.S. Appl. No. 10/678,765.
Final Office Action mailed Oct. 25, 2000 for U.S. Appl. No. 09/255,397, now US Patent No. 6,299,858.
Final Office Action mailed Oct. 22, 2002 for U.S. Appl. No. 09/645,432, now US Patent No. 6,656,449.
Final Office Action mailed Jul. 15, 2003 for U.S. Appl. No. 09/947,636, now US Patent No. 7,041,276.
Final Office Action mailed Apr. 12, 2007 for U.S. Appl. No. 10/678,765.
Advisory Action mailed Feb. 5, 2001 for U.S. Appl. No. 09/255,397, now US Patent No. 6,299,858.
Advisory Action mailed Feb. 11, 2003 for U.S. Appl. No. 09/645,432, now US Patent No. 6,656,449.
Advisory Action mailed Jan. 22, 2004 for U.S. Appl. No. 09/947,635, now US Patent No. 7,041,276.
Examiner Interview Summary mailed Mar. 5, 2001 for U.S. Appl. No. 09/255,397, now US Patent No. 6,299,858.
Examiner Interview Summary mailed Mar. 30, 2001 for U.S. Appl. No. 09/255,397, now US Patent No. 6,299,858.
Examiner Interview Summary mailed Apr. 21, 2001 for U.S. Appl. No. 09/255,397, now US Patent No. 6,299,858.
Examiner Interview Summary mailed Mar. 17, 2003 for U.S. Appl. No. 09/645,432, now US Patent No. 6,656,449.
Examiner Interview Summary mailed Mar. 17, 2003 for U.S. Appl. No. 09/947,635, now US Patent No. 7,041,276.
Examiner Interview Summary mailed Feb. 20, 2004 for U.S. Appl. No. 09/947,635, now US Patent No. 7,041,276.
Examiner Interview Summary mailed Nov. 23, 2004 for U.S. Appl. No. 09/947,635, now US Patent No. 7,041,276.
Notice of Allowance mailed May 7, 2001 for U.S. Appl. No. 09/255,397, now US Patent No. 6,299,858.
Notice of Allowance mailed May 28, 2003 for U.S. Appl. No. 09/645,432, now US Patent No. 6,656,449.
Notice of Allowance mailed Jul. 6, 2005 for U.S. Appl. No. 09/947,635, now US Patent No. 7,041,276.
Blader et al., "Ethanol Impairs Migration of the Prechordal Plate in the Zebrafish Embryo," Developmental Biology, 201:185-201 (1998).
Erasmus et al., "Aluminum Neurotoxicity in Experimental Animals," Ther. Drug Monit., 15(6):588-592 (1993). Abstract only.
Hiraoka et al., "The Uses of a Charge-Coupled Devices for Quantitative Optical Microscopy of Biological Structures", Science, 238:36-41 (1987).
Kimmel et al., "Stages of Embryonic Development of the Zebrafish," Developmental Dynamics, 203:253-310 (1995).
Miller et al., "Biochemical, Functional and Morphological Indicators of Neurotoxicity: Effects of Acute Administration of Trimethyltin to the Developing Rat," J. Pharmacol Exp. Ther., 231(3);744-751 (1984) Abstract only.
O'Callaghan et al., "Enhanced expression of Glial Fibrillary Acidic Protein and the Cupric Silver Degeneration Reaction can be Used as Sensitive and Early Indicators of Neurotoxicity," Neurotoxicology, 13(1):113-122 (1992) Abstract only.
O'Callaghan et al., "Neurotoxicology Profiles of Substituted Amphetamines in the C57BL/6J Mouse," J. Pharmacol Exp. Ther., 270(2):741-751 (1994). Abstract only.
Verity, Ca(2+)-dependent Processes as Mediators of Neurotoxicity, Neurotoxicology, 13(1):139-147 (1992). Abstract Only.
Restriction Requirement mailed Nov. 4, 2008 for U.S. Appl. No. 11/515,355.
Non-Final Office Action mailed Jun. 1, 2009 for U.S. Appl. No. 10/678,765.
Non-Final Office Action mailed Jun. 1, 2009 for U.S. Appl. No. 11/320,251.
Non-Final Office Action mailed Jan. 12, 2009 for U.S. Appl. No. 11/515,355.
Non-Final Office Action mailed Jul. 14, 2009 for U.S. Appl. No. 11/515,355.
Final Offce Action mailed Jan. 14, 2009 for U.S. Appl. No. 11/320,251.
Advisory Action mailed Apr. 24, 2009 for U.S. Appl. No. 10/678,765.

* cited by examiner

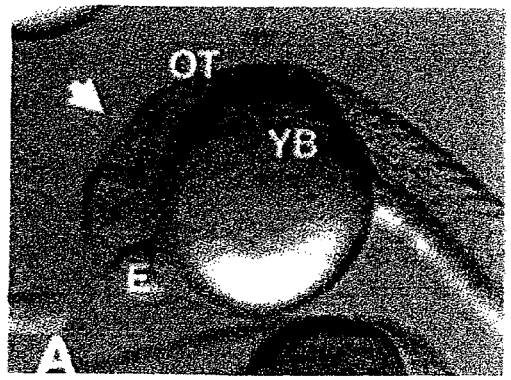
Figure 10A
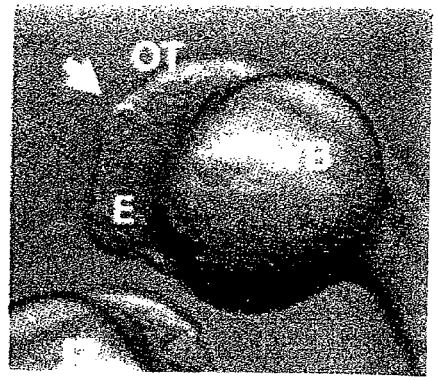
Figure 10B
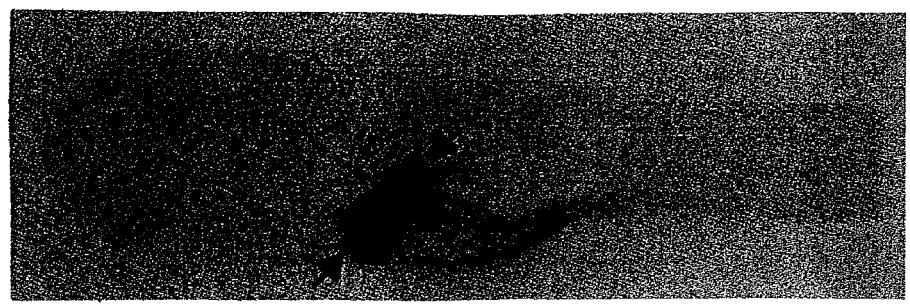
Figure 11
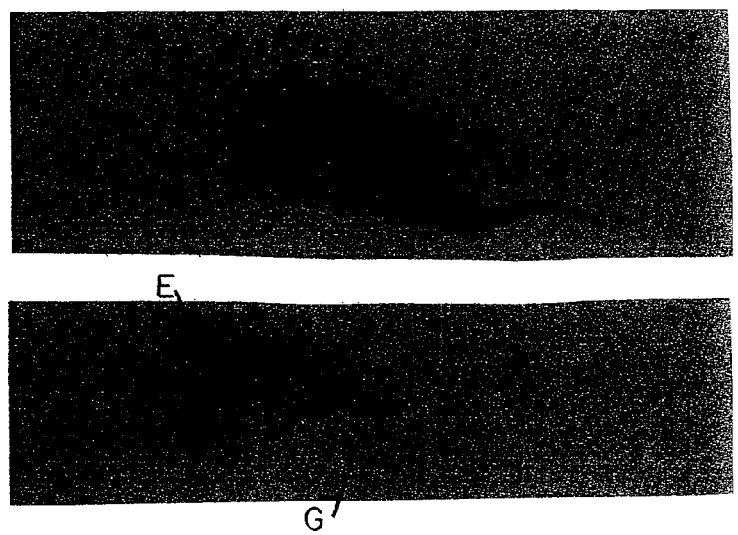
Figure 12A
Figure 12B

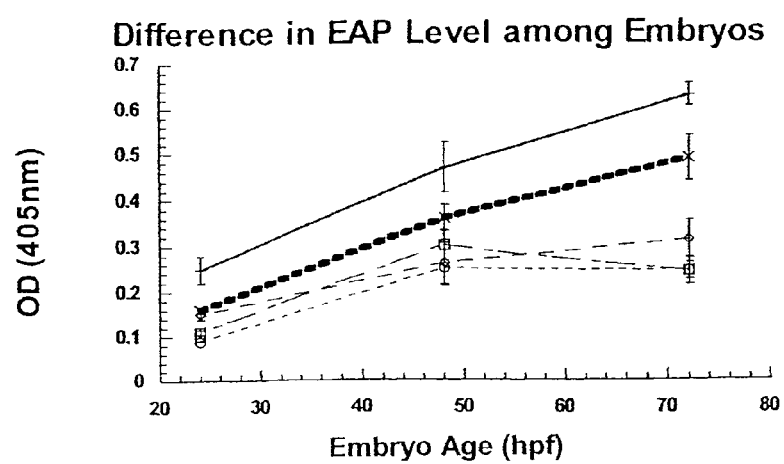
Figure 16B
Figures 17A, B, C

Figure 25
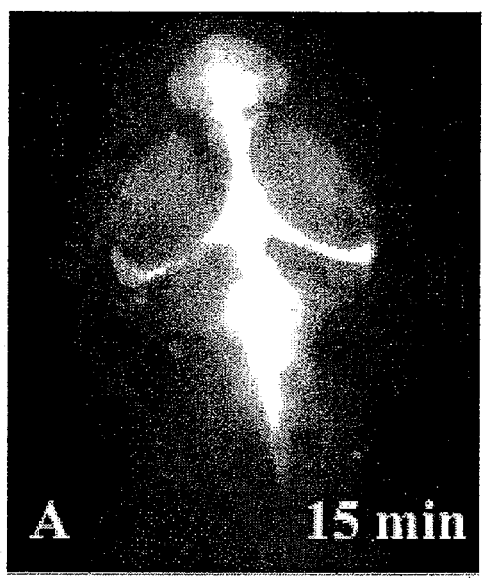
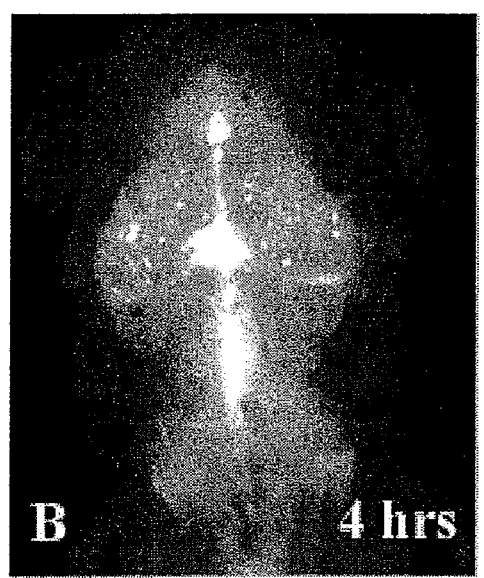
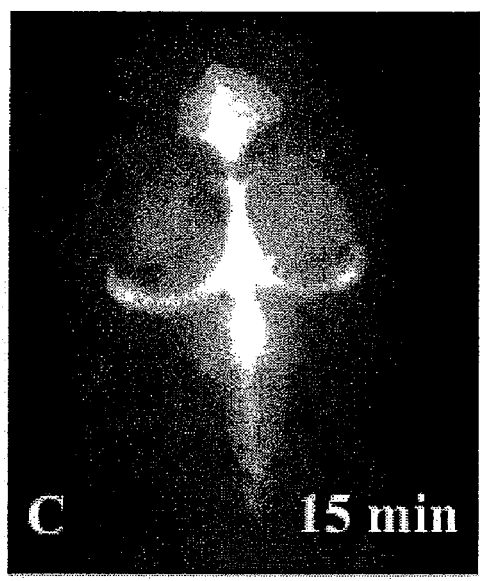
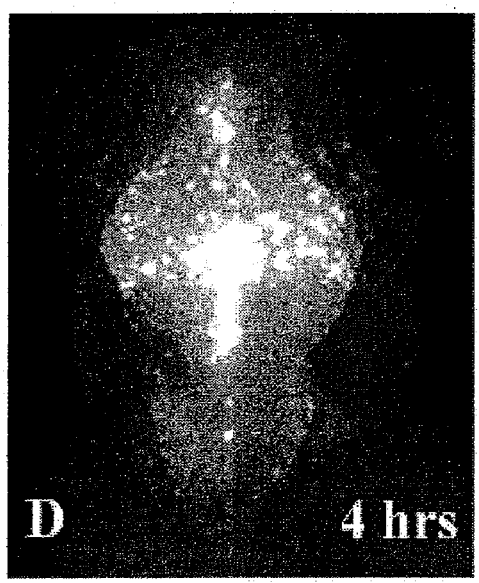

METHODS OF SCREENING AGENTS FOR ACTIVITY USING TELEOSTS

CROSS-REFERENCE TO RELATED APPLICATIONS

The present application is a continuation of U.S. application Ser. No. 11/515,355, filed Sep. 1, 2006. Commonly owned co-pending U.S. Patent Application Ser. No. 60/110,464, filed Dec. 1, 1998 is directed to related subject matter and is incorporated herein by reference in its entirety for all purposes.

STATEMENT AS TO RIGHTS TO INVENTIONS MADE UNDER FEDERALLY SPONSORED RESEARCH AND DEVELOPMENT

This invention was supported by grants from the National Institutes of Health (Grant Nos. 1R43CA7938-01, 1R43NS048607, 1R43NS050874, and 2R44CA83256). The Government may have certain rights in this invention.

BACKGROUND OF THE INVENTION

Currently, searches for target-specific therapeutic and prophylactic compounds that have the ability to enhance or inhibit angiogenesis activity, enhance or inhibit cell death activity, and/or exhibit low toxicity comprise three major focuses of drug discovery and development. Angiogenesis plays an important role not only in the further development of the embryonic vasculature, but also in many post-natal processes, such as wound healing and tissue and organ regeneration. Angiogenesis has also been identified as a critical process for solid tumor growth. Furthermore, uncontrolled blood cell proliferation and excessive angiogenesis have been shown to constitute significant pathogenic components in numerous diseases, including rheumatoid arthritis, atherosclerosis, diabetes mellitus, retinopathies, psoriasis, and retrolental fibroplasia.

Methods of screening agents for an ability to inhibit or enhance angiogenesis activity would be useful in identifying those agents that would be effective in therapeutic or prophylactic treatment of a variety of diseases involving angiogenesis processes. For example, angiogenesis inhibition is a powerful potential approach for ameliorating cancer (Folkman, New Eng. J. Med. 333:1757-1763 (1995); Kerbel, Nature 390:355 (1997)) and for reversing blood vessel loss associated with tissue ischemia, such as diabetic retinopathy (Bonn, Lancet 348:604 (1996); Breier et al., Haemist. 78 (1):678-683 (1997). It appears that anti-angiogenic therapies do not induce acquired drug resistance (Boehm et al., Nature 390: 404-407 (1997))—a major problem with current cancer therapies. However, few therapeutic candidate molecules exist. It would therefore be desirable to provide methods of identifying compounds that inhibit angiogenesis and have therapeutic activities against diseases that would benefit from angiogenesis inhibition, such as cancer and diabetes. Similarly, methods of screening for compounds that enhance angiogenesis by stimulating blood vessel formation would be advantageous for use in minimally invasive approaches for improving circulatory function in various diseases, such as coronary artery disease, congestive heart failure, peripheral arterial disease, and peripheral venous disease. Unfortunately, many current assays for angiogenesis do not permit in vivo assessment of compounds or their side effects in whole animal models, or in multiple tissues or organs of animal models simultaneously and over time. In addition, many current assays for angiogenesis activity are not suitable for rapid, automated, or extensive compound screening, particularly screening of compound libraries containing numerous compounds, due to their complexity.

The search for compounds that can regulate promote or inhibit cell death has also been of vital interest. Necrosis and apoptosis are two known types of cell death. Necrosis involves the pathologic death of living tissue in a subject due to non-physiological injury to cells of the tissue. Apoptosis, which involves programmed cell death, is a physiological process that ensures that an equilibrium is maintained between cell proliferation and cell differentiation in most self-renewing tissues of multicellular organisms. Regulation of cell death activity (in particular, apoptosis) constitutes an important mechanism in therapeutic and prophylactic approaches to many diseases, including, e.g., cancer and organ transplantation. Existing models for assessing apoptosis activity include the nematode worm, C. elegans. Although the nematode has many advantages as a model system, it is not the optimum model for evaluating vertebrate cell death activity or for use in screening compounds for potential therapeutic activity in vertebrates.

There are currently two approaches for detecting cell death activity in vertebrate hosts. The first approach uses standard cell culture techniques and typically relies on standard microplate readers to detect the death of cells cultured from an organism. A major drawback of the cell culture assay format is that it does not permit analysis of the effects of a compound on cell types that have not been cultured (i.e., other cell types). It also does not allow evaluation of the effects of a compounds on specific tissues or organs or in an intact whole host in vivo. Furthermore, such an assay format does not permit the monitoring of cell death activities in multiple tissues, organs, or systems of a live host simultaneously or the continued monitoring of such activities over time. In addition, the cell culture assay approach does not allow for rapid or automated high-throughput screening of many compounds.

A second approach to detecting cell death activity utilizes a histochemical staining technique, designated terminal deoxyuridine nucleotide end labeling (TUNEL), to detect dead or dying cells in sectioned tissues of vertebrate embryos. Unfortunately, with this approach, only a single time point in the life cycle of the host can be examined; the death of cells in various tissues or organs of the subject over a period of time cannot be monitored. Because many degenerative diseases occur in stages, the ability to examine changes in the pattern of cell death activity caused by a compound and the duration of direct and side effects of the compound on multiple tissues and organs would represent a significant improvement over such methods. Moreover, because the TUNEL approach requires that cells be fixed for visualization, effects in a live animal cannot be monitored.

The identification of target-specific therapeutic and prophylactic compounds that exhibit low toxicity and/or side effects has also been focal point of drug discovery and development. Evaluation of the potential impact of different compounds on humans and animal health is a major component of risk assessment. There is increasing concern that current toxicity test procedures are inadequate. A number of cell-based in vitro toxicity screens have been developed. Significantly, however, these screens do not permit evaluation of the toxic effects of a compound in vivo on an intact animal. Notably, these cell-based assays are designed at the molecular and cellular levels; as a result, determining the impact of a compound of interest on higher levels of cellular organization, such as the circulatory system and neurodevelopment, still requires subsequent whole animal testing. In addition, current screens do not permit the assessment of drug effects on all potential target cells, tissues, or organs of an animal. Nor can the effects of a compound on multiple target tissues and organs be studied simultaneously or over time using current assays. Underscoring the need for the development of more predictive and comprehensive toxicity screening methods, many compounds that pass preliminary cell-based testing fail final large animal toxicity testing, a prerequisite for eventual FDA approval. Furthermore, some potential therapeutic compounds that do not produce immediate lethality induce toxic effects in specific organs and tissues. There is a need for a cost-effective, comprehensive methods for screening compounds for toxic activity in whole animals and in one or more designated target tissues and organs in vivo and in cells in vitro and over time.

SUMMARY OF THE INVENTION

The present invention relates generally to methods of screening an agent for an activity in a teleost. In one aspect, methods of screening an agent for an angiogenesis activity in vivo or in vitro are provided. Some such methods comprise administering the agent to a whole teleost in vivo and detecting a response in the teleost or in at least one tissue or organ of the teleost indicating the angiogenesis activity. Other such methods comprise administering the agent to cells of a teleost in vitro and detecting a response in such cells indicating the angiogenesis activity. In some such methods, the response is a reduction in blood vessel formation relative to an untreated teleost. In other such methods, the response is an increase in blood vessel formation relative to an untreated teleost.

In another aspect, the invention provides methods of screening an agent for an effect on cell death activity in vivo or in vitro. Some such methods comprise administering the agent to a whole teleost in vivo and detecting a response in the teleost or in at least one tissue or organ of the teleost or cells thereof indicating an effect on cell death activity. Some such methods comprise administering the agent to cells of a teleost in vitro and detecting a response in such cell indicating an effect on cell death activity. In some such methods, the response is an increase in cell death activity. In other such methods, the response is a decrease in cell death activity. The cell death activity may comprise apoptotic or necrotic activity. In some such methods, a fluorescent dye which labels dead or dying cells is administered to facilitate detection of cell death activity. In some such methods, the fluorescent dye is administered to the teleost prior to the administration of the agent. In some such methods, the fluorescent dye is an unsymmetrical cyanine dye, such as a quinolium dye.

Also provided are methods of screening an agent for toxic activity in vivo or in vitro. Some such methods comprise administering the agent to a whole teleost in vivo and detecting a response in the teleost or in at least one tissue or organ of the teleost indicating toxicity. Other such methods comprise administering the agent in vitro to cells of a teleost and detecting a response in the cells indicating toxicity. In some such methods, the response is detected in two or more organs of the teleost simultaneously.

In another aspect, the present invention provides methods of screening an agent for angiogenesis activity and toxicity in vivo or in vitro. Some such methods comprise administering the agent to a whole teleost in vivo and detecting a response in the teleost indicating angiogenesis activity and/or toxicity. Other such methods comprise administering the agent in vitro to cells of a teleost and detecting a response in the cells indicating angiogenesis activity and/or toxicity.

In yet another aspect, the present invention includes methods of screening an agent for angiogenesis activity and an effect on cell death activity in vivo or in vitro. Some such methods comprise administering the agent to a teleost in vivo and detecting a response in the teleost indicating angiogenesis activity and/or an effect on cell death activity. Other such methods comprise administering the agent in vitro to cells of a teleost and detecting a response in the cells indicating angiogenesis activity and/or an effect on cell death activity.

The present invention also includes methods of screening an agent for an effect on cell death activity and toxic activity in vitro or in vivo. Some such methods comprise administering the agent in vivo to a teleost and detecting a response in the teleost indicating an effect on cell death activity and/or toxicity. Other such methods comprise administering the agent in vitro to cells of a teleost and detecting a response in the cells indicating an effect on cell death activity and/or toxicity.

The invention further provides methods of screening an agent for a pharmacological activity. Such methods entail providing a multi-well plate, the wells containing teleosts. Agents are then into different wells of the multi-well plate, and incubating the agents with the teleosts for sufficient time to induce a response in the teleosts indicative of the pharmacological activity. A labelling reagent is introduced into each well, which, through processing by or binding to a component of the teleost, generates a detectable signal dependent on the extent of the response in the teleost. A signal is detected in each well as an indication of the pharmacological activity of the agent introduced in the well. In some methods, the detectable signal is an optically detectable signal, which can be detected, for example, by a microplate reader. In some methods, a single teleost occupies in each well. In some methods, the teleosts are zebrafish. In some methods, the teleosts are synchronized embryos.

In some methods, the labelling reagent is a substrate of an enzyme, and the response is an increase or decrease in activity of the enzyme. In some methods, the labelling reagent comprises an antibody, and the detectable signal is generated by the antibody bound to a cellular receptor of the teleost. In some methods, the response is a change in number of cells or types of cells of the teleost. In some methods, the labelling reagent is a nucleic acid, and the detectable signal is generated by the nucleic acid bound to a nucleic acid of the teleost. In some methods, the labelling reagent is contacted with a second labelling reagent that binds to the labelling reagent thereby generating the detectable signal. In some methods, the pharmacological activity is modulation of angiogenesis, the response is a change in alkaline phosphatase activity of the teleost and the labelling reagent is a substrate for alkaline phosphatase. In some methods, the pharmacological activity is modulation of apoptosis, the response is a change in level of a caspase activity of the teleost and the labelling reagent is a substrate for the caspase.

In some methods, optical density is determined within each well to distinguish teleosts that survive incubation with the agent and teleosts that die due to incubation with the agent. In some methods, subsequent steps of introducing a labelling agent and detecting signal are performed on a subset of wells containing teleosts that survive incubation with the compound. Some methods are followed by performing a confirmatory assay on a subset of agents indicated to have the pharmacological activity. The confirmatory assay entails detecting a second response of the teleosts, the same or different than the response, wherein the second response is a confirmatory indicator of the pharmacological activity. In some such methods, the response and the second response are the same, and the response is detected with preformed with a plate reader, and the second response is detected with a microscope. Some methods further comprise determining an LD50 on a subset of agents indicated to have pharmacological activity. Some methods further comprise determining organ-specific toxicity on a subset of agents indicated to have pharmacological activity.

The invention further provides methods of monitoring distribution of an agent between teleosts and a surrounding medium. In such methods, a multi-well plate is provided in which the wells containing teleosts in a medium, and either the medium or the teleosts or both containing an agent. The teleosts are cultured in the wells. In each well, the amount of the agent in the medium, in the zebrafish or both is determined. Such methods can be used to determine absorption rate, excretion rate of metabolism rate of the agent.

The invention further provides methods of screening an agent for a property. Such methods entail providing a multi-well plate, the wells containing teleosts. Agents are introduced into different wells of the multi-well plate, and the agents are incubated with the teleosts for sufficient time to induce a response. The response is detected in each well as an indication of the property of the agent introduced in the well.

The invention further provides methods of screening an agent for an activity in the brain or central nervous system (CNS) in a teleost, preferably a zebrafish, in vivo. Some such methods comprise administering an agent in vivo to a zebrafish, detecting a response the brain or CNS of the zebrafish, and comparing the response in the agent-treated zebrafish with the response in a zebrafish administered with no agent or a control agent, in which a difference in the response in the agent-treated zebrafish compared to the untreated or control agent-treated zebrafish indicates the agent has an activity in the brain or CNS of the zebrafish. In some methods, the agent is known to penetrate the blood brain barrier (BBB) and the method is performed on zebrafish of any age. In some methods, the agent is known not to penetrate the BBB and the method is performed on either zebrafish of age less than 3 days post-fertilization, or on zebrafish of age at least 3 days post-fertilization and the agent is administered by direct delivery to the brain or CNS. In some methods, it is not known whether the agent penetrates the BBB, or the agent is screened without regard for whether it penetrates the BBB, and the method is performed on either zebrafish of age less than 3 days post-fertilization, or zebrafish of age at least 3 days post-fertilization. In some methods, the agent is administered to the zebrafish by dissolving the agent in the media (i.e., fish water) containing the zebrafish. In some methods, the agent is injected into the zebrafish. In some methods, the agent is administered by direct delivery to the brain or CNS of the zebrafish. In some methods, direct delivery of the agent to the brain or CNS of the zebrafish is by microinjection into the brain or CNS. In some methods, the agent is administered to the zebrafish in conjunction with a carrier. In some methods, the carrier is a solvent, lipid, or peptide. In some methods, the agent is administered to the zebrafish in conjunction with at least one other compound. In some methods, the agent is fluorescent or radioactive. In some methods, the agent is a small molecule and a library of small molecules is screened for the activity in the brain or CNS. In some methods, the agent is a nucleic acid, peptide, protein, glycoprotein, carbohydrate, lipid, or glycolipid. In some methods, the nucleic acid is DNA or RNA. In some methods, the method is performed in a multi-well format. In some methods, a single zebrafish occupies at least some of the wells. In some methods, a plurality of zebrafish occupy at least some of the wells. In some methods, the zebrafish is an embryo, larva, or adult.

In some methods, the zebrafish is a zebrafish embryo. In some methods, the zebrafish is a wild-type strain. In some methods, the zebrafish is a transgenic zebrafish. In some methods, the zebrafish has a heritable mutation. In some methods, the heritable mutation is associated with a brain or CNS disease or disorder.

The invention further provides methods of screening an agent for an effect on a brain or CNS disease or disorder in a zebrafish in vivo in which the brain or CNS disease or disorder has been induced in the zebrafish upon administration of a compound. Some such methods comprise administering a compound in vivo to a zebrafish, in which the compound induces a phenotype in the zebrafish that mimics a brain or CNS disease or disorder, administering an agent in vivo to the zebrafish, detecting a response in the brain or CNS of the zebrafish, comparing the response in the agent-treated zebrafish with the response in the compound-treated zebrafish administered with no agent or a control agent, in which a difference in the response in the agent-treated zebrafish compared to the untreated or control agent-treated zebrafish indicates the agent has an effect on the brain or CNS disease or disorder in the zebrafish.

The invention further provides methods of screening an agent for an ability to affect blood brain barrier (BBB) permeability in a teleost, preferably a zebrafish, in vivo. Some such methods comprise administering an agent to the zebrafish of age at least 3 days post-fertilization, administering a fluorescent dye to the zebrafish, detecting a response in the zebrafish; and comparing the response in the agent-treated zebrafish with the response in a zebrafish administered with no agent or a control agent, in which a difference in the response in the agent-treated zebrafish compared to the untreated or control agent-treated zebrafish indicates the agent has the ability to affect BBB permeability. In some methods, the response indicating that the agent has the ability to affect BBB permeability is retention of the fluorescent dye in the brain or CNS of the zebrafish. In some methods, the response is an increase in retention of the fluorescent dye in the brain or CNS of the zebrafish. In some methods, the fluorescent dye is rhodamine-123. In some methods, the fluorescent dye is FITC-HRP. In some methods, the fluorescent dye is detected by fluorescence microscopy. In some methods, the fluorescent dye is administered prior to administering the agent to the zebrafish. In some methods, the fluorescent dye is administered after administering the agent to the zebrafish. In some methods, the fluorescent dye is administered to the zebrafish by dissolving the dye in the media (i.e., fish water) containing the zebrafish. In some methods, the agent is administered to the zebrafish by dissolving the agent in the media (i.e., fish water) containing the zebrafish. In some methods, the agent is injected into the zebrafish. In some methods, the agent is administered by direct delivery to the brain or CNS of the zebrafish. In some methods, direct delivery to the brain or CNS of the zebrafish is by microinjection of the agent into the brain or CNS. In some methods, the agent is administered to the zebrafish in conjunction with a carrier. In some methods, the carrier is a solvent, lipid, or peptide. In some methods, the agent is administered to the zebrafish in conjunction with at least one other compound. In some methods, the agent is fluorescent or radioactive. In some methods, the agent is a small molecule and a library of small molecules is screened for permeability of the BBB. In some methods, the agent is a nucleic acid, peptide, protein, glycoprotein, carbohydrate, lipid, or glycolipid. In some methods, the nucleic acid is DNA or RNA. In some methods, the method is performed in a multi-well format. In some methods, a single zebrafish occupies at least some of the wells. In some methods, a plurality of zebrafish occupy at least some of the wells. In some methods, the zebrafish is an embryo, larva, or adult. In some methods, the zebrafish is a zebrafish embryo. In some methods, the zebrafish is a wild-type strain. In some methods, the zebrafish is a transgenic zebrafish. In some methods, the zebrafish has a heritable mutation. In some methods, the heritable mutation is associated with a brain or CNS disease or disorder.

The invention further provides methods of screening an agent for a first activity in the brain or central nervous system (CNS), and for a second activity in at least one other tissue or organ, in a teleost, preferably a zebrafish, in vivo. Some such methods comprise administering an agent in vivo to a zebrafish, detecting a first response indicating a first activity in the brain or CNS of the zebrafish, comparing the first response in the agent-treated zebrafish with the response in a zebrafish administered with no agent or a control agent, in which a difference in the response in the agent-treated zebrafish compared to the untreated or control agent-treated zebrafish indicates the agent has the first activity in the brain or CNS of the zebrafish, detecting a second response in the at least one other tissue or organ of the zebrafish, and comparing the second response in the at least one other tissue or organ of the agent-treated zebrafish with the second response in the at least one other tissue or organ of a zebrafish administered with no agent or a control agent, in which a difference in the second response in the agent-treated zebrafish compared to the untreated or control agent-treated zebrafish indicates the agent has the second activity in the at least one other tissue or organ of the zebrafish. In some methods, the first activity and the second activity are the same. In some methods, the first activity and the second activity are different.

The invention further provides methods of screening an agent for an ability to affect blood brain barrier (BBB) permeability, and for an activity in at least one other tissue or organ, in a teleost, preferably a zebrafish, in vivo. Some such methods comprise administering an agent in vivo to a zebrafish, detecting a first response in the zebrafish, comparing the response in the agent-treated zebrafish with the response in a zebrafish administered with no agent or a control agent, in which a difference in the response in the agent-treated zebrafish compared to the untreated or control agent-treated zebrafish indicates the agent has the ability to affect BBB permeability, detecting a second response in at least one other tissue or organ of the zebrafish, and comparing the second response in the at least one other tissue or organ of the agent-treated zebrafish with the second response in the at least one other tissue or organ of a zebrafish administered with no agent or a control agent, in which a difference in the second response in the agent-treated zebrafish compared to the untreated or control agent-treated zebrafish indicates the agent has the second activity in the at least one other tissue or organ of the zebrafish. In some methods, the at least one other tissue or organ is the brain or CNS. In some methods, the at least one other tissue or organ is other than the brain or CNS.

A further understanding of the nature and advantages of the inventions herein may be realized by reference to the detailed description of the specification and the associated figures.

BRIEF DESCRIPTION OF THE FIGURES

FIG. 3A represents a control; FIG. 3B shows a treated embryos treated with a compound from the NCI library. Both embryos are morphologically normal, however, the treated embryo has failed to form any SIVs (arrow) and shows a specific loss of the subintestinal vessels. The eye (E), yolk (Y) and fin (F) of the embryos are labeled for orientation. Scale bar=100 μm.

In this lateral view of the trunk, intersomitic vessels (arrows), which are sprouting from the dorsal aorta (A), are labeled with the probe. Anterior is to the left and dorsal is up.

Figure 9:
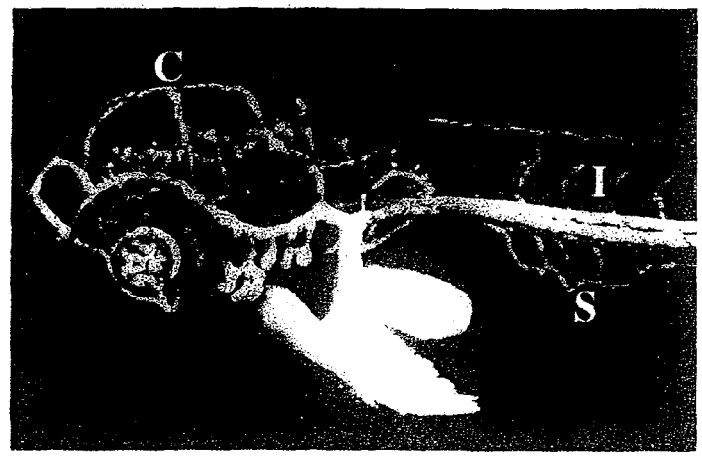

FIG. 9 is a microangiograph showing lateral profile of a zebrafish embryo at day three of development, depicting the normal vascular pattern, including the cranial (C), intersegmental (I) and subintestinal (S) vessels. The letter "H" denotes the heart, and the letter "E" denotes the eye. The data to construct the microangiograph was acquired from an epifluorescence microscope and processed using digital image processing software.

FIGS. 10A and 10B are compound microscope photographs (10× objective) under a compound microscope showing, respectively, a phase image of a normal (FIG. 10A) zebrafish embryo and a retinoic acid-treated (FIG. 10B) zebrafish embryo. The embryo treated with retinoic acid (vitamin A acid, Sigma Chemical Co.) was exposed to 1 μM retinoic acid (RA) at 12 to 14 hours. Apoptosis occurred in the hindbrain of the RA-treated embryo, as evidenced by the disorganization of the hindbrain and the significant reduction in distance between the otic vesicle and the eye in the retinoic acid-treated embryo, as compared with the normal embryo (compare arrows in FIGS. 10A and 10B). The letter "E" denotes the eye, the letters "YB" signify the yolkball, and the letters "OT" denote the otic vesicle.

FIG. 11 is a photograph through a dissecting microscope showing a lateral view of a 5 day zebrafish embryo stained with streptavidin-conjugated peroxidase. Both the liver (arrows) and the gut (G) are stained. The eye (E) and the otic vesicle (OV) of the embryo are labeled for orientation. The magnification is comparable to FIGS. 12A and 12B.

FIGS. 12A and 12B are photographs through a dissecting microscope which show a dose response of zebrafish embryos to which specific dosages of dexamethasone had been administered. Zebrafish embryos were treated for five days with dexamethasone to determine the effect of dexamethasone on liver development and function. The embryos were fixed with paraformaldehyde and incubated with streptavidin-peroxidase to detect the liver after incubating with a chromogenic dye. The arrows indicate the position of the liver. FIG. 12A (top), six day old untreated embryo (control embryo); FIG. 12B (bottom), six day old embryo treated with 100 μM of dexamethasone for five days. Embryos treated with dexamethasone showed a dramatic reduction in liver size compared with control embryos. Scale bar=1 millimeter (mm); Eye (E); Gut (G); Tail (T).

Figure 13:
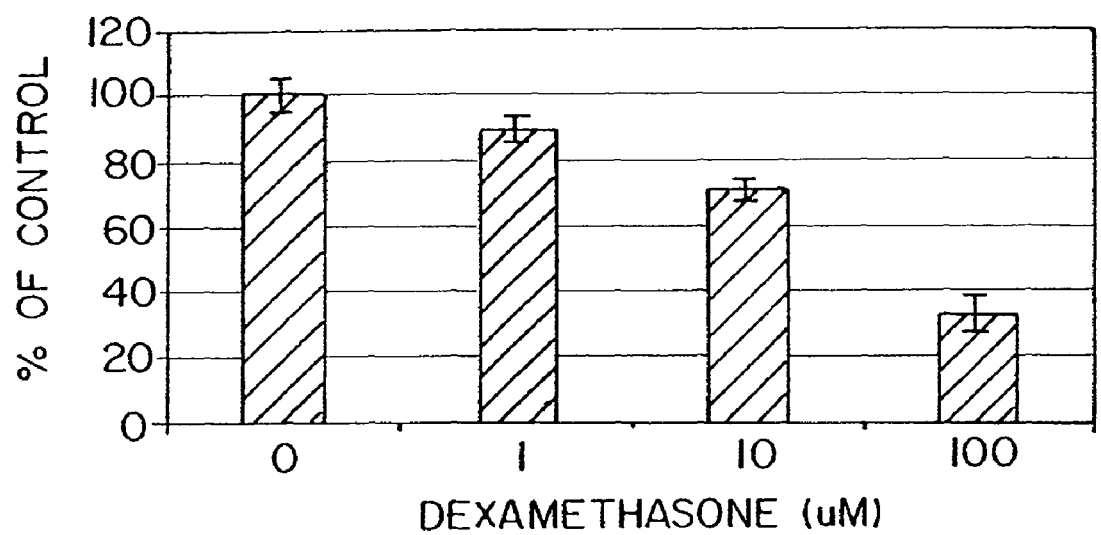

FIG. 13 is a graphical illustration showing a dose response of zebrafish embryos to various dosages of dexamethasone. Zebrafish embryos were exposed to different concentrations of dexamethasone (i.e., concentrations ranging from 1 μM to 100 μM) for five days as described for FIGS. 12A and 12B. After treatment, the embryos were stained with a soluble dye to detect liver defects specifically. After staining, the product formed by peroxidase was detected by absorbance at 405 nanometers (nm). The values were expressed as a percentage of control (% Control), where the control (i.e., untreated embryos) is 100%. The standard deviation was also calculated and added to the data. Liver toxicity resulting from dexamethasone is suggested by a reduction in liver size.

Figure 14:

FIG. 14 is a photograph of a six day old zebrafish embryo fixed with paraformaldehyde and stained for alkaline phosphatase. The arrow indicates the position of the stained embryonic kidney. Scale bar=1 mm; Eye (E); Gut (G); Tail (T).

Figure 15:
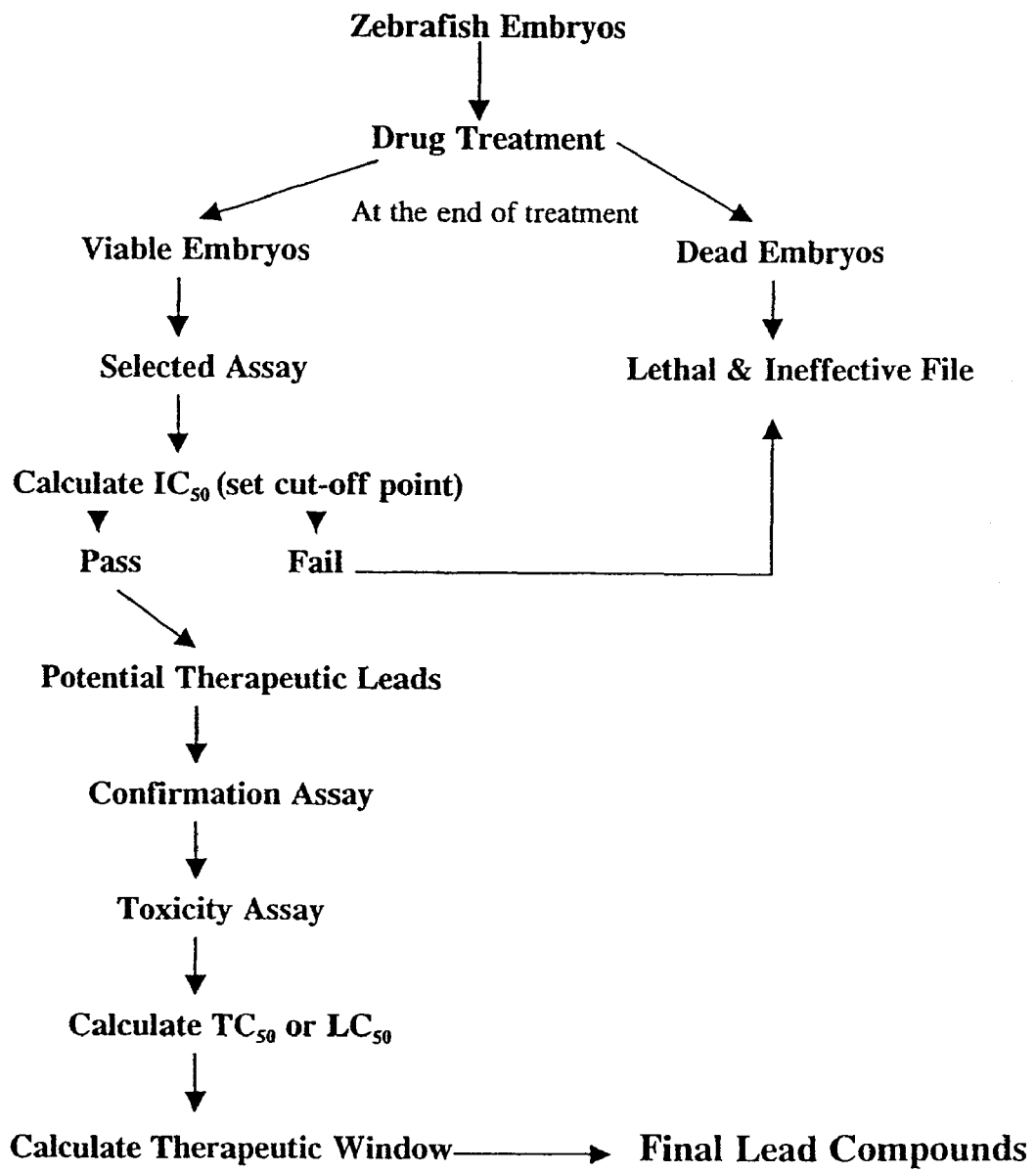

FIG. 15: Flow chart of an exemplary high throughput screening assay.

Figure 16A:
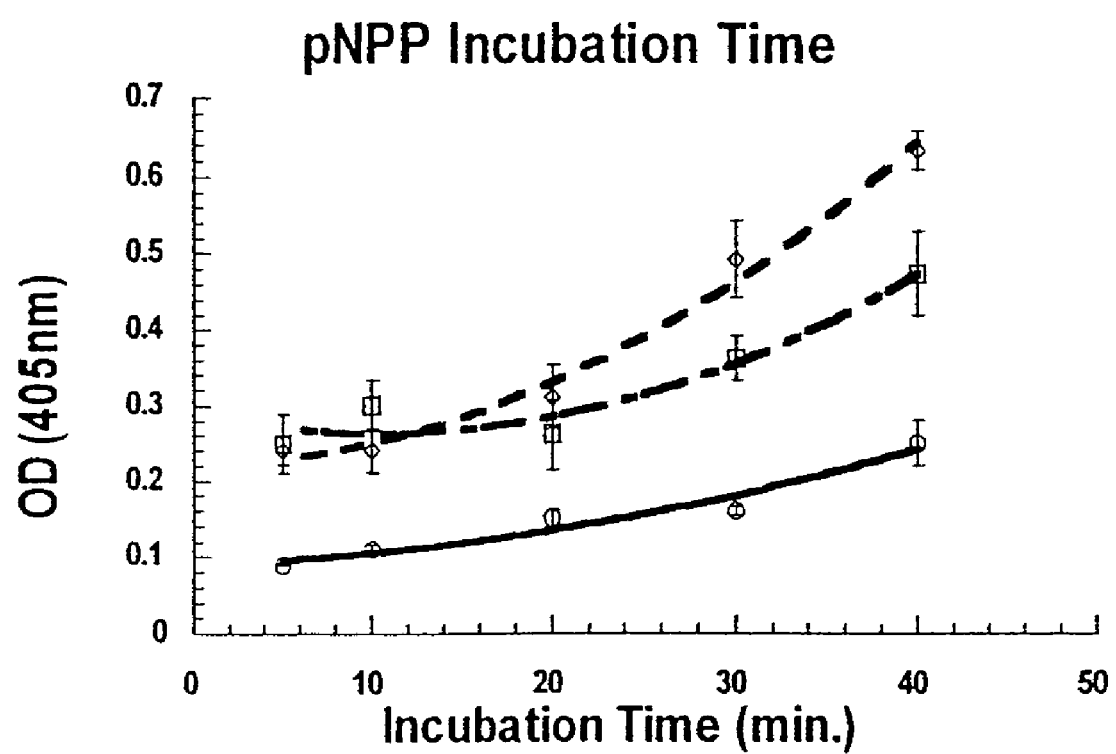

FIG. 16A. Linear relationship between OD (405 nm) and pNPP incubation time. Using 1 embryo/well at 24 (red), 48 (blue) and 72 (green) hpf stage, a linear relationship was observed between 20 and 40 minutes (each point represents mean+S.E., n=6).

FIG. 16B. OD (405 nm) difference among embryos aged 24, 48 and 72 hpf, incubated with pNPP for 5 (red), 10 (blue), 20 (green), 30 (dark green) and 40 (magenta) minutes (each point represents mean+S.E., n=6).

FIG. 17. Representative embryos re-stained for microscopic observation after OD (405 nm) measurement. A. 24 hpf; B. 48 hpf; and C. 72 hpf. The arrows indicate the site of the SIVs formation. At 24 and 48 hpf, the SIVs are not yet present. In contrast, the SIVs are quite obvious by 72 hpf.

Figure 18:
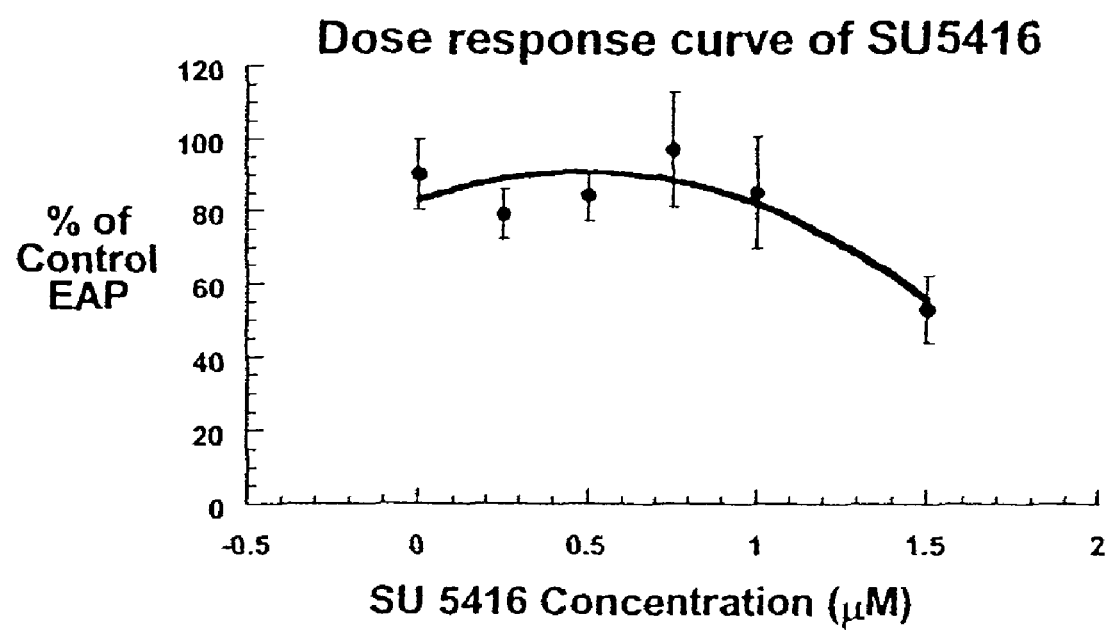

FIG. 18. Dose response curve of SU5416 (each point represents mean+S.E., n=10).

Figure 19:
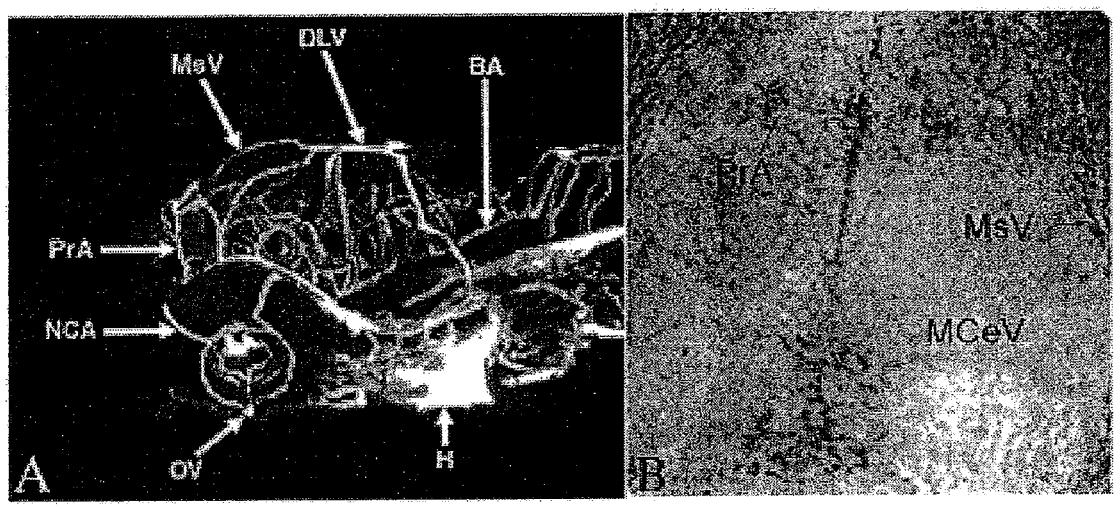

FIG. 19. Presence of extensive vasculature and tight junctions in the brain of zebrafish embryos. A. Microangiography after injecting dextran-rhodamine beads was used to image the entire brain vasculature in 3 day zebrafish embryos: The major brain ventricles are completely formed, angiogenic vessels are well-formed, and the blood vessel network, which transports nutrients and compounds to brain cells, can be visualized in the brain. B. Tight junctions are present during early development. Whole mount ZO-1 antibody immunostaining showed that tight junctions form in the brain (dark spots) adjacent to the mesencephalic vein (MsV), middle cerebral vein (MCeV), and prosencephalic artery (PrA) (arrows). ZO-1 is a tight junction component; mouse monoclonal antibody against rat ZO-1 (Sigma, St. Louis, Mo.) was used in this study. BA: basilar artery; DLV dorsal longitudinal anastomotic vessel; NCA; nasal ciliary artery; OV: optic vein; H: heart.

Figure 20:
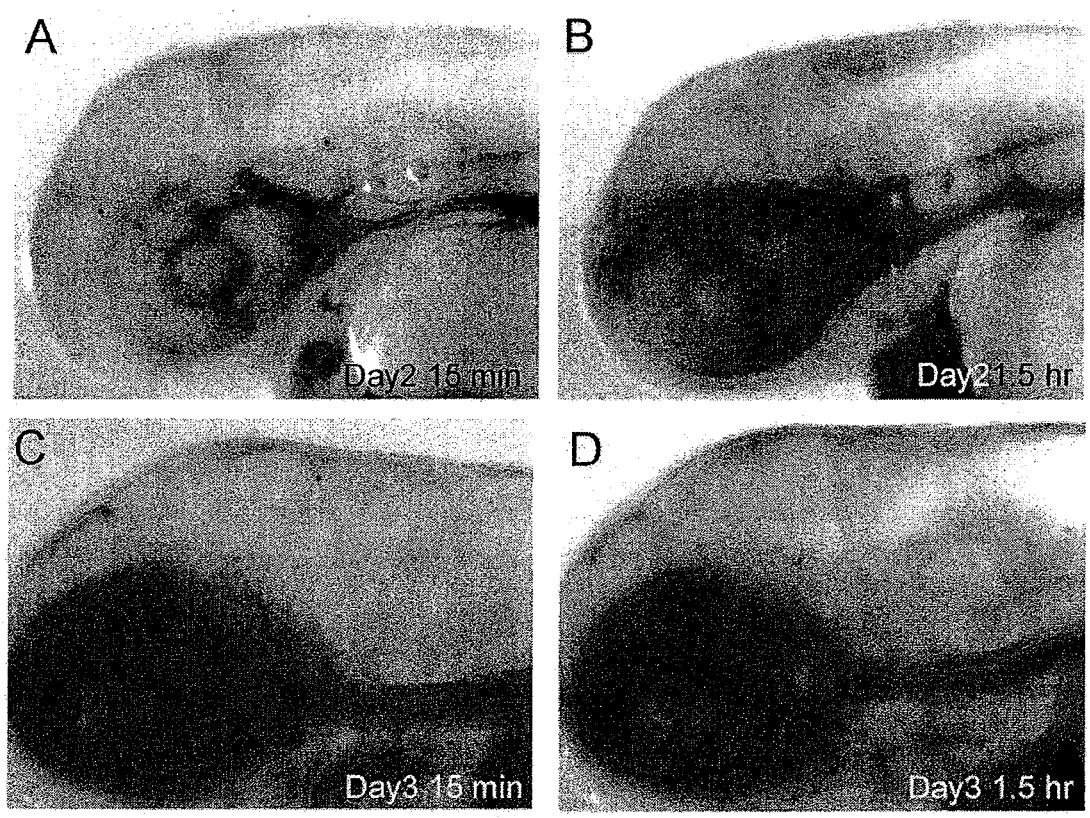

FIG. 20. Representative Evans blue extravasation/exclusion assay. An Evans blue dye injection method was used to confirm the presence of a blood brain barrier (BBB) in zebrafish embryos. Evans blue dye (MW=961 Daltons) was microinjected into the peripheral blood vessels in 2 (A and B) and 3 day (C and D) zebrafish embryos. Distribution of the dye was assessed in the brain at 15 min (A and C) and 1.5 hours (B and D) after microinjection. In 2 day zebrafish embryos, Evans blue dye was observed in the brain blood vessels (arrow) at 15 min (A). However, perfusion of dye to the mid-brain and hind-brain region was observed at 1.5 hours (B). In contrast, in 3 day zebrafish embryos, Evans blue dye was strictly confined in the brain blood vessels and excluded from the brain tissue at both 15 min (C) and 1.5 hours (D) after injection.

Figure 21:
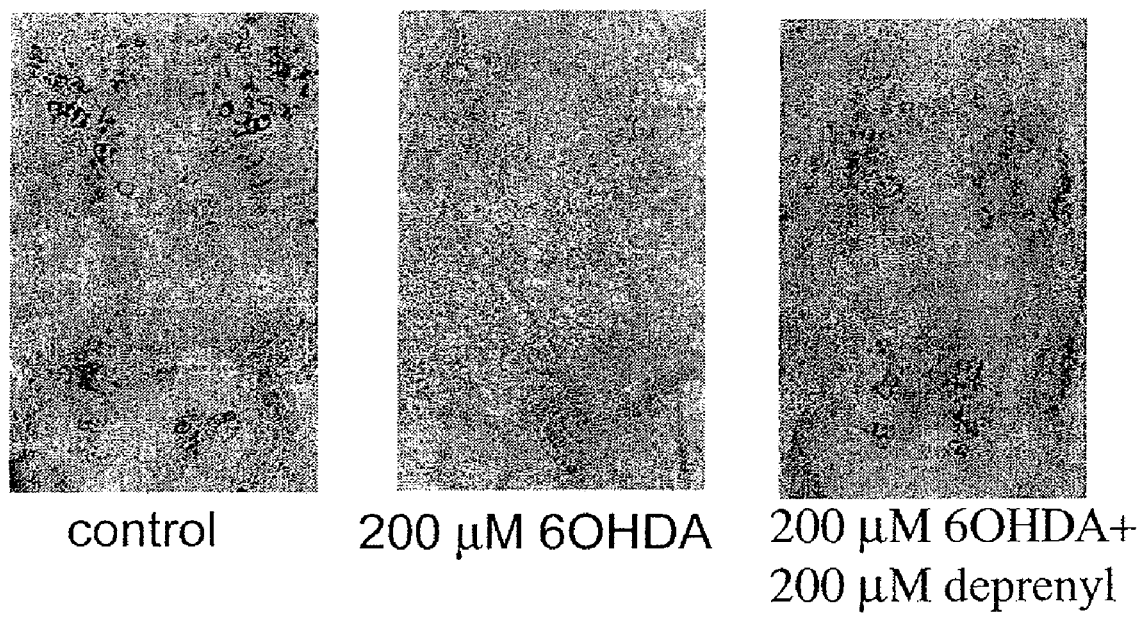

FIG. 21 shows the effect of compounds on dopaminergic neuron activity in zebrafish embryos at 2 days post-fertilization. Zebrafish embryos were treated with 0.1% DMSO (control), 200 μM 6-hydroxydopamine (6OHDA) or 200 μM 6-hydroxydopamine plus 200 μM deprenyl, as indicated, fixed and then immunostained using anti-hydroxylase antibody. 6OHDA induces dopaminergic neuron (DA) loss in diencephalons, mimicking Parkinson's disease. 6OHDA treatment induced DA neuron loss in zebrafish, however, deprenyl treatment prevented 6OHDA-induced DA neuron loss.

Figure 22:
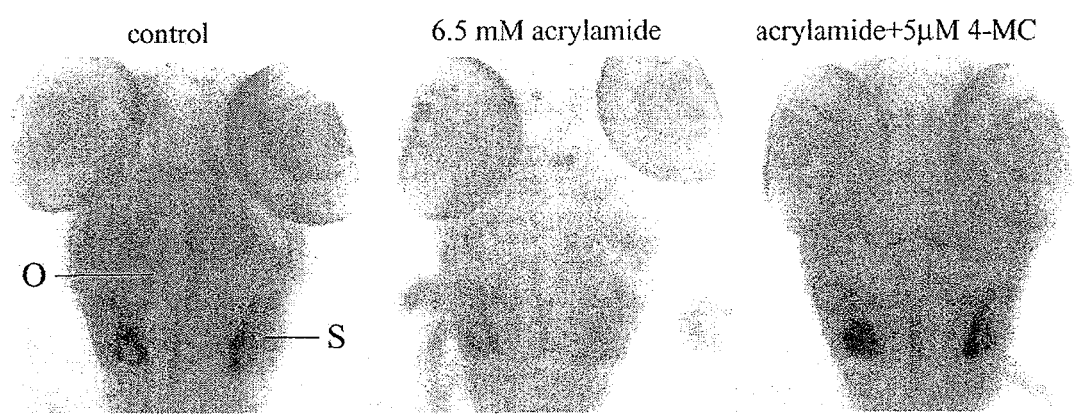

FIG. 22 shows the effect of compounds on the myelin sheath in zebrafish embryos at 4-days post-fertilization. Zebrafish embryos were treated with 0.1% DMSO (control), 6.5 mM acrylamide, or 6.5 mM acrylamide plus 5 μM 4-methylcatechol (4-MC). as indicated. 4-MC is a potent stimulator of nerve growth factor (NGF) synthesis. Integrity of the myelin sheath was detected in the CNS (oligodendrocytes: 0) and in the PNS (Schwann cells: S) by in situ hybridization using riboprobes against myelin basic protein (MBP). Acrylamide decreased expression of MBP in oligodendrocytes and Schwann cells, however, 4-MC rescued the acrylamide-induced loss of MBP.

Figure 23:
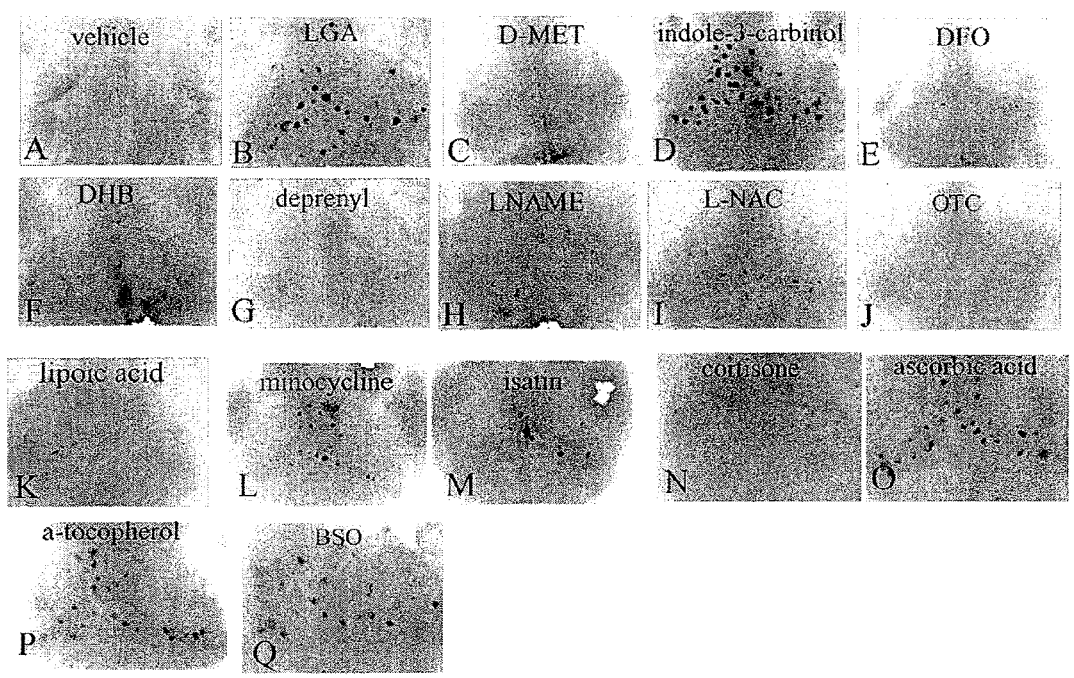

FIG. 23 shows the effect of compounds on oxidation-induced apoptosis in zebrafish embryos at 3 days post-fertilization. Zebrafish embryos were treated with L-hydroxyglutaric acid) (LGA) which caused oxidation and apoptosis in zebrafish. Zebrafish embryos were treated with vehicle alone (A), 50 mM LGA alone (B), or LGA plus D-Met (1 µM) (C), indole-3-carbinol (1 µM) (D), DFO (1 µM) (E), DHB (1 µM) (F), deprenyl (0.1 µM) (G), LNAME (1 µM) (H), L-NAC (5 µM) (I), OTC (10 µM) (J), lipoic acid (10 µM) (K), minocycline (10 µM) (L), isatin (100 µM) (M), cortisone (10 µM) (N), ascorbic acid (100 µM) (O), α-tocopherol (100 µM) (P), and BSO (10 µM) (R), as indicated for 24 hours, then AO staining was used to examine brain apoptosis. All images were focused in the dorsal brain region (anterior on top, posterior on bottom, dorsal on front) and inverted. Apoptotic cells displayed a punctate fluorescent staining pattern (black dots). D-Met, DFO, DHB, deprenyl, L-NAME, L-NAC, OTC, lipoic acid, minocycline, isatin and cortisone exhibited protection, whereas indole-3-carbinol, ascorbic acid and α-tocopherol, and the negative control BSO, exhibited no significant protection, from LGA-induced apoptosis.

Figure 24:
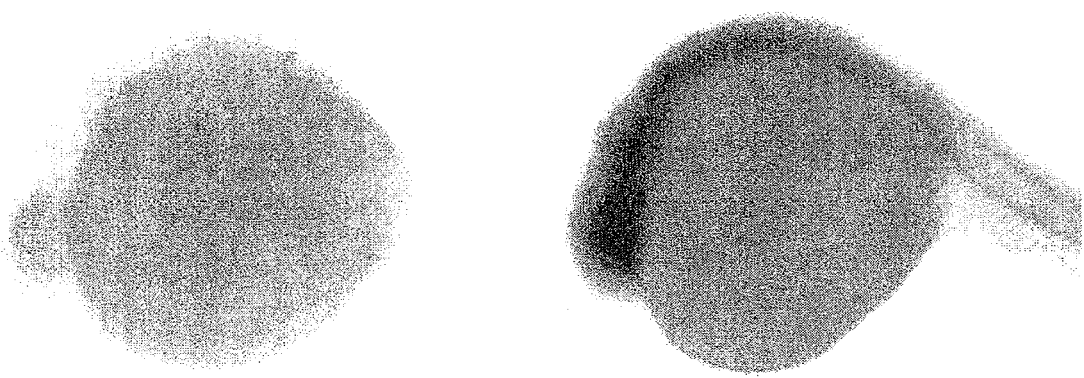

FIG. 24. Expression of the blood brain barrier transporter protein MRP1 in zebrafish embryos. In situ hybridization was performed to examine expression of MRP1 RNA using sense (negative control) and anti-sense riboprobes. The sense RNA probe did not detect any signal (left panel). In contrast, the anti-sense RNA probe detected expression of MRP1 in the brain and spinal cord region at 24 hours (right panel) and in older animals (data not shown) indicating early development of BBB transporters in zebrafish.

FIG. 25. Representative P-glycoprotein (P-gp) efflux assay in zebrafish embryos. 3-day zebrafish embryos were incubated with vehicle alone (A and B) or 30 µM verapamil for 24 hours (C and D). Verapamil is a commonly used P-gp inhibitor in rodent BBB models in vivo. After drug treatment, a zebrafish P-gp efflux assay was performed. FITC-HPR, a fluorescent P-gp substrate, was microinjected into zebrafish embryo brain tissue and monitored for retention of this fluorescent dye. In both controls and verapamil-treated animals, 15 min after injection fluorescent dye was observed in the brain. However, 4 hours after injection, only a small amount of dye was retained in the brain in the control (B). In contrast, verapamil-treated animals exhibited retention of high level of fluorescent dye (D), indicating that the function of P-gp was impaired by the presence of verapamil. Images in A and B, as well as in C and D, are of the same animals at the different time points.

Figure 26:
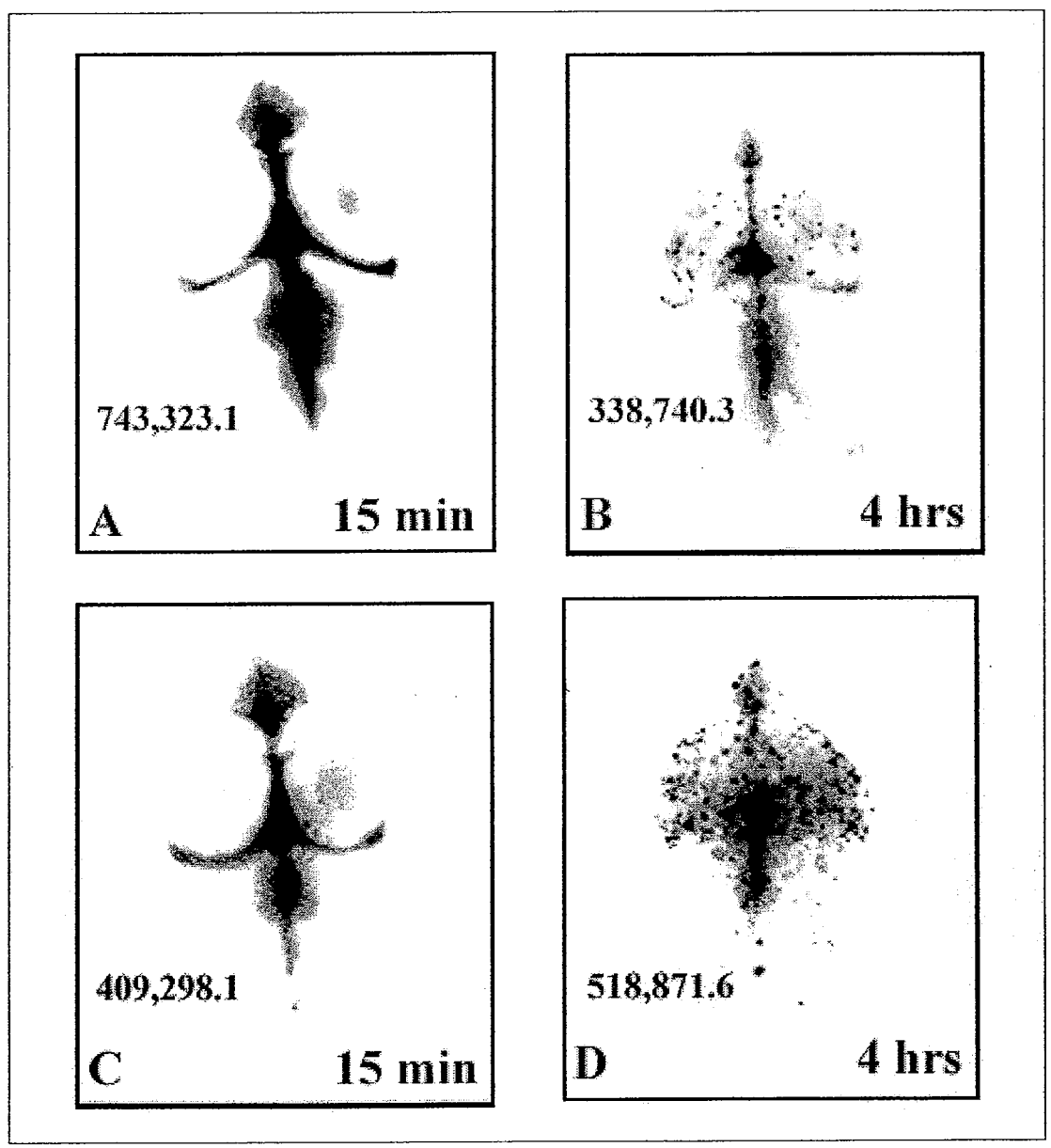

FIG. 26. Representative morphometric analysis of zebrafish embryos. Inverted images from FIG. 25 are shown as an example of morphometric analysis. The fluorescent signals from the brain region are quantified using Scion Image software. Total fluorescence was calculated as the fluorescence intensity×staining area. For control animals, at 15 min after injection the fluorescence intensity was 743,323.1 (A), and at 4 hours after injection, as efflux started, the fluorescence intensity was 338,740.3 (B). For verapamil-treated animals, 4 hours after injection the total fluorescence was 518,871.6 (D), indicating that most of the fluorescence remained in the brain. The fluorescence signal in (D) was higher than (C) because the fluorescent dye was not transported out of the brain. After 4 hours, fluorescent dye diffused to other regions of the brain and increased the stained area.

Figure 27:
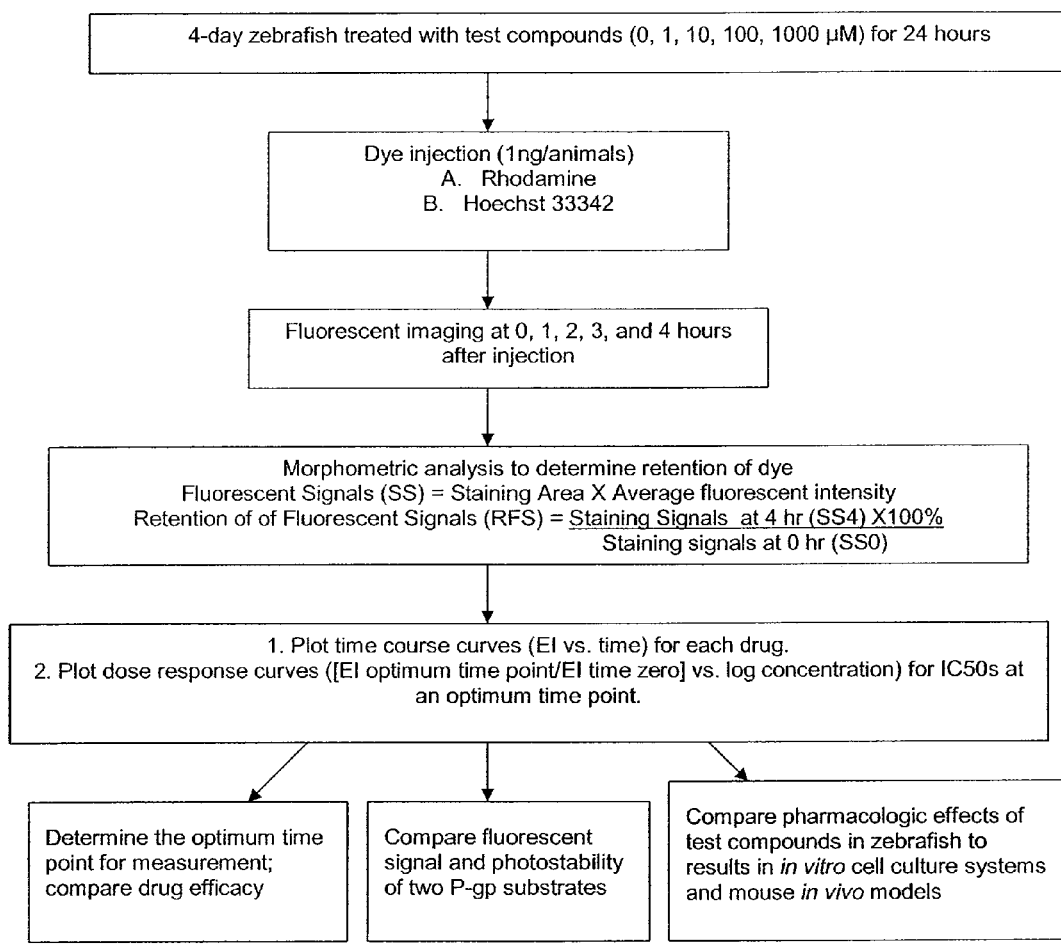

FIG. 27. Flow chart for an exemplary screening method for compounds having an effect on blood brain barrier permeability in zebrafish.

Figure 28:
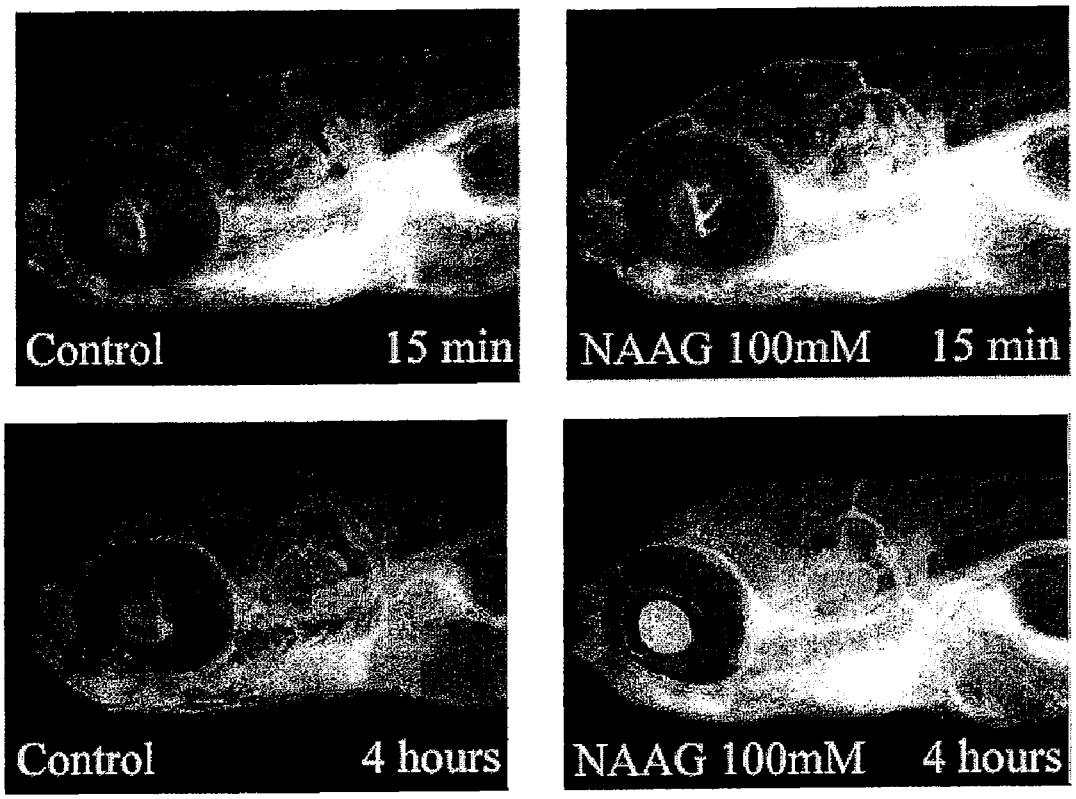

FIG. 28 shows the effect of N-acetyl-L-aspartyl-L-glutamate (NAAG), an agonist at group II metabotropic and NR1/NR2D-containing N-methyl-D-aspartate (NMDA) ionotropic glutamate receptors, on blood brain barrier integrity in zebrafish embryos at 4-day post-fertilization. In controls (left panels), Rhodamine 123 was observed in the blood vessels at 15 and 4 hours after injection. In NAAG-treated zebrafish, Rhodamine 123 was observed in the brain tissue 4 hours after injection, indicating increased BBB permeability.

DEFINITIONS

Unless defined otherwise, all technical and scientific terms used herein have the same meaning as commonly understood by those of ordinary skill in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991). As used herein, the following terms and phrases have the meanings ascribed to them unless specified otherwise. Although any methods and materials similar or equivalent to those described herein can be used in the practice or testing of the present invention, the preferred methods and materials are described. For purposes of the present invention, the following terms and phrases are intended to have the following general meanings as they are used herein:

The term "subject" as used herein includes an animal. The term "animal" as used herein includes a vertebrate animal, such as a vertebrate fish. Vertebrate fish include teleosts, such as, e.g., zebrafish, medaka, Giant rerio, and puffer fish. The term "teleost" as used herein means of or belonging to the Teleostei or Teleostomi, a group consisting of numerous fishes having bony skeletons and rayed fins. Teleosts include, for example, zebrafish, medaka, Giant rerio, and puffer fish.

The term "larva" or "larval" as used herein means the stage of any of various animals, including vertebrate animals, such as vertebrate fishes (including teleosts, such as, e.g., zebrafish, medaka, Giant rerio, and puffer fish), between embryogenesis and adult.

"Angiogenesis activity" or "angiogenic activity" in reference to an agent is defined herein as the ability of the agent to enhance, inhibit, or prevent the formation or outgrowth of blood vessels or lymph vessels. Angiogenesis activity or angiogenic activity in reference to a subject refers to activity associated with angiogenesis within a subject or organ(s) or tissue(s) of a subject or originating from within a subject or organ(s) or tissues(s) of the subject.

"Anti-angiogenesis activity" or "anti-angiogenic activity" in reference to an agent is defined herein as the ability of the agent to inhibit, prevent, or greatly reduce the formation or outgrowth of blood or lymph vessels, or destroy such vessels during sprouting or outgrowth. Anti-angiogenesis activity or anti-angiogenic activity in reference to a subject refers to activity associated with anti-angiogenesis within a subject or organ(s) or tissue(s) of a subject or originating from within a subject or organ(s) or tissues(s) of the subject.

The term "apoptotic activity" or "apoptosis activity" in reference to an agent is defined herein as the ability of the agent to enhance, inhibit, or prevent apoptosis. Apoptotic activity or apoptosis activity in reference to a subject refers to activity associated with the death of cells within a subject or organ(s) or tissue(s) of a subject or originating from within a subject or organ(s) or tissues(s) of the subject.

"Cell death activity" in reference to an agent is defined herein as the ability of the agent to enhance, inhibit, or prevent the death of one or more cells within a subject or organ(s) or tissue(s) of a subject or originating from within a subject or organ(s) or tissues(s) of the subject. Cell death activity in reference to a subject refers to activity associated with the death of cells within a subject or organ(s) or tissue(s) of a subject or originating from within a subject or organ(s) or tissues(s) of the subject.

The term "necrotic activity" or "necrosis activity" in reference to an agent is defined herein as the ability of the agent to enhance, inhibit, or prevent necrosis.

An "effect on cell death activity" as used herein refers to the way in which an agent acts upon or influences cell death activity in a subject. Such effects include an ability to enhance or inhibit cell death activity in the subject, as indicated or manifested by, for example, a clinical manifestation, characteristic, symptom, or event that occurs or is observed in, associated with, or peculiar to death of cells in a subject.

An "effect on apoptotic activity" as used herein refers to the way in which an agent acts upon or influences apoptotic activity in a subject. Such effects include an ability to enhance or inhibit apoptotic activity in the subject, as indicated or manifested by, for example, a clinical manifestation, characteristic, symptom, or event that occurs or is observed in, associated with, or peculiar to apoptosis of cells in a subject.

An "endogenously occurring" as used herein means occurring originating from within.

The term "gene" is used broadly to refer to any segment of DNA associated with a biological function. Thus, genes include coding sequences and/or the regulatory sequences required for their expression. Genes also include non-expressed DNA segments that, for example, form recognition sequences for other proteins.

The term "nucleic acid" or "nucleic acid segment" refers to a deoxyribonucleotide or ribonucleotide and polymer thereof which is in either single- or double-stranded form. Unless specifically limited, the term encompasses nucleic acids containing known analogues (synthetic and naturally occurring) of nucleotides, which have similar binding properties as the reference nucleic acid and are metabolized in a manner similar to the reference nucleotides. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions can be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, and mRNA encoded by a gene.

The term "isolated nucleic acid" or "isolated nucleic acid segment" means a single- or double-stranded nucleic acid (e.g., an RNA, DNA, or a mixed polymer), which is substantially separated from other genome DNA sequences as well as proteins or complexes such as ribosomes and polymerases, which naturally accompany a native sequence. The term embraces a nucleic acid sequence which has been removed from its naturally occurring environment, and includes recombinant or cloned DNA isolates and chemically synthesized analogues or analogues biologically synthesized by heterologous systems. A substantially pure molecule includes isolated forms of the molecule. An "isolated polypeptide" or protein carries a similar meaning with the polypeptide or protein being substantially separated from any cellular contaminants and components naturally associated with the protein in vivo.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

A "chimeric molecule" as used herein refers to a linked molecule obtained after conjugation of two or more different types of molecules (e.g., lipids, glycolipids, peptides, proteins, glycoproteins, carbohydrates, nucleic acids, natural products, synthetic compounds, organic molecule, inorganic molecule, etc.).

The term "normal blood vessel formation" as used herein refers to the typical, usual, or natural process of forming or producing blood vessels in a subject.

The term "gene expression profile" or "gene expression pattern" as used herein means a profile or pattern based on the detection of mRNA for each gene to be included in the profile or pattern. mRNA can be detected at a particular time or under a particular condition(s). mRNA is extracted from cells, tissues, organs, or an entire organism of interest and detected. The amount or level of mRNA for a particular gene can be determined quantitatively.

The term "protein expression profile" or "protein expression pattern" as used herein means a profile or pattern based on the detection of a protein. The protein can be detected at a particular time or under a particular condition(s). Protein is extracted from cells, tissues, organs, or an entire organism of interest and detected. The amount or level of protein can be determined quantitatively.

The term "agent" includes any element, compound, or entity, including, but not limited to, e.g., pharmaceutical, therapeutic, pharmacologic, environmental or agricultural pollutant or compound, aquatic pollutant, cosmeceutical, drug, toxin, natural product, synthetic compound, or chemical compound.

The term "natural compound" as used herein includes a molecule isolated, extracted, or purified from a plant, animal, yeast, bacterium, or other microorganism. A natural compound includes, e.g., among other things, organic molecules belonging to the broad biochemical classes of peptides, proteins, glycoproteins, nucleic acids, carbohydrates, lipids, fats, glycolipids, as well as more complex molecules which comprise, e.g., elements of more than one of these basic biochemical classes.

The term "synthetic compound" as used herein includes a molecule synthesized de novo or produced by modifying or derivatizing a natural compound.

"Developmental defect" as used herein means a deficiency, imperfection, or difference in the development of a tissue, organ, or other bodily component of an animal relative to normal development. Such a defect is identified as a change, difference, or lack of something necessary or desirable for completion or proper operation in the development of a tissue, organ, or other bodily component of the animal as compared with normal development of the component. Developmental defects include, for example, the failure of organ to develop properly, excess or reduced cell proliferation as compared to normal cell proliferation, and the malfunctioning of an organ or tissue.

Generally, the nomenclature used hereafter and the laboratory procedures in cell culture, molecular genetics, and nucleic acid chemistry described below are those well known and commonly employed in the art. Standard techniques such as described in Sambrook et al., MOLECULAR CLONING: A LABORATORY MANUAL (Cold Spring Harbor Laboratory, Cold Spring Harbor, N.Y., 2nd ed. 1989) and CURRENT PROTOCOLS IN MOLECULAR BIOLOGY, Vols. 1-3 (Virginia Benson Chanda ed., John Wiley & Sons, 1994-1998), each of which is incorporated herein by reference in its entirety for all purposes, are used for recombinant nucleic acid methods, nucleic acid synthesis, cell culture, and transgene incorporation, e.g., electroporation, injection, ingestion, and lipofection. Electroporation techniques utilize a pulse of high electrical current to introduce molecules of interest into cells, tissues, or organisms. Lipofection employs lipid-like cationic molecules that interact strongly with cell membranes, destabilizing them locally, thereby allowing DNA and RNA entry into cells. Generally, oligonucleotide synthesis and purification steps are performed according to the specifications. The techniques and procedures are generally performed according to conventional methods in the art and various general references which are provided throughout this document. The procedures therein are believed to be well known in the art and are provided for the convenience of the reader.

The term "transgenic" in reference to an organism or animal includes those organisms or animals that have developed from a fertilized egg, into a chromosome of which a foreign gene has been inserted. Such transgenic organisms and animals carry the foreign gene insert in every cell. Transgenic organisms and animals are created by using known techniques (see, e.g., Sambrook, supra and BIOCHEMISTRY WITH CLINICAL CORRELATIONS (T. Devlin ed., 3d ed. 1992), which is incorporated herein by reference in its entirety for all purposes). Transgenic organisms and animals can be used to study different aspects of the foreign gene, including the analysis of DNA regulatory elements, expression of proteins during differentiation, tissue specificity, and the potential role of oncogene products on growth, differentiation, and the induction of tumorigenesis. A "transgene" is a gene, in original or modified form, that has been introduced into an organism or animal that does not naturally have such gene. A "mosaically expressing transgene" is a transgene that is expressed randomly in a subset of the cells of the transgenic organism or animal. An "exogenous gene" is a gene from an organism or animal that does not belong to the species into which the gene has been introduced. A "transient transgenic animal" is transgenic animal which carries an introduced gene that is not inserted into a chromosome.

The term "founder fish" as used herein refers to the fish from which a line of fish is generated. Usually, a founder fish is an individual fish which carries a unique mutation and which is used to generate progeny that also carry the mutation.

A "physiological activity" in reference to an organism is defined herein as any normal processes, functions, or activities of a living organism.

A "prophylactic activity" is an activity of, for example, an agent, gene, nucleic acid segment, pharmaceutical, substance, compound, or composition which, when administered to a subject who does not exhibit signs or symptoms of a disease or exhibits only early signs or symptoms of a disease, diminishes, decreases, or prevents the risk in the subject of developing pathology.

A "therapeutic activity" is defined herein as any activity of e.g., an agent, gene, nucleic acid segment, pharmaceutical, therapeutic, substance, compound, or composition, which diminishes or eliminates pathological signs or symptoms when administered to a subject exhibiting the pathology. The term "therapeutically useful" in reference to an agent means that the agent is useful in diminishing, decreasing, treating, or eliminating pathological signs or symptoms of a pathology or disease.

DESCRIPTION OF THE SPECIFIC EMBODIMENTS

I. General

The present invention is directed to methods of screening an agent for an activity. In Section II of the application, methods of screening an agent for an ability or capacity to enhance, inhibit, or block angiogenesis activity are discussed. In Section III, methods of screening an agent for an ability to enhance, inhibit, or cause cell death activity are described. In Section IV, methods of screening an agent for a toxic activity are presented. In Section V, high throughput screening methods are described. In Section VI, methods of screening an agent for an activity in the brain or central nervous system are described.

A. Animal Models

The methods of the present invention, which are directed to screening agents for activities (e.g., angiogenesis activity, cell death activity, and toxic activity), are generally applicable for use in a various animals, including vertebrate animals, such as fish. Various species of fish are suitable, including teleosts. Suitable teleosts include, for example, zebrafish (*Danio rerio*), Medaka, Giant rerio, and puffer fish. Typically, animal models of the present invention are fish that are transparent or translucent (i.e., optically clear) in at least one of the following stages: the embryonic, larval, or adult stage.

Certain teleosts, including the zebrafish, Medaka, Giant rerio, and puffer fish, offer important advantages over other animal model systems for use in screening methods of the present invention. First, these teleosts are vertebrates whose genetic makeup is more closely related to that of man than are other models, such as the *Drosophila* and nematode. All essential components of human form and organ development are mimicked in these teleosts and the morphological and molecular bases of tissue and organ development are either identical or similar to other vertebrates, including man. Chen and Fishman, *Development* 123:293-302 (1996); Granato and Nusselien-Volhard, *Cur. Op. Gen. Dev.* 6:461-468 (Wylie ed. 1996). As a result, these teleosts serve as an excellent model for the study of vertebrate development and human disease states.

Second, these teleosts provide advantageous animal models because their embryos are very transparent. Given the transparency of the embryo, angiogenesis activity, cell death activity (e.g., apoptosis and necrosis), and toxic activity produced by administered agents can be detected and diagnosed much more rapidly than in non-transparent animals. These activities can also be detected in the more mature larval and adult forms of the zebrafish, though somewhat less readily as such forms become progressively less optically clear. These activities can also be detected in vivo in all three forms or in cells thereof in vitro. By contrast, the mouse, which is commonly used as an animal model system, is an opaque animal and does not allow a similar rapid or in vivo assessment of phenotypic or developmental changes, including those associated with cell death, angiogenesis, or toxicity, in whole animal or whole organs or tissues. Significantly, precursor tissues and components of the brain, eyes, heart, and musculature of these teleosts are detected and visualized much more easily and quickly in the transparent teleosts than in other systems, including other vertebrate systems (such as the mouse) by a variety of detection techniques, including, e.g., light microscopy, fluorescence microscopy, colorimetry, chemiluminescence, digital imaging, microplate reader techniques, in situ hybridization of RNA, etc.

Another important advantage of teleosts over other animal models is that teleosts develop much more rapidly than do other animal models. In general, the body plan, organs, tissues, and other systems of teleosts develop much more rapidly than do such components in other vertebrate model systems (e.g., the mouse). The entire vertebrate body plan of the zebrafish, for example, is typically established within 24 hours. A functioning cardiovascular system is evident in the zebrafish within the first 24 hours of development. Stainier and Fishman, *Trends Cardiovasc. Med.* 4:207-212 (1994). The remaining organs of the zebrafish, including the gut, liver, kidney, and vasculature, are established within 48 hours. The hatched zebrafish embryo nearly completes morphogenesis within 120 hours, thereby making it highly accessible to manipulation and observation and amenable to high-throughput automated observation and detection procedures.

The cell death activity, angiogenesis activity, and toxic activity of an agent and responses indicating these activities can be monitored in whole teleosts and/or in vivo or in cells thereof in vitro over time—a procedure not possible or readily practiced with other animal embryos which develop in utero, such as the mouse. Moreover, the effects of an agent on the whole teleost embryo or on more than one system (e.g., cardiovascular system, enteric system, and musculature system), organ, or tissue can be detected simultaneously using transparent teleosts. The persistence of such effects can be monitored by using simple visualization methods and over selected time intervals. By comparison, it is extremely difficult to detect and assess developmental and phenotypic changes in organs, tissues, and systems (such as inhibition or enhancement of angiogenesis, cell death or toxic activity due to an agent) over time in animals which develop in utero. Mouse embryos, for example, must be removed from the mother—a labor intensive procedure—before an assay can be performed.

Teleosts also offer the advantage that agents to be evaluated for toxic effects can be administered directly to the developing teleost. Direct introduction of candidate compounds is hindered in animals which develop in utero, such as the mouse embryo. Further, the teleost embryo is an intact, self-sustaining organism. It is different from a mouse embryo, for example, which because it is physically removed from its mother's womb, it is not self-sustaining or intact; a mouse embryo would function more as an "organ" culture or the like.

Another significant advantage is cost. Mouse assays are expensive, primarily due to the cost of breeding and maintenance and the need to manually perform injections and subsequent analysis. The average cost of a commercial mouse tumor assay is approximately $2,900 ($1,600 per government). In contrast, teleosts, such as zebrafish, are comparatively inexpensive to generate and maintain. For example, the estimate cost of a zebrafish assays is less than $100. A single mating of a zebrafish produces 100-200 eggs. Inbred strains are available and thousands of zebrafish can be raised inexpensively in a small room of aquaria. Moreover, teleost eggs, including those of the zebrafish, are externally fertilized. Teleost embryos (such as zebrafish) can survive by diffusion of oxygen from the water and nutrients from the yolk and thus even the absence of the entire circulatory system is well tolerated during early development. Weinstein et al., *Nature Med.* 1:1143-1147 (1995).

Additionally, single whole teleost embryos can be maintained in vivo in fluid volumes as small as 100 microliters for the first six days of development. Intact live embryos can be kept in culture in individual microtiter wells or multi-well plates. Test compounds can be added directly to the solution in which the fish is immersed. Compounds permeate the intact embryo directly, making this multi-well format particularly attractive for high through-put and automated compound screening. Both the therapeutic activities and side effects (e.g., toxicity) of a drug can be assayed in the fish simultaneously in vivo.

The teleosts used with the screening methods of the invention are typically early-stage teleost embryos; however, transparent larval or adult teleosts can also be used. Wildtype strains of teleosts are usually employed. Wildtype strains are typically maintained for about one year, after which time fertility decreases. Mutant strains of teleosts (such as zebrafish) can be used to assess, e.g., the interaction between therapeutic agents and specific genetic deficiencies. The teleost can contain a mutation in a selected gene. The mutation can be a heritable mutation, including, e.g., a heritable mutation associated with a developmental defect. The teleost can also be transgenic.

B. Agents to be Screened

A variety of agents from various sources can be screened for enhancing or inhibiting angiogenesis activity, cell death activity, and/or toxic activity by using the methods of the present invention. Agents to be screened can be naturally occurring or synthetic molecules. Agents to be screened can also obtained from natural sources, such as, e.g., marine microorganisms, algae, plants, fungi, etc. Alternatively, agent to be screened can be from combinatorial libraries of agents, including peptides or small molecules, or from existing repertories of chemical compounds synthesized in industry, e.g., by the chemical, pharmaceutical, environmental, agricultural, marine, cosmeceutical, drug, and biotechnological industries. Agents can include, e.g., pharmaceuticals, therapeutics, environmental, agricultural, or industrial agents, pollutants, cosmeceuticals, drugs, organic compounds, lipids, glucocorticoids, antibiotics, peptides, proteins, sugars, carbohydrates, chimeric molecules, etc.

Combinatorial libraries can be produced for many types of compounds that can be synthesized in a step-by-step fashion. Such compounds include polypeptides, proteins, nucleic acids, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of compounds can be constructed by the encoded synthetic libraries (ESL) method described in Affymax, WO 95/12608, Affymax WO 93/06121, Columbia University, WO 94/08051, Pharmacopeia, WO 95/35503 and Scripps, WO 95/30642 (each of which is incorporated herein by reference in its entirety for all purposes). Peptide libraries can also be generated by phage display methods. See, e.g., Devlin, WO 91/18980. Compounds to be screened can also be obtained from governmental or private sources, including, e.g., the National Cancer Institute's (NCI) Natural Product Repository, Bethesda, Md., the NCI Open Synthetic Compound Collection, Bethesda, Md., NCI's Developmental Therapeutics Program, or the like.

C. Administration of Agents

Agents to be screened for an effect on angiogenesis activity, cell death activity, and/or toxic activity can be administered to the teleost by adding the agent directly to the media containing the live teleost. Alternatively, the agent can first be dissolved in the media and the live teleost submerged in the media subsequently. Such approaches have been used to introduce anesthetics and other chemicals to fish embryos. See, e.g., M. Westerfield, THE ZEBRAFISH BOOK: A GUIDE FOR THE LABORATORY USE OF ZEBRAFISH (3d. ed. 1995), which is incorporated herein in its entirety for all purposes. Agents can also be administered to the teleost by using microinjection techniques in which the agent is injected directly into the live teleost. For example, agents can be injected into either the yolk or body of a teleost embryo or both.

Agents can also be administered to teleosts by electroporation, lipofection, or ingestion or by using biolistic cell loading technology in which particles coated with the biological molecule are "biolistically" shot into the cell or tissue of interest using a high-pressure gun. Such techniques are well known to those of ordinary skill in the art. See, e.g., Sambrook et al., supra; Chow et al., *Amer. J. Pathol.* 2 (6):1667-1679 (1998).

Agents can be administered alone, in conjunction with a variety of solvents (e.g., dimethylsulfoxide or the like) or carriers (including, e.g., peptide, lipid or solvent carriers), or in conjunction with other compounds.

Agents can be administered to the teleost before, at the same time as, or after administration of a dye used for detection of the response in the animal indicating a specific activity (e.g., cell death activity, angiogenesis activity, toxic activity).

D. Administration of Dyes

A dye used in methods of screening agents for an activity (e.g., cell death activity, angiogenesis activity, toxic activity) can be administered to the teleost by adding the agent directly to the media containing the live teleost. Alternatively, the dye can first be dissolved in the media and the live teleost submerged in the media subsequently. See, e.g., Westerfield, supra. Dyes can also be administered to the teleost by using microinjection techniques in which the dye is injected directly into the live teleost. Dyes can be injected into either the yolk or body of a teleost embryo or both.

Dyes can be administered alone, in conjunction with a variety of solvents (e.g., dimethylsulfoxide or the like), or in conjunction with other dyes. Dyes can be administered to the teleost before, at the same time as, or after administration of a dye used for detection of the response in the teleost indicating a specific activity (e.g., cell death activity, angiogenesis activity, toxic activity). When fluorescent dyes are used (e.g., unsymmetrical cyanine dye, such as a quinolium dye) for detection of an activity (e.g., cell death activity), the dye is preferably administered prior to administration of the agent.

E. Detecting Agent Activity and Responses in Teleosts

A variety of techniques can be used together or separately to generate a signal and to detect and assess the effect of an agent on cell death activity or angiogenesis activity or toxic activity of an agent. Signals can be generated by, for example, in situ hybridization, antibody staining of specific proteins (e.g., antibody markers that label signaling proteins involved in angiogenic vessel formation in teleost, including VEGF and Ang1 and 2; terminal deoxyuridine nucleotide end labeling to detect dead or dying cells, etc.). Responses indicating toxic or angiogenic activity or an effect of cell death activity can be detected by, e.g., visual inspection, colorimetry, fluorescence microscopy, light microscopy, chemiluminescence, digital image analyzing, standard microplate reader techniques, fluorometry, including time-resolved fluorometry, visual inspection, CCD cameras, video cameras, photographic film, or the use of current instrumentation such as laser scanning devices, fluorometers, photodiodes, quantum counters, plate readers, epifluorescence microscopes, scanning microscopes, confocal microscopes, flow cytometers, capillary electrophoresis detectors, or by means for amplifying the signal such as a photomultiplier tube, etc. Responses can be discriminated and/or analyzed by using pattern recognition software. Agents are identified and selected using the screening methods according to the activities and responses they produce.

Changes in the distribution of a protein both spatially and temporally, including a complete absence of a protein, can be detected and protein expression profiles can be generated. Changes in a level of an enzyme or enzymatic activity within the intact teleost can also be detected by various means, including, e.g., alkaline phosphatase staining and use of streptavidin (avidin) conjugated reporter enzyme to detect naturally biotinylated carboxylase enzymes in the liver, gut, and digestive tube of animals.

F. Automated Methods

In addition to manual screening methods, the present invention also provides methods for rapid screening of agents for activities, such as angiogenesis activity, cell death activity, and toxic activity, using automated procedures. Such automated methods can be readily performed by using commercially available automated instrumentation and software and known automated observation and detection procedures. Multi-well formats are particularly attractive for high through-put and automated compound screening. Screening methods can be performed, for example, using a standard microplate well format, with a whole zebrafish embryo in each well of the microplate. This format permits screening assays to be automated using standard microplate procedures and microplate readers to detect enhancement or inhibition of angiogenesis activity in the zebrafish embryos in the wells. A microplate reader includes any device that is able to read a signal from a microplate (e.g., 96-well plate), including fluorometry (standard or time-resolved), luminometry, or photometry in either endpoint or kinetic assays. Using such techniques, the effect of a specific agent on a large number of teleosts (e.g., teleost embryos) in vivo or in vitro can be ascertained rapidly. In addition, with such an arrangement, a wide variety of agents can be rapidly and efficiently screened for their respective effects on the cells of teleosts contained in the wells.

Sample handling and detection procedures can be automated using commercially available instrumentation and software systems for rapid reproducible application of dyes and agents, fluid changing, and automated screening of target compounds. To increase the throughput of a compound administration, currently available robotic systems (e.g., the BioRobot 9600 from Qiagen, the Zymate from Zymark or the Biomek from Beckman Instruments)—most of which use the multi-well culture plate format—can be used. The processing procedure involves a large number of fluid changes that must be performed at defined timepoints. Non-automated throughput is typically 5 microtiter plates per investigator (400 teleost embryos and 20 compounds) per week based on using a 96-well plate with 1 embryo per well and screening 2 concentrations with 10 embryos per concentration. Using currently available fluid handling hardware (e.g., Bodhan Automation, Inc., Zymark) and our standard sample handling procedures, 50-100 plates per day (4800-9600 teleost embryos and 200-400 compounds) can be processed. Incorporation of commercially available fluid handling instrumentation significantly reduces the time frame of manual screening procedures and permits efficient analysis of many agents, including libraries of agents.

II. Methods of Screening an Agent for an Effect on Angiogenesis Activity

A. Angiogenesis

The formation and establishment of a vascular supply is an essential requirement for the cellular inflow of nutrients, outflow of waste products, and gas exchange in most tissues and organs. Two processes for such blood vessel development and differentiation have been identified. One process of vascularization, termed "vasculogenesis," occurs in the embryo and consists of the in situ differentiation of mesenchymal cells into hemoangioblasts. Hemoangioblasts are the precursors of both endothelial cells and blood cells. The second process, termed "angiogenesis," involves the formation of new blood and lymph vessels from preexisting endothelium. In this process, tissues and organs are vascularized by sprouting in which smaller vessels extend from larger vessels and penetrate a specific tissue. Fouquet et al., supra. Angiogenesis also involves the migration and proliferation of endothelial cells, their differentiation into a tube-like structure, and the production of a basement membrane matrix around the vessel. Herbert et al., *L. Cell. Biol.* 106:1365-1373 (1988).

Methods for screening agents for inhibition or enhancement of angiogenesis activity are useful in identifying agents that would be effective in therapeutic or prophylactic treatment of a variety of diseases involving angiogenic processes.

B. Blood Vessel Formation

New blood vessels form during normal tissue growth and repair in a series of sequential steps: an endothelial cell which forms the wall of an existing small blood vessel (capillary) becomes activated, secretes enzymes that degrade the extracellular matrix (the surrounding) tissue, invades the matrix, and begins dividing. Eventually, strings of new endothelial cells organize into hollow tubes, creating new networks of blood vessels that make tissue and repair possible. Ordinarily, endothelial cells lie dormant. However, when necessary, short bursts of blood vessel growth occur in localized parts of tissues. New capillary growth is tightly controlled by a finely tuned balance between factors that activate or inhibit endothelial cell growth. About 15 proteins are known to activate endothelial cell growth and movement, including angiopoietins, epidermal growth factor, estrogen, fibroblast growth factors, prostaglandin, tumor necrosis factor, vascular endothelial growth factor (VEGF), and granulocyte stimulating factor (Zetter, *Ann. Rev. Med.* 49:407-424 (1998)). VEGF binds to tyrosine kinase receptors flt-1 and flk-1/KDR on endothelial cells (Hanahan, *Science* 277 (5322):48-50 (1997)). Downstream effects of VEGF include the activation of matrix proteases and glucaronidases, loosening of endothelial cell junctions and proliferation and migration of endothelial cells. Downstream effects of basic fibroblast growth factor (bFGF) include the mitogenic stimulation of endothelial cells (Relou et al., *Tissue Cell* 5:525-530 (1998)). Some of the known inhibitors of angiogenesis include angiostatin, endostatin, interferons, interleukin 1, interleukin 12, retinoic acid, and tissue inhibitors of metalloproteinase 1 and 2 (Zetter, supra).

C. Angiogenesis Inhibition

Because angiogenesis is essential for solid tumor growth, inhibition of angiogenesis is one strategy for preventing tumor growth. By blocking the development of new blood vessels, a tumor's supply of oxygen and nutrients can be cut off and, therefore, the tumors' continued growth and metastasis can be arrested. Several strategies can be to design anti-angiogenesis agents including: 1) blocking the factors that stimulate the formation of blood vessels; 2) using natural inhibitors of angiogenesis; 3) blocking molecules that allow newly forming blood vessels to invade surrounding tissue; and 4) incapacitating newly dividing endothelial cells. In general, tumors with higher densities of blood vessels are more likely to metastasize and are correlated with poor clinical outcomes. Also, cell shedding from the primary tumor begins only after the tumor has a full network of blood vessels. In addition, both angiogenesis and metastasis require matrix metalloproteinases, enzymes that break down the surrounding tissue and the extracellular matrix during blood vessel and tumor invasion. Several differences between standard chemotherapy and anti-angiogenesis therapy result from the fact that angiogenic inhibitors target dividing endothelial cells rather than tumor cells. Anti-angiogenic drugs are not likely to cause bone marrow suppression, gastrointestinal symptoms, or hair loss, characteristics of standard chemotherapy treatments. Also, because anti-angiogenic drugs may not necessarily kill tumors, but rather hold them in check indefinitely, the endpoint of early clinical trials may be different than for standard therapies. Rather than looking only for tumor response, it may be appropriate to evaluate increases in survival and or time to disease progression.

Drug resistance is a major problem with chemotherapy agents because most cancer cells are genetically unstable and therefore prone to mutations. Because angiogenic drugs target normal endothelial cells, which are not genetically unstable, drug resistance may not develop. So far, resistance has not been a major problem in long term animal studies or in clinical trials of potential therapeutic drug candidates. Anti-angiogenic therapy may prove useful in combination with therapy directly aimed at tumor cells. Because each therapy is aimed at different cellular targets, such combination therapy should more effective. There is growing recognition that cancer may become a chronic disease. If treatments are long term, the toxicity profile of drugs, which can be examined readily in the transparent teleost (e.g., zebrafish) embryo, will become an increasingly important parameter for drug screening and evaluation.

D. Angiogenesis Stimulation

Although ischemic tissue in the heart or limbs secretes VEGF and bFGF, which stimulate local growth of collateral blood vessel, natural formation of collateral vessels feeding into ischemic tissue is rarely sufficient for full restoration of blood flow in cardiovascular disease patients. Growth of new blood vessels, induced by exogenous angiogenic agents, may restore blood flow to ischemic tissue in patients with various cardiovascular diseases. Stimulatory angiogenic therapy may also provide a minimally invasive approach to improved circulatory function in coronary artery disease (CAD), congestive heart failure, peripheral arterial disease (PAD) and peripheral venous disease (PVD). Stimulatory angiogenic therapies may also facilitate transplant acceptance or survival. Disadvantages of angiogenic stimulators include exacerbation of growth of occult tumors and progression of diabetic retinopathy. An ideal angiogenic agent for inducing growth of collateral arteries around an atherosclerotic plaque should function only in the locality of or be delivered locally to ischemic tissue.

Angiogenesis gene therapy is an experimental technique being used to trick the heart into performing its own bypass operation by growing new blood vessels. The gene coding for a protein, such as VEGF, which encourages new blood vessels to sprout from existing ones is injected into the heart of the patient and the body performs its own coronary bypass. These new vessels are less inclined to silt up again. In preliminary experiments with rabbits, the arteries in rabbit legs have been tied off and the VEGF gene has been applied directly onto the smooth muscle cells lining the artery using a catheter and small balloon. Within three to 10 days, new blood vessels were observed to sprout and find their way around the blockage. Rivard et al., *Circulation* 99 (1):111-120 (1999). In preliminary experiments with humans, the gene has been injected directly into the left ventricle, the pumping chamber of the heart. Results to date from these studies are promising. There have been no side effects and the worst result to date has been no result. The sprouting of new vessels, if it occurs, seems to stop after four to six weeks. Losordo et al., *Circulation* 98 (25):2800-2804 (1998).

E. Angiogenesis in Zebrafish

Figure 1:
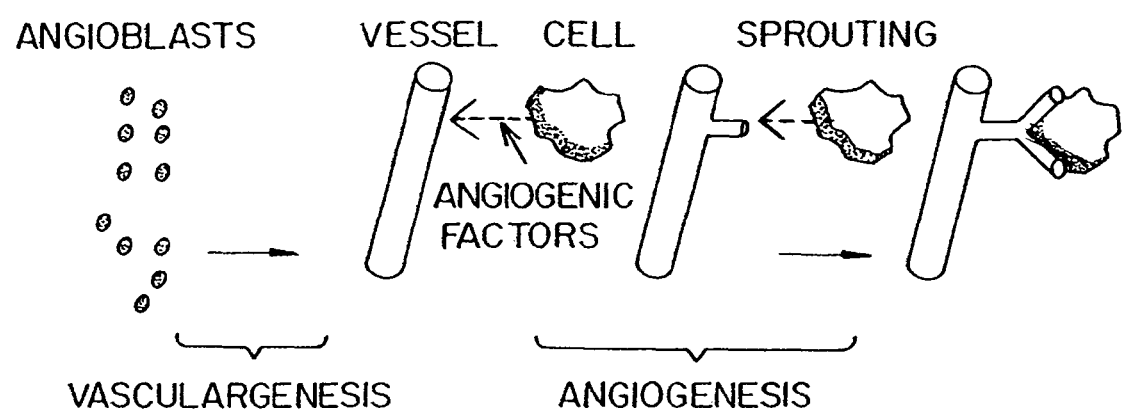
FIG. 1 is a schematic diagram showing the processes of vasculargenesis and angiogenesis.

In the zebrafish, as in other vertebrates, blood vessels form from precursors cells (angioblasts) distributed widely throughout the mesoderm of the embryo. Some angioblasts migrate long distances, while others remain locally to form vessels (Fouquet et al., supra). The major vessels, including the aorta, vena cava, and vessels directed to some organs, are believed to form by local assembly of angioblasts into tubes (vasculargenesis). See FIG. 1. In addition to vasculargenesis, smaller vessels extend from larger vessels to penetrate a specific tissue (angiogenesis) (Fouquet et al., supra). Experiments suggest that both processes of vessel formation—vasculargenesis and angiogenesis—are driven by local signals. By day three of development, the zebrafish has developed an intact, functioning vasculature, including both major vessels and sprouts, which has a consistent pattern of vessel location. See FIGS. 2A and 3A. Because the zebrafish embryo can survive and develop for at least 4-5 days without a circulatory system, with the transparent zebrafish it is possible to study the effects of a variety of agents on all aspects of vascular formation in an intact, live animal.

F. Advantages of Using Zebrafish in Screening Assays for Angiogenesis

Currently, a variety of assays are used to study the process of angiogenesis in various animal models. These assays include preparing a transparent window in the skin of a rabbit or mouse, injecting tumor cells or carrier matrix into an avascular region, such as the cornea, and inducing ischemia by constricting existing blood vessels (Jain et al., *Nat. Med.* 11:1203-1208 (1997)). While these and other approaches generate a great deal of information about the process of angiogenesis, the tissue manipulation required for each assay make them unsuitable for use as screening tools. (Comparative assays are further described in detail below.) Teleosts and zebrafish in particular offer significant advantages for in vivo screening assays for angiogenesis. As noted above, zebrafish are comparatively inexpensive to generate and maintain and the embryos can be placed in individual microtiter wells, making automated analysis with standard liquid handling equipment possible.

In addition, with teleosts, such as zebrafish, the side effects of an agent can be monitored and assessed simultaneously along with the principal effect of the agent. This provides a significant advantage in methods for screening compounds for angiogenesis activity. Notably, one difficulty associated with identifying compounds that can be used as anti-angiogenic agents, such as anti-cancer therapeutics, is that many of the compounds used to inhibit the proliferation of cancer cells also have deleterious effects on proliferating non-cancer cells. This is especially problematic when dealing with cancers that affect children, because many of their organs and tissues are still growing and developing. Using transparent teleost embryos, the effect of an agent on angiogenesis activity as well as any toxic or side effects can be assayed simultaneously. Side effects or toxic effects of agents on zebrafish cells and/or embryogenesis can be monitored at time intervals after administration of the agent. Typically, measurements are performed at the same time as measurements to assess activity of administered agents.

G. Angiogenesis Screening Methods

The present invention provides methods of screening an agent for an ability or capacity of an agent to enhance, inhibit, or block angiogenesis activity in a teleost in response to the administration of a dose of an agent to the teleost. Angiogenesis activity is assessed relative to contemporaneous and/or historical control teleosts (or tissues, organs, or cells thereof) to which the agent has not been administered. Angiogenesis activity is reflected in changes in the vasculature of the teleost. Blood vessel formation and development can be monitored over time in the teleost to which an agent has been administered as well as in control teleosts. A response showing an increase in normal blood vessel formation suggests that the compound enhances or increases angiogenesis. A response showing a decrease or reduction in normal blood vessel formation or the death or loss of previously established, existing blood vessels suggests that the compound decreases, prevents, or inhibits angiogenesis activity (i.e., enhances or stimulates anti-angiogenesis activity) or disrupts existing vessels. Responses indicating an angiogenic activity can be detected in a whole teleost or in one or more organs or tissues of a teleost, either simultaneously or separately. Responses can be detected over time and at predetermined time intervals. These responses can also be detected in vitro in cells of a teleost.

The methods of the present invention are useful in identifying agents that would be effective in therapeutic or prophylactic treatment of a variety of diseases involving angiogenic processes, including cancer, coronary artery disease, congestive heart failure, peripheral arterial disease, peripheral venous disease, neurological diseases, cardiopulmonary diseases, ischemia, developmental diseases, autoimmune diseases, and diseases of bone and cartilage. In general, these methods are useful in screening compounds for therapeutic activity against diseases that would benefit from an increase in angiogenesis activity (e.g., increase in blood vessel formation) or decrease in angiogenesis activity (i.e., anti-angiogenesis activity, a reduction in blood vessel formation).

In one aspect, the methods comprise administering the compound to be screened to a teleost embryo by submerging the embryo in culture media in which the compound has been dissolved prior to the onset of vasculargenesis or angiogenesis. After a suitable period (e.g., 24 or 48 hours), the embryos are fixed and stained for an endogenous blood vessel marker, such as, e.g., alkaline phosphatase (AP). A reduction or increase in the formation of blood vessels and any perturbation in the normal pattern of blood vessels can be determined visually by light microscopy after, e.g., alkaline phosphatase staining, antibody staining of a protein, in situ hybridization. Organ or tissue function can also be determined by measuring enzymatic activity.

Compounds comprising small molecules typically penetrate the teleost embryos by simple diffusion. For compounds that do not penetrate the periderm (the outer ectoderm), dimethyl sulfoxide (DMSO) or other solvents or osmotic shock can be used to transiently permeabilize the periderm. Compounds can also be administered by other well-known methods of administration, including ingestion or direct injection into either the embryo yolk or the heart of the teleost embryo. Once inside the embryo, compounds diffuse freely within the embryo.

For example, to screen for an effect of the compounds on angiogenesis activity, the subintestinal and intersomitic vessels are typically examined. To screen for an effect of the compounds on vasculargenesis activity, the dorsal aorta and ventral vessels are examined. All of these vessels are quite prominent in the unaffected teleost embryo and thus serve as ideal indicators of changes in the vascular pattern. In particular, these vessels are examined for: 1) the presence or absence of vessels, which is indicative of inhibition of angiogenesis; 2) excessive branching, which is indicative of enhancement of angiogenesis; and 3) changes in architecture of the blood vessel formation, which is indicative of changes in local signaling events. In our methods, the zebrafish embryo is used because it can survive and develop for about 4-5 days without a circulatory system and thus the effects of agents on all aspects of vascular formation in the intact embryo can be readily evaluated.

Changes in vascular pattern can be studied by performing RNA in situ hybridization analysis, to examine the angioblasts and vascular growth factors, and microangiography, to examine the circulation and heart function—all of which have roles in blood vessel formation. As an example, a compound to be screened is administered to a 24-hour teleost embryo by dissolving the compound in the culture medium containing the embryo in culture (prior to the onset of vasculargenesis or angiogenesis). After an additional 24 hours (at 48 hours of development), the embryo is visually inspected for morphological defects. 50% of the embryos are fixed for in situ hybridization using the flk-1 probe to identify angioblasts. The remaining embryos are fixed at 72 hours of development and stained with AP. Compounds that affect the expression of endogenous AP, thereby making it difficult to assay vascular pattern by using AP staining, can be assayed by using microangiography. The embryos are then examined for any perturbation in the normal pattern of blood vessels.

Angiogenesis activity can also be detected by standard techniques indicated previously, including, e.g., colorimetry, fluorescence microscopy (including, e.g., time-resolved fluorometry), chemiluminescence, digital image analyzing, standard microplate reader techniques, pattern recognition software for response discrimination and analysis, etc. Antibody staining of specific epitopes can also be used to detect spatial or temporal changes in distribution and expression of epitopes in teleost tissues, as well as molecular modifications.

H. Screening Agents for Angiogenesis Activity and/or Toxic Activity and/or Cell Death Activity Simultaneously The methods for screening agents for angiogenesis or anti-angiogenesis activity can be combined with other methods of the present invention described below, including methods of screening agents for an effect on cell death activity (Section III) or toxic activity (Section IV). Because the teleosts used with these methods are transparent, it is possible to assess angiogenesis or anti-angiogenesis activity in conjunction with other activities. Responses indicating various activities can also be detected in conjunction with one another—either at separate times or simultaneously.

Such combined methods are useful in assessing multiple affects of an agent on a teleost. The agent may cause both a desired response, such as enhancement of angiogenesis, and a toxic (undesired) response. The ability to assess multiple activities and responses in a teleost due to the administration of an agent is of particular benefit in identifying potential therapeutic compounds and assessing their side effects. For example, one difficulty associated with identifying compounds that can be used as anti-cancer therapeutics against targeted cancer cells is that some compounds may also have deleterious effects on non-cancer cells. Anti-angiogenic cancer therapy, for example, typically seeks to induce apoptosis in cancer cells by cutting off the blood supply of such cells. This type of treatment regime may be designed to induce apoptosis in the angioblasts as a means of preventing or diminishing vascularization of the tumor. During treatment, a balance must be achieved such that a negligible level of cell death is induced in other tissues or locations in the body (such as the heart). Such undesired ectopic cell death could be considered a toxic activity. A combination screen for assessing angiogenesis, cell death, and toxic activities of an agent would be useful in identifying those agents that protect the heart from agents which induce apoptosis elsewhere. Dose levels of the agent effective to promote one activity without promoting the other can also be ascertained. Such combined screens would also be useful in identifying and evaluating agents for pro-angiogenic therapies which typically have the therapeutic goal of preventing cell death in a damaged or transplanted tissue.

Multiple activities/responses can be monitored in the whole teleost or in one or more tissues or organs of the teleost. Such activities and responses can be monitored over time and at predetermined time intervals. A variety of techniques can be used together or separately to analyze multiple activities and responses, including, e.g., fluorescence microscopy, light microscopy, digital image analyzing, standard microplate reader techniques (colorimetry, fluorometry, including time-resolved fluorometry, and chemiluminescence), in situ hybridization, antibody staining of specific proteins, changes in protein distribution temporally and spatially within the animal, changes in a level of enzymatic activity in the whole teleost, or tissues, organs or cells of the teleost, etc. Furthermore, the response can be discriminated and/or analyzed by using pattern recognition software.

In one aspect, the present invention provides a method of screening an agent for an increase or decrease in angiogenesis activity as described above which further comprises screening the agent for an increase or decrease in toxicity by detecting a response in the teleost indicating an increase or decrease in toxic activity. Such a method is useful, e.g., in identifying contra indications to therapeutic value of a compound.

In another aspect, the invention provides a method of screening an agent for an increase or decrease in angiogenesis activity as described above which further comprises screening the agent for an ability to enhance or inhibit cell death activity by detecting a response in the teleost indicating an enhancement or inhibition of cell death activity. Such a method is useful, for example, in identifying contra indications to therapeutic value of a compound. Such combination screens also allow for the identification of agents which protect the heart from circulating agents which induce apoptosis elsewhere.

Examples

1. Screening Compounds for Angiogenesis Activity in Zebrafish

A. Materials and Methods
1) Embryo Collection

Zebrafish embryos were generated by natural pair-wise mating as described in Westerfield, supra, which is incorporated herein by reference in its entirety for all purposes. Four to five zebrafish pairs were set up for each mating; on average, 100-150 embryos per pair were generated. Embryos were collected and placed in egg culture media prepared by combining 5 grams (g) of Instant Ocean Salt with 3 g of calcium sulfate in 25 liters of distilled water at 27° C. for approximately 20 hours (21 somite stage) before being sorted for viability, using both morphology and developmental stage as criteria. Healthy embryos were then dechorionated by enzymatic digestion using 1 mg/ml protease (Sigma Chemistry Co.) for 5 minutes at room temperature. The embryos were then washed 5 times in embryo water. Because the fish embryo receives nourishment from an attached yolk ball, no additional maintenance was required.

2) Compounds Screened

Compounds from the following two sources were screened for an ability or capacity to enhance or inhibit angiogenesis activity: NCI Open Synthetic Compound Collection library, Bethesda, Md. and The Center for Cancer Research, Massachusetts Institute of Technology (MIT), Cambridge, Mass.

The NCI Open Synthetic Compound Collection library consists of more than 100,000 unique compound structures; currently, only 12,000 are available for screening.

Compounds obtained from MIT consisted of 11 fumagillin derivatives, including TNP 470 (Turk et al., *Bioorg. Med. Chem.* 8:1163-1169 (1998)) and AGM-1470. Fumagillin is a natural product isolated from fungus with potent anti-angiogenic and toxic effects. AGM-1470 and the other fumagillin derivatives are angiogenesis inhibitors, which prevent entry of normal, but not transformed, endothelial cells into the G1 phase of the cell cycle by binding type 2 methionine aminopeptidase (MetAP2). The derivatives were supplied at an initial concentration of 20 mM. Samples were diluted in dimethyl sulfoxide (DMSO, Sigma Chemical Co.) to a stock concentration of 10 mM.

Compounds from NCI were randomly selected from the NCI Open Synthetic Compound Collection library. The compounds were supplied by NCI in 96 microplate arrays, each at an initial concentration of 10 mM in DMSO. No specific information on compound source, activity, chemical structure, or mechanism of action was available.

3) Administration of Compounds

To determine the effect(s) of a compound on vessel formation on a fish, the compound was added directly to the culture medium solution containing the fish embryos (e.g., to individual microwells containing the fish embryos). Compounds were added to the medium solution at 12 or 24 hours of development of the fish embryo, which is prior to the point at which angiogenic vessels can first be identified using the flk-1 in situ hybridization probe. Fouquet et al., supra. Assays were performed in 6-well, 24-well, or 96-well plates. Such plates facilitated automation of the chemical application and subsequent analysis, including dose response, and subsequent analysis.

4) Visual Screening

After administering a compound to the fish embryos, the embryos were maintained in individual microwells at 28° C. until day 3 of development. Twenty-four and forty-eight hours after adding the compound to the medium in which the fish embryos were cultured, the embryos were visually inspected for viability, gross morphological defects, heart rate, and circulation (see Table 1). Circulation was assayed by following the movement of blood cells through each embryo.

5) Vessel Staining

Figure 7:
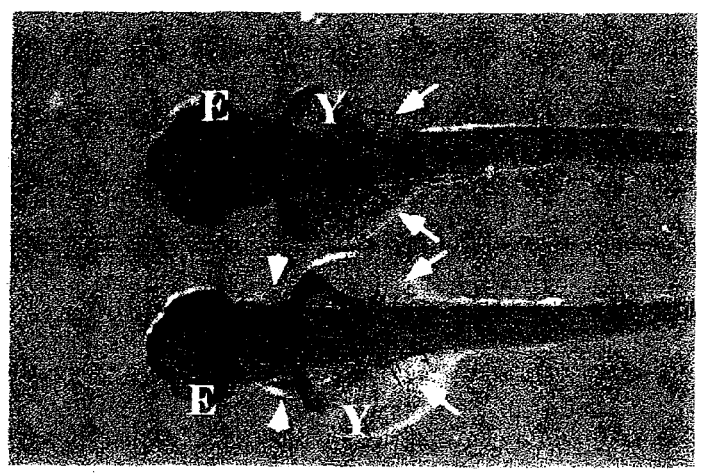
FIG. 7 is a photograph through a compound microscope (10× objective) of an alkaline phosphatase staining of zebrafish embryos at day three of development. These dorsal views of an untreated (top) and a treated (bottom) embryo show the effect of the anti-angiogenesis drug, Ovicillin, on the subintestinal veins (arrows). In addition to causing a reduction in the subintestinal vessels, the drug had other effects, including causing pericardial edema (arrowheads). In this figure, the letter "E" denotes the eye, and the letter "Y" denotes the yolkball.

On the third day of development, embryos were collected for alkaline phosphatase staining. Specifically, embryos were fixed in 4% parafomaldehyde and stained for endogenous alkaline phosphatase activity. Embryos were fixed for 2 hours at room temperature. The embryos were then washed two times in phosphate buffered saline (PBS) and dehydrated by immersion in 25%, 50%, 75% and 100% methanol in phosphate buffered saline with 0.1% Tween (PBT) to permeabilize the embryos. The embryos were then rehydrated and washed in 100% PBT. For staining, embryos were equilibrated in NTMT buffer (0.1M Tris-HCl pH 9.5; 50 mM MgCl; 0.1M NaCl; 0.1% Tween 20) at room temperature. After the embryos equilibrated, embryos were stained by adding 4.5 µl of 75 mg/ml nitro blue tetrazolium (NBT) and 3.5 µL of 50 mg/ml X-phosphate per ml. After staining for 10 minutes, all the blood vessels in the fish embryo were labeled (see FIGS. 2A-2C, 3A-3B, 4, 7). The staining reaction was stopped by addition of PBST. Embryos were then examined on a stereo-dissecting microscope. One advantage of using the zebrafish for this type of assay is that the subintestinal vessels, which are located over the yolk, are both sensitive to factors which effect vessel formation and easily assayed by this method (see, e.g., FIG. 7). The subintestinal vessels are normally present on the dorsolateral surface of the yolk of zebrafish embryos by 48 hours of development. They form a distinct basket shape that extends 50-100 µm from the ventral edge of the somite over the yolk. By assaying the subintestinal vessels at 72 hours of development (24 hours after the subintestinal vessels normally appear), normal variation in the timing of the vessel formation was avoided. The staining procedure is easily automated using commercially available instrumentation.

6) Bleaching Teleosts

If desired, teleosts (e.g., zebrafish embryos) can be bleached before or after alkaline phosphatase staining. Bleaching removes the melanin pigment from the teleost and permits the screening of teleost without the adverse effects of 1-phenyl-2-thiourea (PTU) treatment. Post-stain bleaching also removes the extracellular staining associated with background staining. Bleaching effectively enhances visualization and analysis of the response of the treated teleost to a compound through the removal pigmentation of some cells. Bleaching enhances visual detection of responses indicating toxic, angiogenic, and cell death activities.

To bleach zebrafish, the fish were immersed for 10 minutes at room temperature in 5% formamide, 1× sodium chloride/sodium citrate and 10% hydrogen peroxide.

7) In Situ Hybridization

In addition to performing visual screens, specific molecular changes in teleost tissues can be detected by in situ hybridization of RNA or antibody staining of specific proteins. In situ hybridization of RNA is a routine molecular approach in zebrafish (Westerfield, supra). A digoxigenin-labeling kit from Boehringer Mannheim can be used to label the RNA probes. Whole mount in situ hybridization can be carried out as follows: Embryos are fixed with 4% paraformaldehyde in PBS, lightly digested with proteinase K, and hybridized with 1 µg of probe in in situ hybridization solution (50% formamide, 5×SSC, 50 µg/ml Heparin, 500 µg/ml tRNA, 92 µl of 1M citric acid, pH 6.0, and 0.1% Tween 20) at 65° C. Alkaline phosphatase-conjugated anti-digoxigenin antibody is used to detect signals. Background staining from endogenous alkaline phosphatase does not pose a problem, because endogenous alkaline phosphatase does not survive the in situ hybridization procedure. After staining with NBT/X-phosphatase (Boehringer Mannheim), embryos are bleached in 100% methanol, refixed in 4% paraformaldehyde, and stored in PBS. Multiple in situ hybridizations can be performed simultaneously on different teleosts in multi-well dishes.

8) Additional Assays for Angiogenesis

To determine if any changes in vascular pattern are due to inhibition or stimulation of the angioblasts, RNA in situ hybridization analysis on known angioblast markers, flk-1, tie, tek, and fli (Dumont et al., *Dev. Dyn.* 203:80-92 (1995); Liao et al., *Dev. Suppl.* 124:381-389 (1996); Fouquet et al., supra) can be performed using procedures outlined above.

Figure 8:
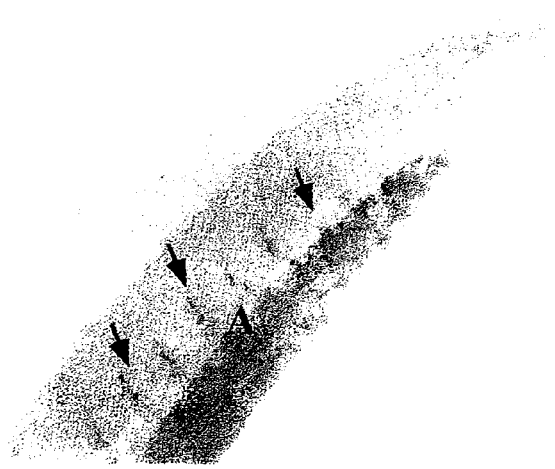
FIG. 8 is a photograph through a compound microscope (20× objective) showing a wholemount RNA in situ hybridization with flk-1 performed on a day one zebrafish embryo.

Flk-1 (FIG. 8), tie, and tek are receptor tyrosine kinases, which label angioblasts early in development. Fli is a transcription factor which labels them at a later stage. Because flk-1, tie, tek, and fli appear sequentially during angioblast development in vertebrates (Dumont et al., supra), assaying for the presence or absence of these molecules makes it possible not only to determine if the angioblasts are affected, but also the stage of development at which they are affected.

Changes in the distribution of a protein both spatially and temporally, including a complete absence of a protein, within the intact teleost can be detected. For example, changes in the pattern of the vascular endothelial growth factor, VEGF, can be examined using standard antibody staining procedures (Westerfield, supra) or in situ hybridization techniques described above (see also Westerfield, supra). VEGF is believed to have two roles in vascular development: 1) a chemo-attractant or guidance role; and 2) a maintenance role (Dumont et al., supra). Thus, chemicals which affect VEGF expression are of particular interest. The above are examples of well known molecular markers; other molecular markers can also be employed.

9) Function Assay

In addition to changes in the vascular architecture, vascular function (circulation and heart rate) may also be affected by compounds. To determine whether a compound administered to zebrafish affected vascular functioning (e.g., heart rate and circulation), heart rate and circulation of the zebrafish embryos are studied. In this instance, heart rate was assessed by counting the heart beats/minute. Circulation was assessed by examining zebrafish embryos under a dissecting microscope for the movement of blood cells through the heart and major vessels. Zebrafish embryos were also examined for blood pooling in the yolk (an indicator of poor blood flow through the heart) and in the body of the embryo (an indication of leaky vessels). In those embryos in which a compound was observed to affect blood cell development, micro-angiography was performed using the procedures outlined in Weinstein et al., *Nature Med.* 1:1143-1147 (1995) to examine the integrity of the vascular system for vessel leakage and blockage, which can cause changes in vessel formation and maintenance. Embryos were anesthetized with tricaine to stop the heart, a micro-pipet was inserted into the heart, and fluorescent beads were injected. The tricaine was then washed out, and the heart resumed beating. The flow of fluorescent beads was then observed using an epifluorescence microscope and recorded using a low light level camera attached to a computer (FIG. 9). This approach allows examination of the integrity of the vascular system and assessment of the effects of the chemicals on the condition of the heart.

B. Results

1) Determination of Parameters for the Delivery of Compounds to Target Tissues and Organs a) Embryo Developmental Stage In our initial studies, we employed 12-hour zebrafish embryos (6 somite stage) for the assays and began the assays at the $12^{th}$ hour of development. Although this time point is advantageous because it is just prior to the onset of angioblast formation (Fouquet et al., supra), there are several disadvantages. The most significant of these is that at 12 hours of development, many structures of the zebrafish embryo including the notochord, the somites, and the heart are beginning to form. Because these structures directly affect both vasculargenesis and angiogenesis, it is difficult to determine if the observed effects of compounds on vessel formation are primary (direct effects on the vessels) or secondary (indirect effects due to damage to other tissues).

To circumvent this problem, we began the assays at 22 hours of development (26 somite stage). At this stage of development, the dorsal aorta and ventral vein are present in the anterior, but not in the posterior regions of the zebrafish embryo. This permitted examination of both vasculargenesis and angiogenesis independently in the same embryo. For vasculargenesis, we examined the embryos for the presence of the dorsal aorta and ventral vessel in the most posterior regions of the tail. For angiogenesis, we examined the embryos for the presence of sprouting vessels, including the subintestinal and the intersomitic vessels. The subintestinal vessels begin to form at 36 hours of development; therefore, using the 22-hour time point reduces the time between compound administration and angiogenic vessel formation. This is an important consideration for compounds that are unstable under the culture conditions.

b) Embryo Maintenance

Initial experiments were performed in 35 mm wells in 6-well culture dishes using 50 zebrafish embryos per well in 5 ml of embryo water. While this approach worked, it has a number of drawbacks, including that: 1) a relatively large amount of compound must be used to dose the embryos; 2) the number of compounds that can be screened simultaneously is limited; and 3) because there are multiple embryos in a dish, dying embryos could contaminate living embryos.

In an attempt to circumvent these drawbacks, we examined two alternative formats, the 96- and the 24-well plate. Previous observations indicated that single zebrafish embryos were capable of surviving and developing normally in 50-100 µl of embryo water for up to 5 days. Therefore, we collected, dechorionated and sorted 22 hour embryos into either: 1) 96 well plates with one embryo per well in 100 µl; or 2) 24 well plates with 5 embryos in 500 µl of embryo water. The embryos were allowed to develop for 72 hours before examination. The embryos were assessed by size, morphology, and movement. No obvious differences were observed between the embryos raised in the microwell plates and control embryos raised in larger containers. The embryos were fixed and stained for endogenous alkaline phosphatase to examine vessel formation. The staining pattern in the experimental embryos was identical to that observed in the controls. For the manual screen, we preferred the 24 well format and used it for all experiments described below.

c) Compound Delivery

In order to optimize the parameters for screening compounds, we performed a series of experiments using the 11 fumagillin derivatives obtained from MIT and 10 random compounds obtained from the NCI Open Synthetic Compound Collection library. We knew from our feasibility studies that fumagillin inhibited angiogenesis in the zebrafish; we thus decided to use these compounds as positive controls to verify the assay. We also used the 10 compounds from NCI to verify that the established parameters were appropriate for other types of compounds. In general, we expected that the small molecules would diffuse freely both into the embryo and through the chorion membrane that surrounds the embryo for the first 2-3 days of development. However, to avoid potential problems, we removed the chorion by enzymatic digestion. This approach is well established and when done properly produces no adverse effects on the embryos.

TABLE 1

Summary of Concentration Effects of Compounds

| Compound | 100 µM | Effect | 10 µM | Effect | 1 µM | Effect |
|---|---|---|---|---|---|---|
| MIT (11) | 11/11 | Lethal | 7/10 | Vascular effects | 11/11 | Slight Developmental Delay |
|  |  |  |  | Developmental Delay |  |  |
| NCI (10) | 4/10 | Lethal | 1/10 | Lethal | 1/10 | Lethal |
|  | 6/10 | Slight Developmental Delay | 2/10 | Chromatic Change | 10/10 | Slight Developmental Delay |
|  |  |  | 10/10 | Slight Developmental Delay |  |  | d) Compound Concentration

As a primary screen for compound effects, we tested each compound at three different concentrations to determine which concentration would provide the most information. The concentrations tested were 100 µM, 10 µM, and 1 µM. Results are summarized in Table 1. For these experiments, we added 50 µl of 10 mM stock solution to 5 ml of embryo water to generate a 100 µM solution in 1% DMSO. The subsequent concentrations were generated by 1:10 and 1:100 dilutions in embryo water; for each concentration, DMSO added to 1% of the total solution. The control solutions consisted of 1% DMSO in embryo water. Ten embryos per compound per concentration were tested. Of the 21 compounds tested, 15 (11/11 MIT, 4/10 NCI) were lethal at the 100 µM concentration. At the 10 µM concentration, 7/11 of the fumagillin derivatives had an inhibitory effect on angiogenesis. However, while none of the fumagillin derivatives were lethal at 10 µM, they all had a deleterious effect on the growth of the embryo (FIG. 2A), consistent with previously published results showing that the target of fumagillin derivatives is methionine aminopeptidase (type 2), which plays a role in cell cycle control in eukaryotic cells (Ishikawa et al., *J. Exp. Ther. Oncol.* 6:390-396 (1996); Kria et al., *Curr. Eye Res.* 10:986-993 (1998).

In contrast to the fumagillin derivatives, at 10 µM the NCI compounds had no observable effect on vessel formation. However, 1 of the 10 NCI compounds was lethal at this concentration and 2 of the 10 compounds caused a chromatic change in the embryos. The chromatic changes were not limited simply to taking up the color of the compound; one of the NCI compounds caused the melanocytes to turn purple. As with the fumagillin derivatives, all 9 of the non-lethal NCI compounds caused a slight developmental delay, because the embryos appeared by morphological criteria to be ~12 hours delayed in development. At 1 µM, 20/21 compounds caused developmental delay and 1/21 caused lethality. These results show quite clearly that compounds added to the media were capable of getting into the zebrafish embryo and inducing an effect.

e) Use of DMSO

One problem with the experimental conditions described above was that the control embryos maintained in 1% DMSO in embryo water also showed a slight developmental delay, similar to that observed for all of the concentrations of the NCI compounds and for the 1 µM concentration the fumagillin derivatives. We repeated the experiments using 10 µM and 1 µM concentrations of the compounds, respectively, in 0.1% DMSO. The results were identical to those in Table 1, except that the developmental delay for all of the compounds except the fumagillin derivatives at 10 µM concentration was eliminated. After performing these experiments, we decided to use 10 µM concentrations with 0.1% DMSO. The results indicated that at relatively high concentrations, DMSO has some effect on developing zebrafish. While DMSO does not appear to have any effect on developing zebrafish at lower concentrations, we are aware that synergistic effects may occur. Unfortunately, many of the compounds available for screening were only soluble in DSMO or similar solvents. As with any primary screen, positive results will require further verification and scrutiny.

2) Assessing the Effects of Compounds on Blood Vessel Formation

After establishing basic assay parameters, we screened compounds received from MIT (11 compounds) and NCI (190 compounds) for effects on blood vessel formation (angiogenesis and vasculargenesis). Embryos were collected at 20 hours of development and dechorionated. At 22 hours of development, the embryos were sorted into 24 well plates with 5 embryos per well in 500 µl of embryo water. The compounds from MIT and NCI were added at a concentration of 10 µM. For each compound, 3 sets of embryos (15 total) were screened. For convenience, each set was maintained in a separate multi-well plate. This permitted testing of 23 compounds/plate with 1 set of controls per plate. At 72 hours of development, embryos were visually screened for gross morphological defects and cardiac function using a dissecting microscope. After the visual screen, embryos were fixed and stained for endogenous alkaline phosphatase activity in order to analyze vascular architecture. Experimental results are shown in Table 2 and described below.

TABLE 2

Results of Visual Screen

| Compounds (Compds) | Number Compds Screened | Vascular Changes | Developmental Delay | Axial Defects | Cranial Defects | Circulation/ Heart Rate Defects | Compds toxic at 10 μM |
|---|---|---|---|---|---|---|---|
| NCI | 190 | 18 | 16 | 6 | 7 | 6 | 13 |
| MIT | 11 | 7 | 11 | 3 | 0 | 0 | 0 | a) Vascular Changes

Figure 6A:
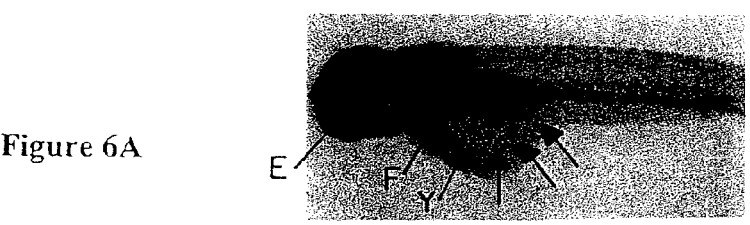
FIGS. 6A-6D are photographs through a dissecting microscope showing lateral views of zebrafish embryos at 72 hours of development. Embryos have been stained with AP. When VEGF was injected into the yolk of an embryo (FIGS. 6A and 6C), two angiogenic phenotypes were observed: 1) the appearance of long spikes projecting from the subintestinal vessel basket (long arrows); and 2) increased vessel diameters in the subintestinal basket (arrowheads). When VEGF was injected into the perivitelline space (FIG. 6D) of an embryo, we observed fusion of large vessels, inappropriate vessel formation (arrow), as well as heart (long arrow) and developmental defects. Control embryos (FIG. 6B), in which buffer was injected into either the yolk of perivitelline space, were normal. The eye (E), yolk (Y) and fin (F) of the embryos are labeled for orientation. Scale bar=100 μm.
Figure 6B:
Figure 6C:
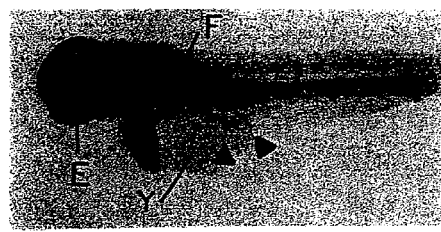
Figure 6D:
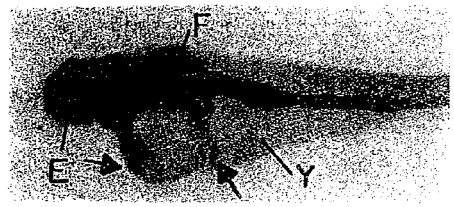

To assay vessel formation, embryos were fixed and stained and the vessels were scored as described above. The subintestinal vessels form on the dorsolateral surface of the yolk on both sides of the embryo in the shape of a basket that extends 50-100 μm from the ventral edge of the somite over the yolk. For this screen, anti-angiogenic effects were defined as either the complete absence of these vessels or the loss of either the lateral or dorsal ventral vessels of the basket (FIGS. 2B-2C, 3B, 4). An angiogenic effect was defined for this screen as an enlargement of the basket beyond 150 μm from the somite. This includes both increases in size of the entire basket and/or projections from the basket (FIGS. 6A, 6C, 6D). In addition to the overall basket size, we also looked for increases in the diameter of the vessels. Normal vessels are less than 10 μm in diameter. Embryos were also screened for gross changes in the large vessels, including the dorsal aorta and ventral vein.

Figure 2A:
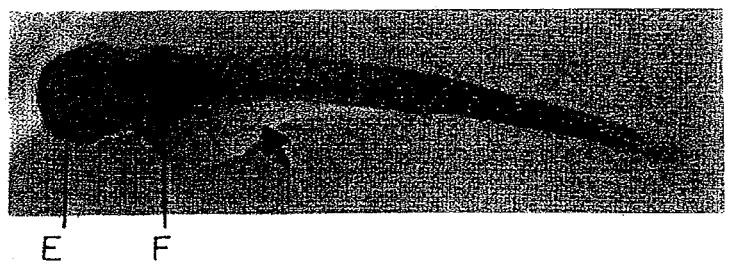
FIGS. 2A, 2B, and 2C are photographs through a dissecting microscope showing lateral views of zebrafish embryos at 72 hours (hr) of development. The embryos have been stained with alkaline phosphatase (AP). Blood vessels are visualized by light microscopy after alkaline phosphatase staining. A control embryo (FIG. 2A) treated with 0.1% dimethyl sulfoxide (DMSO) has normal morphology and vessel formation. The subintestinal vessels (SIVs) (arrow) are in the characteristic pattern. An embryo treated with a fumagillin derivative at concentration of 10 micromolar (μM) (FIG. 2B) shows both developmental delay (reduced fin size and axial length) and loss of the SIVs (arrow). The proneperic duct provides a positive control for AP staining (arrowhead). An embryo treated with a fumagillin derivative at a concentration of 100 μM (FIG. 2C) is dead. Fumagillin derivatives induce developmental delay and toxic response in the embryos. The eye (E), yolk (Y) and fin (F) of the embryos are labeled for orientation. Scale bar=100 μm.
Figure 2B:
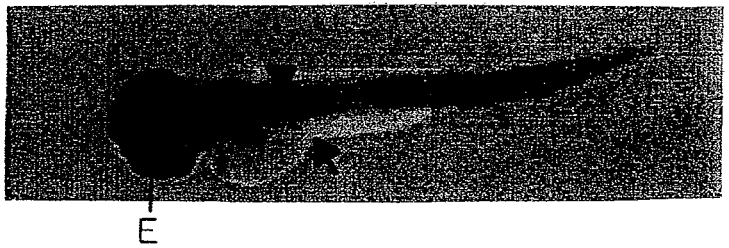
Figure 3A:
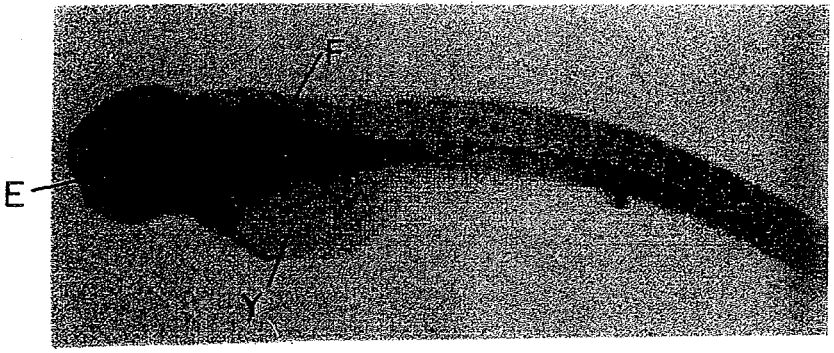
FIGS. 3A and 3B are photographs through a dissecting microscope showing two lateral views of zebrafish embryos at 72 hours of development. Each embryo has been stained with alkaline phosphatase.
Figure 3B:
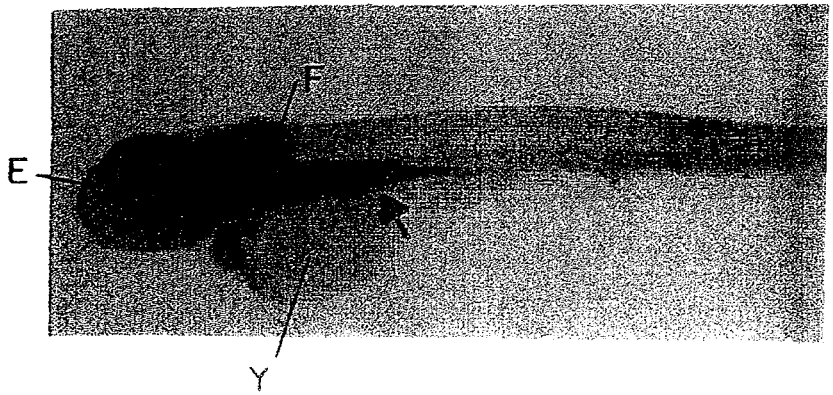
Figure 4:
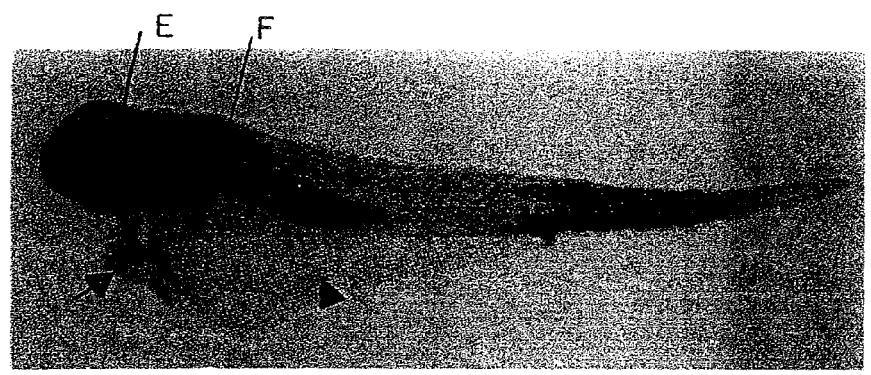
FIG. 4 is a photograph through a dissecting microscope of a lateral view of an alkaline-phosphatase stained zebrafish embryo at 72 hours of development. The embryo has been treated with a compound which induced truncation, pericardial edema (arrow), and reduction of SIV formation (arrowhead). A loss of lateral vessels in the SIV basket is shown. The eye (E), yolk (Y) and fin (F) of the embryo are labeled for orientation. Scale bar=100 μm.

Of the 241 compounds tested, 25 (7/11 from MIT and 18/190 from NCI) caused some anti-angiogenic effects (Table 3). Of these, 23/25 were associated with various degrees of developmental delay; the more severe the delay, the more dramatic was the reduction in vessel formation (FIGS. 2A-2B). Of the two other compounds that caused a reduction or loss in vessel formation, one was associated with a truncation of the embryonic axis (FIG. 4). Axial defects do not generally cause a loss of the subintestinal vessels, suggesting that the vessel effect may be distinct from the axial effect. Only 1 of the compounds tested showed a specific effect on vessel formation. With this compound, there was a loss of the subintestinal vessels (FIG. 2B), with no other observable effects on the embryo.

embryos treated with the compounds that had previously been shown to cause a reduction of vessel formation. We used a probe against flk-1, a receptor tyrosine kinase that has been shown to play a pivotal role in angiogenic vessel formation (Hanahan, supra). Flk-1 has been shown to be the earliest marker for angioblast in the zebrafish embryo (Fouquet et al., supra). Normally, flk-1 is highly expressed throughout development in newly forming vessels and expressed at lower levels in the large vessels after their formation. In the absence of angiogenic vessels, we would not expect to see flk-1 expression in the somitic and subintestinal region; therefore, we focused on expression of flk-1 in the large vessels.

Figure 5:
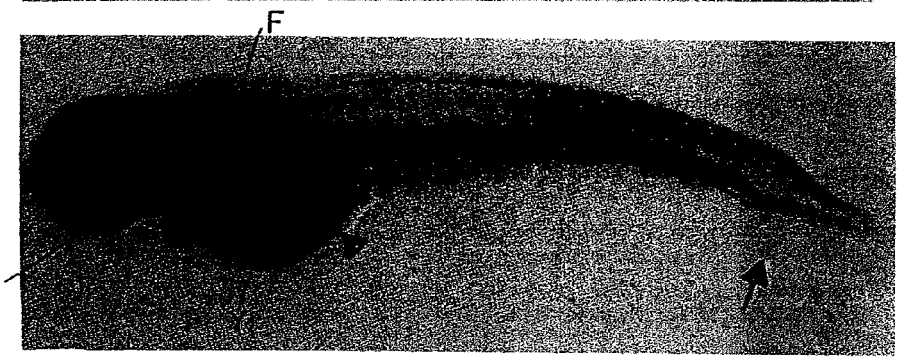
FIG. 5 is a photograph through a dissecting microscope showing a lateral view of a zebrafish embryo treated with a compound which induced blebbing of the notocord (arrow), but did not effect SIV formation (arrowhead). The embryo been stained with AP. Axial defects do not usually effect angiogenesis. The eye (E), yolk (Y) and fin (F) of the embryo are labeled for orientation. Scale bar=100 μm.

Embryos were collected at 48 hours of development (24 hours after addition of the compounds) because Flk-1 is still highly expressed in the large vessels at this stage. For 17 of the 18 NCI compounds which caused a reduction in the subintestinal vessels, the pattern of flk-1 staining appeared normal at 48 hrs of development. Specifically, flk-1 staining was present in the dorsal aorta and ventral vein as well as in the vessels of the head. There was no staining in either the intersomitic space or on the dorsal surface of the yolk, however; this was expected, because these vessels did not form. One compound caused a loss of flk-1 staining in the large vessels of the tail, but not in the head. This compound also caused a truncation of the embryo, a thinning of the tail and heart malformation (FIG. 5). It is probable that the loss of flk-1 staining was part of a more global defect, rather than a specific anti-angiogenic effect.

b) Developmental Delay

Because a number of the defects included changes in the size and shape of the embryo, to distinguish between mor-

TABLE 3

Observed Effects of Compounds on Vessel Formation

| Compds (Source) | Vessel Effect | Complete Loss of Subintestinal Vessels (SIVs) | Loss of Lateral or Dorsalventral Vessels of SIVs | Increase in SIVs | Increase in Vessel Diameter | Changes in Large Vessels |
|---|---|---|---|---|---|---|
| MIT (11) | 7/11 | 4 | 3 | 0 | 0 | 5 |
| NCI (190) | 18/190 | 5 | 13 | 0 | 0 | 3 |

With 8/25 compounds that caused angiogenic effect, we observed what appeared to be a failure of the large vessels to organize properly in the tail. We only observed this effect with compounds that induced severe developmental delay. It is likely that the failure of the aortal and ventral vein to organize properly may be a secondary effect. Curiously, none of the compounds screened caused an increase in vessel formation as assayed by increases either in size of the subintestinal vessels or the diameter of the vessels.

Figure 2C:
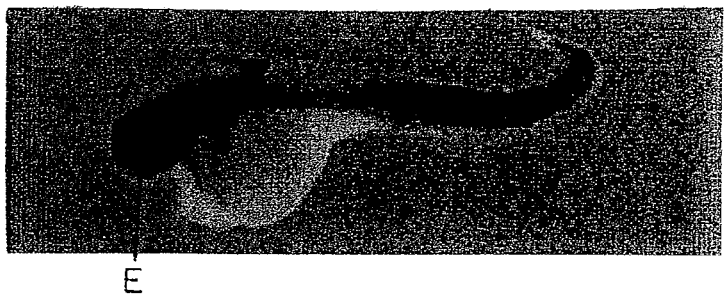

To determine if the loss of the subintestinal vessels was due to the loss of angioblast, we performed an in situ analysis on phological defects and developmental delay, we used three distinct parameters. Normally, zebrafish embryos are staged by the position of the head on the yolk ball, the length of the embryo, and the position of the forming melanocytes. As our $4^{th}$ criteria, we used the size and shape of the fins to assist in staging the embryos. For this screen, developmental delay was defined as at least 12 hours slower than the control embryos on the same multi-well plate. As previously noted, all the fumagillin derivatives caused a substantial developmental delay of at least 24 hours (FIGS. 2A-2C). This is probably because the target of these compounds is a cell cycle regulating protein (Turk et al., supra). Developmental delay was also observed in 16 of the 190 (8.5%) small molecule compounds from NCI. In all cases where developmental delay was observed, there was a change in vascular architecture consistent with the developmental delay (FIGS. 2A-2C). It is likely that compounds that affect proliferation and growth will also affect angiogenic vessel formation, which requires cell proliferation in order to form new vessels. Eight of these 16 compounds also caused what appeared to be a disorganization of the large vessels in the tail.

c) Axial Defects

There were three typical types of axial defects: 1) bending of the axis either up or down (NCI 3/6, MIT 3/3); 2) truncation of the axis (NCI 2/6); and 3) blebbing of the notochord (FIG. 5)(NCI 2/6). A reduction of the subintestinal vessels was observed with only one of the compounds that caused an axial defect (FIG. 4).

d) Cranial Defects

Cranial defects were defined as either the disruption of the central nervous system (CNS) morphology, usually at the midbrain/hindbrain border, or the presence of cellular debris in the ventricular space of the CNS. Seven of the 190 NCI compounds caused cranial defects; however, none affected the subintestinal vessel or the large vessels in the tail.

e) Toxicity

For this specific experiment, we defined toxicity as whole embryo lethality by 72 hours of development. Using the previously established assay parameters, we predicted that the 10 µM concentration of a compound was unlikely to induce toxicity. Therefore, we were not surprised that only 5% (6.8% of NCI, 13/190) of the compounds tested were lethal. Of the 13 lethal compounds, eight killed the embryos within 24 hours of application. The remaining 5 compounds caused localized cell death (4 in the tail and 1 in the head) within 24 hours and whole embryo lethality by 72 hours of development. It is possible that at lower concentrations these compounds can affect angiogenesis without causing toxicity; however, this seems unlikely, as the toxic effects were quite global.

3) Assessing Effects on Vascular Function a) Circulation/Heart Rate Defects

There were a number of compounds causing developmental delay and axial defects that also caused structural changes in the heart. In general, these effects were consistent with underdevelopment of the heart. In order to evaluate function, we restricted our analysis to embryos in which the heart appeared relatively normal, as defined by the presence of an atrium and a ventricle, as well as a heartbeat. 6/190 of the NCI compounds caused a reduction in the beat rate of the heart. For this screen, reduced heart rate was defined as 50% or less than the rate of controls. Because biological and environmental factors cause natural variations in the heart rate, the normal heart rate was taken as the average heart rate of the 10 embryos in the control wells for each plate. This was compared to the average heart rate of the embryos in the experimental well. In 3/6 compounds, pericardial edema and blood pooling over the yolk accompanied the reduced rate. Even though pericardial edema was evident, blood cells moved through the major vessels. All three of these compounds caused developmental delay with an associated reduction in angiogenic vessels; specifically, the subintestinal vessels were absent. The remaining 3 compounds had no observable effects other than reduced heart rate.

None of the non-lethal compounds tested caused an observable reduction in the number of blood cells; thus, it was possible to assay circulation by observing the movement of blood cells through the vessels. As with assessment of heart rate, only embryos with structurally normal hearts were analyzed, because malformed or underdeveloped hearts cannot usually pump blood. None of the compounds appeared to affect circulation as assessed by lack of blood flow, blood pooling, or leaky vessels.

Circulation was assayed by observing the flow of blood cells through the embryo. Of the 212 compounds tested in this study, none affected the formation of the blood cells; therefore, it was not necessary to perform any microangiograms to assay circulation. However, because it is unlikely that this will be the case for all compounds, the microangiogram technique is typically included as part of the screening methods. A microangiogram was performed as part of our initial studies on a zebrafish embryo at day three of development. The microangiogram shows the normal vascular pattern of the zebrafish embryo, including the cranial, intersegmental, and subintestinal vessels. See FIG. 9.

C. Discussion

The above results demonstrate that the teleost (e.g., zebrafish) is a viable model for screening small molecules (e.g., chemical compounds) for effects on vessel formation. Such small molecules not only diffuse into the embryo, but can also induce specific, observable effects on blood vessel formation.

1) Diffusion of Small Compounds into the Teleost Embryo

One major concern prior to experimentation was whether different types of small molecules would diffuse into the zebrafish embryos after addition to the media. Our initial studies demonstrated that fumagillin and ovicillin were capable of diffusing into the zebrafish embryo. However, these compounds are natural products identified because of their ability to diffuse into cells in culture. Of the 201 small molecule compounds screened, 81 had some observable effect on zebrafish embryos (70/190 compounds, including 23 which caused color changes (data not shown), from NCI and 11/11 fumagillin derivatives). These results suggest that our initial assumption that small molecules would enter the embryos by diffusion was correct.

2) Advantages of Whole Embryo Screening

One significant advantage of using whole teleost embryos for assays is the ability to identify effects on multiple targets simultaneously. In our initial set of experiments, we restricted additional targets to events that could be visualized without additional staining. Developmental delay was the most useful of these parameters. Unlike with cell culture assays, with the whole embryo assay, we were able to observe that the 11 MIT compounds caused what appeared to be general cell proliferation effects, which may or may not be the same as anti-angiogenic effects. This may be due to the binding of type 2 methionine aminopeptidase (MetAP2) (Turk et al., supra) or a related cell cycle protein.

We also observed a number of other effects with other compounds. With 6 compounds, we observed effects on heart rate in live embryos by visual inspection. Because the heart is quite prominent in the early embryo, it was possible to observe a slow versus normal heart rate by visual inspection. Two possible mechanisms for this observed effect are: 1) the compound may affect development of the heart in such a way that the conductivity mechanism required for normal heart beat is absent, or 2) the compound directly antagonizes the conductivity mechanism in a manner similar to beta-blockers (Reiter and Reiffel, *Am. J. Cardiol.* 82 (4A):9-19 (1998)). We were also able to score cranial defects in 7/201 compounds, as well as axial defects in 9/201. In subsequent studies (described below), we used specific antibodies and staining techniques to analyze the effects of compounds on other organs, including the liver and the kidney, to determine adverse effects of angiogenic compounds. The liver and kidney are highly vascularized; as a result, these organs represent potential targets for screening compounds for adverse effects on blood vessel formation.

3) Screening for Anti-Angiogenic Effects

In our first set of screening experiments for anti-angiogenic effects, we examined the effect of fumagillin, a natural anti-angiogenesis chemical, on blood vessel formation in the zebrafish embryo. The compound was administered by addition to the fish culture media. This compound caused a reduction in angiogenesis, indicated by a reduction of the subintestinal and intersomitic vessels (see, e.g., FIG. 7). However, each compound also caused serious complications in the embryo including pericardial edema, developmental delay, and axial defects. Although these experiments demonstrated the feasibility of the approach for drug screening, they also underscored the importance of identifying compounds that affect angiogenesis selectively. Using the screening parameters described above, we identified two compounds that caused apparently specific anti-angiogenic effects. In addition, we identified 16 other compounds that caused a reduction of angiogenic vessel formation in addition to other effects. These results show that the zebrafish embryo model can be used to screen for compounds that specifically affect angiogenesis and anti-angiogenesis activities.

4) Screening for Angioblast Formation Using Flk-1 Staining 1 of the 18 NCI compounds that caused a reduction in subintestinal vessel formation had an effect on the flk-1 staining pattern. Because flk-1 is an early marker for angioblasts, this result suggests that for 17/18 compounds, the blocking of angiogenesis is not due to loss of angioblast, but rather to interference with some other component of the angiogenic pathway. For the one compound that did affect flk-1 staining, it was not clear if the loss of staining was due to a loss of angioblasts or loss of the flk-1 tyrosine kinase expression. This demonstrates the importance of establishing markers for both angioblasts and the angiogenic pathway (see discussion below).

5) Angiogenic Effects

None of the compounds tested caused an observable increase in vessel formation. Two possible explanations of this observation are: 1) none of the compounds tested had angiogenic properties; and 2) the normal zebrafish embryo is refractory to exogenous angiogenic stimulation. To distinguish between these two possibilities, we performed experiments, described below, in which VEGF was injected into 24 hour embryos. These experiments suggested that increased angiogenesis can be induced in the normal zebrafish embryo (FIGS. 5A-5C). In order to increase the likelihood of identifying compounds which stimulate angiogenesis, we explored the use of mutant zebrafish lines, such as the gridlock mutant (Weinstein et al., supra), which has defects which block angiogenesis.

6) Vasculargenesis

In the zebrafish as in humans, vasculargenesis is the process by which the large vessels, including the aorta, vena cava, and vessels to some organs, form from local precursors cells (angioblasts) distributed throughout the mesoderm of the embryo (Fouquet et al., supra). We observed vascular defects with 8 of the 241 compounds screened. The effects observed were limited to a disorganization of the dorsal aorta and ventral vessel in embryos with severe developmental delay. It is not clear that vasculargenesis requires extensive cell proliferation, and these observed effects on the large vessels may be due to a disruption of the surrounding tissue, rather than a direct effect on the angioblasts.

7) Rapid and Automated Methods of Screening of Agents for Angiogenesis Activity

Our experiments demonstrated the versatility and value of the teleost as a model for use in detecting, identifying, and analyzing compounds that inhibit or enhance angiogenesis in vivo and in vitro. With methods of the present invention, teleosts (e.g., zebrafish embryos) can be used to screen large numbers of compounds rapidly for effects on angiogenesis. For example, using the 24 well format and manual techniques for fluid changes, we screened 241 compounds for a variety of effects at multiple time points. These effects included morphological defects, functional defects, and lethality. While these target effects provide a tremendous amount of information, analysis of other targets such as heart rate, circulation, and other organs constitute a secondary level of screening that should be performed only on compounds pre-screened for angiogenic effects. A primary screen for compounds which affect angiogenesis should focus on the stained subintestinal vessels in 72 hour embryos.

The present invention also includes automated methods for rapid screening of compounds that enhance or inhibit angiogenesis activity in animal models in vivo and in vitro in cells thereof. Preferred animal models include transparent teleosts, such as zebrafish. Any of the compounds described herein can be screened using automated procedures described previously, including, e.g., small chemical compounds or larger biological molecules discussed below.

In our analyses discussed above, we screened 190 compounds from the NCI Open Synthetic Compound Collection library. Although this library consists of more than 100,000 unique compound structures, currently only 12,000 are available for screening. Using the manual screening methods of the invention, the entire compound library can be screened in two years. Incorporation of commercially available fluid handling instrumentation significantly reduces this time frame to less than three months.

2. Screening Biological Molecules for Angiogenesis Activity

The present invention also includes methods of screening of larger molecules, including biological molecules, for an ability to enhance or inhibit angiogenesis activity. These methods comprise administering the compound to a teleost and detecting a response indicating an enhancement or inhibition in angiogenesis activity. No precise method for screening large biological molecules for angiogenesis activity currently exists. Thus, the methods of the invention are thus of particular value and use in evaluating the use of biological compounds as therapeutics and/or prophylactics for treating a variety of diseases in humans associated with angiogenesis processes, including neurological diseases, cardiopulmonary diseases, ischemia, developmental diseases, autoimmune diseases, diseases of bone and cartilage, and cancer.

A wide range of biological compounds, including peptides, proteins, glycoproteins, nucleic acids (e.g., DNA and RNA), lipids, glycolipids, and the like, including, but not limited to, derivatives, analogues, and chimeras of such compounds, can be screened by these methods. As discussed above, compounds from a library of compounds, including a combinatorial library, can be screened.

Recently, a number of biological molecules have been identified that have either anti-angiogenic or angiogenic effects (Hanahan, Science 277 (5322):48-50 (1997); Zetter, supra). Some biological compounds have been characterized and analyzed for angiogenesis activity in cell cultures and in mice; a few such compounds have been tested in therapeutic and/or prophylactic treatment programs in humans. Comparison of the results using these compounds and the teleost model and screening methods of the present invention would allow a determination as to whether the teleost model and screening methods described herein is predictive of the therapeutic effect in humans; such a comparison would be of benefit in determining whether a tested compound would be useful in programs for therapeutic and/or prophylactic treatment of angiogenesis-related disorders in humans.

A. Proteins

To examine the effects of proteins and protein fragments (and peptides and peptide fragments) on angiogenesis in teleost embryos, proteins (and protein fragments and peptide fragments) were directly injected into the circulation of 24 hour zebrafish embryos. Embryos were collected and dechorionated as described above. The embryos were then sorted into holding ramps made of 1% agarose in embryo water and oriented with the yolk ball projecting up. Microinjection injection was performed as follows: the proteins were suspended in PBS and backfilled into a pulled glass micropipet. The micropipet was then attached to a micromanipulator and a picospritzer (General Valve) attached to a nitrogen tank. Using the micromanipulator, the tip of the micropipet was inserted into the embryo and a small volume of protein solution was expelled from the tip using positive pressure. To determine if our animal model could be used effectively to screen for these compounds, we performed a series of experiments in which we injected one of two different proteins having opposing effects on vessel formation—human endostatin (O'Reilly et al., *Cell* 88 (2):277-285 (1997)) and human vascular endothelial growth factor (VEGF)— into an embryo. Endostatin, a collagen XVIII fragment, is an endogenous protein with potent anti-angiogenic activity. VEGF has been shown to play a critical role in both endothelial cell determination, as well as vessel formation. In preliminary experiments, we injected VEGF protein either into the yolk ball or into the perivitelline space between the yolk and the periderm. Because the second location is in the path of the venous return, proteins end up in the circulation of the embryo. To backfill the injection pipettes, we used a 2 mg/ml solution of VEGF. When VEGF was injected into the yolk, we observed two angiogenic phenotypes: 1) the appearance of long spikes projecting from the subintestinal vessel basket (FIG. 6A); and 2) increased vessel diameters in the subintestinal basket (FIG. 6C). In contrast, injections of VEGF into the perivetellin space led to a disruption of vessel formation (FIG. 6D) and heart development. This is consistent with observations in other vertebrates. Drake et al., *Proc. Natl. Acad. Sci. USA* 92 (17):7657-7661 (1995); Fouquet et al., supra. Endostatin was injected into the zebrafish as was VEGF. In contrast with VEGF, endostatin results ere inconsistent and thus uninterpretable. These experiments demonstrated that changes in the vascular pattern can be induced in our animal model. Moreover, because human proteins produced these effects, these experiments suggested that the mechanisms for angiogenesis in zebrafish and humans are probably similar.

B. Nucleic Acids

To deliver nucleic acids to teleosts, we established a microinjection system. Microinjection of DNA, RNA, and proteins is a well established procedure used in a variety of biological systems, including single cells, frog embryos, mouse embryos, and zebrafish. Westerfield, supra. In the zebrafish, it is possible to load every cell of the embryo by injecting molecules of interest into the yolk of 1-16 cell stage embryos. See Westerfield, supra. Using these standard approaches, several hundred embryos can be loaded in a two-hour period.

3. Evaluation of Biolistic Cell Loading Technology

Biolistic cell loading technology uses coated particles to introduce molecules of interest into tissues and organs of an animal. In this technique, particles coated with the biological molecule are "biolistically" shot into the cell or tissue of interest of the animal using a high-pressure gun. This technique has been used successfully to load primary culture cells as well as whole mouse embryos with large DNA plasmid constructs. Chow et al., *Amer. J. Pathol.* 2 (6):1667-1679 (1998).

With the methods of the invention, biolistic cell loading can be used as an alternative to microinjection techniques to inject compounds into animals, such as, e.g., adult, larval, and teleost embryos. DNA can be regionally administered to the teleost (e.g., introduced to specific locations within the teleost embryo), such as the tail or the dorsal surface of the yolk, prior to, after, or at the time angiogenesis begins.

4. Establishing Parameters for Quantifying and Characterizing the Effects of Compounds on Angiogenesis Activity and Endothelial Cell Toxicity To determine whether a particular compound is of potential therapeutic or prophylactic use, a number of additional parameters, including the Therapeutic Window and the Effective Window can be determined.

A. Therapeutic Window

The Therapeutic Window (TW) is the ratio of the Median Effective Concentration (EC50) to the Median Lethal Concentration (LC50) (i.e., LC50/EC50). LC50 is determined by administering serial dilutions of an agent and determining what proportion of teleosts die at each dilution. LC50 is the concentration needed to cause lethality in 50% of the teleosts. Agents which exhibit a high Therapeutic Window (LC50/EC50), such as 100 or 1,000, are good potential drug candidates because toxicity at the therapeutic concentration is low. Agent concentrations typically range from picomolar to millimolar.

B. Effective Window

The Effective Window (EW) identifies the point during angiogenesis at which a compound is effective. This is determined by exposing embryos to the EC50 of a compound at different stages of angiogenesis, beginning with the 12 somite stage, when angioblasts are first detectable, through the 72 hour stage, when vascularization in the embryo is complete.

In our preliminary studies, we identified a number of compounds which were toxic at various concentrations. It is possible that such compounds are extremely potent and that only low (picomolar) concentrations of such compounds effect angiogenesis. This problem can be addressed by screening compounds for angiogenic effects at concentrations well below the concentration at which induces toxicity.

C. Quantitation of Vessel Growth

While visual comparison of an embryo treated with a compound of interest with an untreated embryo (control) is an effective means for identifying changes in the vessel architecture related to angiogenesis, it does not permit quantitative assessment. As an alternative or in addition to visual comparison, image analysis can be used to quantify and standardize the analysis. A number of commercially available software packages exist (e.g., Image-Pro Plus™, Media Cybernetics; WSR Image Analysis System, WindSword Software Research; MetaMorph®, Universal Imaging Corp.) that permit both distance and area measurements of vessel dimensions and distribution—the parameters used for visual analysis.

D. Evaluation of Additional Markers for Characterizing Angiogenic Activity

Antibody markers that label signaling proteins involved in angiogenic vessel formation in the zebrafish, including VEGF and Ang1 and 2 (Hanahan, *Science* 277 (5322):48-50 (1997)), would assist in identifying compounds that are either agonists or antagonists of the signaling molecules that guide vessel development and patterning. A number of antibody markers have been identified in mouse and are commercially available (Santa Cruz Biotechnology, Inc.). These markers can be tested in teleosts using standard antibody staining protocols. Westerfield, supra. Antibodies can be used in place of RNA probes to simplify the assay procedure.

Briefly, embryos are fixed for 2 hours at room temperature. The embryos are then washed two times in phosphate buffered saline with Tween (PBT) and permeabilized by treatment acetone at −20° C. for 7 minutes. The embryos are rehydrated and then treated with a blocking solution (2% goat serum, 1% bovine serum albumin (BSA) in PBT) for 30 minutes at room temperature. Next, the embryos are soaked in blocking solution containing the primary antibody overnight at 4° C. The embryos are then be washed 5 times in PBT with 1% BSA. The embryos are soaked in blocking solution containing a secondary HRP-conjugated antibody for 4 hours at room temperature. The embryos are then washed and stained by soaking in DAB solution (1 mg diaminobenzidine, 1 ml $0.1M$ $PO_4$ buffer, 1 ml $dH_2O$ and 20 µl of DMSO) for 15 minutes. $H_2O_2$ is then added to the solution for color development. The reaction is stopped by adding PBT.

E. Assays for Compounds that Induce Endothelial Cell Toxicity

Although the strategy of blocking new vessel formation has significant potential for anticancer therapeutics, an alternative strategy is to destroy vessels already present in the tumor. With such a strategy, a compound is administered to the teleost after vessel formation, not prior to vessel formation. It is not known how long compounds persist in the media containing teleost embryos; we assume that effects on blood vessel formation occur relatively soon after administration of the compound. To identify compounds that have toxic effects on blood vessels after formation, we administered compounds to zebrafish embryos at 60 hours of development, when the subintestinal vessels were well established. We then assay the embryos at 72 and 84 hours of development. Compounds were screened for those which caused a loss of the subintestinal vessel staining, as described above.

F. Evaluating the Use of Mutant Fish Lines

Studies suggest that it may be difficult to induce additional vessel growth in a normal animal system. For example, there is evidence of this in the mouse model for ischemia (Couffinhal et al., *Amer. J. Pathol.* 2 (6):1667-1679 (1998)). This issue can be circumvented by performing screens on animals in which vessel development has been impaired. A few genetic mutations exist in the zebrafish that disrupt vessel formation. Examples of such mutations are: 1) gridlock, a localized heritable vascular patterning defect in the zebrafish (Weinstein et al., Cardiovascular Research Center, Massachusetts General Hospital, Charleston, Mass. (1998)), in which vessel formation is normal in the head region and absent in the tail for the first 3-4 days of development, and after ~4 days, collateral vessels begin to appear in the tail; 2) cloche (Fouquet et al., supra, Thompson et al., *Dev. Biol.* 197 (2):248-49 (1998)), in which angioblast development is impaired; and 3) no tail and floating head (Fouquet et al., supra), notocord mutants, in which the formation of the large vessels is blocked. The usefulness of these and other mutant lines are readily evaluated by using the methods for screening compounds for angiogenic activity described herein. Currently, there are no known mutations that cause increases in vessel growth in zebrafish.

G. Assessing Effects of Angiogenic/Anti-Angiogenic Compounds on Organ Systems

The effects of a compound on organ systems other than the vascular system (e.g., kidney, heart, etc.) can be determined by using screening methods described herein. The ability to make such determinations is significant, because in evaluating the potential therapeutic value of any compound identified using the methods of screening compounds for angiogenesis activity, it is important also to identify adverse effects, including adverse effects on other organ systems. The teleost model is ideal for this purpose because many of its organs can be visualized in the transparent teleost embryo by light microscopy (e.g., the heart and the CNS); alternatively, a number of organs of the teleost embryo can be identified by simple staining techniques (e.g., liver, gut, heart, and kidney). For example, cardiac function and liver viability can be assayed. Because the heart is both directly connected to the vasculature and because the heart and the vessels share some of the same cell types, the heart is a likely secondary target of compounds that affect angiogenesis activity. Because the liver is the site of accumulation and metabolism of many compounds, especially toxins, it is an indicator of the toxicity of both the compounds and the breakdown products.

As described above, in our initial studies, we observed that a small number of compounds affected the heart rate of the zebrafish embryo. With six compounds, we observed that the zebrafish heart beat at approximately 1-2 beat(s) per second instead of the normal 4-5 beats per second. To determine if a particular compound affected teleost heart development, or if it acted as an antagonist to the conductivity mechanism, we administered the compound of interest to a zebrafish embryo at 72 hours of development, when a functioning heart and vascular system is present. The embryos were then evaluated 2 hours after the addition of the compound for immediate effects on heart rate and contractility and at 24 hours for effects which might require novel gene or protein expression. If a compound acted as a direct antagonist on either the conduction or contraction machinery of the zebrafish heart, its administration to the zebrafish at any stage would likely show an effect. However, if a compound affected development of the zebrafish heart, its presence should show no effect at the later stage of development.

In addition to examining the heart rate and contractility, we also examined the structure of the heart both by visual inspection (Stainier et al., *Development* 123:285-92 (1996)) and by staining the heart with antibodies against tropomyosin and cardiac myosin heavy chain (Stainier and Fishman, *Trends Cardiovasc. Med.* 4:207-212 (1994), which allowed identification of the atrium and the ventricle—the two chambers of the fish heart. Briefly, embryos were fixed for 2 hours at room temperature. The embryos were then washed two times in PBT with Tween and permeabilized by treatment acetone at −20° C. for 7 minutes. The embryos were rehydrated and then treated with a blocking solution (2% goat serum, 1% bovine serum albumin (BSA) in PBT) for 30 minutes at room temperature. Next, the embryos were soaked in blocking solution containing the primary antibody overnight at 4° C. The embryos were then washed 5 times in PBT with 1% BSA. The embryos were subsequently exposed to the appropriate fluorescent conjugated secondary antibodies for detection. The embryos were analyzed using an epifluorescence microscope. This method uses a particular means of detection;

alternative secondary reagents and visualization (or detection) methods, including, e.g., chromogenic, radiographic or other methods, may be used.

III. Methods of Screening an Agent for an Effect on Cell Death Activity

A. Cell Death

The death of cells of multicellular organisms may result from natural processes or external non-physiological causes. Two types of cell death are known: necrosis and apoptosis. Necrosis is the pathologic death of living cells which results from acute, non-physiological injury to the cells. Hetts, *J. Amer. Med. Assoc.* 279 (4):300-07 (1998). Necrosis may result from the exposure of a cell to a number of differing conditions, including toxins, severe hypoxia, massive insult or physical injury, or conditions of adenosine 5'-triphosphate (ATP) depletion. Id. Necrosis occurs, for example, in the center of infarcted tissue in an ischemic stroke or at the center of toxin action. Id. Necrotic cells swell and lyse, thereby releasing their nuclear contents into the surrounding intercellular regions and causing an inflammatory response. Id. Significantly, however, necrosis is not the only mechanism by which cells die.

Apoptosis, or programmed cell death, is a naturally-occurring physiological process that plays an important role in modeling tissues during development. Kerr et al., *Br. J. Cancer* 26:239-257 (1972); Clarke, *Anat. Embryol.* 181:195-213 (1990). Apoptosis ensures that a balance is maintained between cell proliferation and cell differentiation in nearly all self-renewing tissues of multicellular organisms. Apoptosis allows the elimination of cells that are, for example, no longer required, are produced in excess, have incurred damage, or have developed improperly. Numerous types of cells undergo cell death through by apoptotic processes. Hetts, *J. Amer. Med. Assoc.* 279 (4):300-307 (1998). Apoptotic cells undergo a number of characteristic changes, including chromatin condensation, nuclear fragmentation and cytoplasmic blebbing. Liepins and Bustamante, *Scanning Microsc.* 8:631-641 (1994). This programmed cell death mechanism is precise and predictable, and the stages and genes that govern cell death are highly conserved among multicellular animals.

Apoptosis appears to be directed by the dying cells themselves, and during development, it is involved in maintaining the appropriate cell number and cell type in a given organ or tissue. Some apoptotic events are believed to be regulated by limiting the amount of growth or survival factors. It can also be triggered in response to external stimuli, including, for example, radiation, hyperthermia, hormone withdrawal, immune reactions, radiation, chemotoxins, temperature extremes, growth factor deprivation, and infection by some viruses. Thompson, *Science* 267:1456-1462 (1995).

Abnormal regulation of apoptosis has been implicated in the onset and progression of a broad range of diseases resulting from inappropriate cell death or inhibition of cell death. Apoptotic dysregulation has been implicated, for example, in some types of cancer cells which survive for longer periods than do corresponding normal cells. It is believed that the suppression or failure of the apoptotic mechanism allows certain cancer cells to undergo further mutations leading to a transformed or cancerous state. Hetts, *J. Amer. Med. Assoc.* 279 (4):300-307 (1998). Uncontrolled apoptosis has also been implicated in other disorders, including neurodegenerative disorders, lymphoproliferation, autoimmune diseases, and heart and renal diseases. Id.

In addition, many therapeutic approaches for diseases (e.g., cancer, heart disease, and neurodegenerative diseases), including various chemotherapies and organ transplantation, have been shown to induce apoptosis in normal cells. Id.

Indiscriminate inhibition of apoptosis can lead to widespread hyperplasia, and inappropriate promotion of apoptosis may lead to undesirable tissue degeneration, underscoring the need for more precise assays for studying cell death. Multiple pathways to apoptosis mean that different therapeutic approaches are possible for treating abnormal apoptotic regulation, demonstrating the need for assays for screening compounds for their ability to cause or suppress cell death.

Understanding of the mechanisms of cell death activity, including apoptosis, would facilitate the development of therapeutic compounds that either stimulate, trigger, or initiate cell death, or, alternatively, suppress, inhibit, or block cell death. For example, the discovery of signaling proteins and their corresponding receptors presents the opportunity for the development of tools for correcting the apoptotic cellular machinery when it goes awry or harnessing its potential for cell killing. Because abnormal regulation of apoptosis has been implicated in the onset and progression of a wide range of diseases, many disorders can now be classified based as to whether they are associated with too much or too little apoptosis. In particular, a number of approaches aimed at cancer therapy are currently under investigation, since it is known that tumor cells proliferate when the apoptotic engine fails to operate. Potential methods of repair include finding chemicals that target receptors to restore the apoptotic function in tumor cells, and inducing apoptosis in a tumor's developing blood vessel.

Improved understanding of the molecular apoptosis pathways may also stimulate development of novel non-pharmaceutical therapies. For example, an adenovirus that is only able to replicate in and kill p53-deficient cells is currently in Phase I clinical trials as a possible antitumor agent that should kill only p53 deficient tumor cells, leaving normal cells unaffected. A compound that limits coronary damage if injected after a heart attack is also presently under investigation, underscoring the potential for the development of molecular approaches utilizing small molecules that both inhibit and induce apoptosis selectively. Improved understanding of the physiological process of apoptosis at the molecular level would provide insight into disease pathogenesis and open new avenues for developing diagnostic, prognostic, and therapeutic tools.

The genetics and molecular mechanisms of apoptosis were characterized in the late 1980s and early 1990s in studies using the nematode worm, *C. elegans*. Although the nematode has many advantages as a model system, including evolutionary conservation of much of the signaling pathway involved in apoptosis (see, e.g., Steller, *Science* 267:1445-49 (1995)), it is not the optimum model for an understanding of vertebrate cell death activity and disease states. Vertebrates are much more complex and have multiple apoptosis pathways comprised of many more signaling molecules. There are currently no rapid in vivo assays of screening a compound for its effect on cell death activity, such as apoptosis, in vivo in a vertebrate system. It would therefore be desirable to provide a rapid in vivo method of screening a compound for its effects on cell death activity, including apoptosis and necrosis, in a vertebrate system.

Currently, there are two primary approaches for detecting cell death activity in vertebrates hosts. The first approach uses standard cells culture techniques and typically relies on standard microplate plate readers to detect the death of cells cultured from an organism. A major drawback of the cell culture assay format is that it does not permit analysis of the effects of a compound on cell types that have not been cultured (i.e., other cell types) or on one or more tissues or organs or an intact, whole host in vivo. Furthermore, such an assay format does not permit simultaneous monitoring of cell death activities in multiple tissues, organs, or systems of a live host or monitoring over time.

A second approach to detecting cell death activity utilizes a histochemical staining technique, designated terminal deoxyuridine nucleotide end labeling (TUNEL) to detect dead or dying cells (e.g., apoptotic cells) in sectioned tissues of vertebrate embryos. Gavrieli et al., *J. Cell. Biol.* 119:493-501 (1992). Unfortunately, with this approach, only a single time point in the life cycle of the host can be examined; the death of cells in various tissues or organs over a period of time cannot be monitored. Nor can side effects due to an administered compound be monitored simultaneously or over time. Because many diseases occur in stages, the ability to examine changes in the pattern of cell death activity caused by a compound, the duration of direct and side effects of the compound of multiple tissues, would represent a significant improvement over current methods.

Gene products that regulate cell death activity, including apoptosis, are excellent targets for therapeutic intervention in alleviating many disease processes. Few such therapeutic gene products currently exist. It would be also desirable to provide a method of screening a compound for its potential therapeutic effect on cell death activity. Such methods would be of benefit in alleviating diseases resulting from abnormal cell death processes, including those resulting from inappropriate cell death or inhibition of cell death (e.g., apoptotic dysregulation).

B. Methods of Screening Agents for Cell Death Activity

The present invention provides methods of screening an agent for an effect on cell death activity in a vertebrate animal, such as a teleost, in vivo or in vitro in cells of the animal. Cell death activity is the ability or capacity of an agent to enhance, stimulate, inhibit, or block cell death in an animal, tissue, organ, or cell in response to administration of an agent. Cell death activity is assessed relative to contemporaneous and/or historical control teleosts (or tissues, organs, or cells thereof) to which the agent has not been administered. Such methods are useful for screening an agent for its ability to trigger, enhance, suppress, or eliminate apoptotic or necrotic processes. Identified agents can be used potentially in therapeutic or prophylactic treatment of diseases which result from abnormal cell death processes or diseases which would benefit from the elimination or controlled death of targeted cells or tissues.

Some such methods comprise administering the agent to a whole teleost in vivo and detecting a response in the teleost indicating an effect on cell death activity. Other such methods comprise administering the agent in vitro to a culture of cells of a teleost and detecting a response in the cells indicating an effect on cell death activity. In some such methods, the detected response is an increase or initiation of cell death activity. In other methods, the detected response is a decrease or suppression of cell death activity. In some methods, the response is an increase or decrease in apoptotic activity. An effect on apoptotic activity can be measured by detecting a response indicating such an effect; the response can be, for example, an increase or triggering of apoptosis or a decrease or suppression of apoptosis. An increase in apoptotic activity generally comprises an increase in the death of cells in a tissue or organ of the animal.

Typically, the animal is a teleost, such as a zebrafish. Usually, the teleost is transparent. The teleost can be in embryonic, larval, or adult form.

Alternatively, an agent can be screened for an effect on necrotic activity in vivo in a teleost by administering the agent to the teleost in vivo and detecting a response in the teleost indicating an effect on necrotic activity. An agent can also be screened for an effect on necrotic activity in vitro by administering the agent in vitro to cultured cells of a teleost and detecting in the cells indicating an effect on necrotic activity. In both such methods, the response can be an increase or decrease in necrotic activity.

The effect of a particular agent on the entire, intact teleost and/or one or more organs, tissues, or systems of the teleost (e.g., the cardiovascular system, the enteric system, and the musculature) can be measured in vivo or in vitro in cells of the teleost and, if desired, over a period of time and/or at selected time intervals. Responses in combinations of organs and/or tissues can be detected simultaneously or separately; such analyses can be performed over time at predetermined time intervals. These methods can also be used with isolated cells or cell lysates.

Cell death activity can be detected in vivo or in vitro by using at least one of a variety of techniques, including, e.g., fluorescence microscopy, light microscopy, digital image analyzing, or standard microplate reader techniques (colorimetry, fluorometry, including time-resolved fluorometry, and chemiluminescence), antibody staining of proteins, changes in enzyme levels or enzymatic activities in the whole teleost, or tissues, organs or cells of the teleost, and changes in protein distribution temporally and spatially within the animal. The response can also be discriminated and/or analyzed by using pattern recognition software. Thus, for example, an increase in apoptotic or necrotic tissue can be analyzed in a zebrafish by using such techniques.

Fluorescence-based detection techniques and fluorescence microscopy can also be used to detect the effect of an agent on cell death activity in an animal, such as a teleost. For example, teleosts can be stained with a membrane-impermeant, nuclear-staining fluorescent dye which permits detection of cell death activity (e.g., apoptosis or necrosis). A variety of fluorescent dyes can be used. Preferred dyes include those of the unsymmetrical cyanine dye family (such as quinolium dyes, e.g., benzothiazolium-4-quinolium dyes (Molecular Probes)), including derivatives, analogs, and substituted or unsubstituted forms thereof. Such dyes are generally discussed in U.S. Pat. No. 5,658,751, which is incorporated herein by reference in its entirety for all purposes. A number of these dyes are commercially available.

These dyes, including monomeric cyanine dyes (such as benzothiazolium-4-quinolium), cannot pass through intact membranes of cells of live embryos. However, these dyes can enter dead or dying cells whose membranes have become discontinuous or disrupted (a characteristic of cells undergoing cell death, Liepins and Bustamante, *Scanning Microsc.* 8:631-41 (1994)). Notably, the cytoplasmic blebbing and other properties in the membrane characteristic of a dead, dying cell, or apoptotic cell permit such dyes to enter the cell.

Upon passing through the cell membrane, monomeric cyanine dyes (e.g., benzothiazolium-4-quinolium) intercalate into the DNA of the dead or dying cells. The dense chromatin and nuclear fragmentation provide an ideal environment for dye intercalation and signal amplification. Singer, *Biotechnol. Intl.* 1:267-276 (1997). Upon intercalating into the DNA, the dye becomes intensely fluorescent, allowing for rapid detection of the labeled cells using simple fluorescence microscopy. Notably, when concentrated in DNA, the fluorescent signal of benzothiazolium-4-quinolium dye is amplified up to 400 fold. Serbedzija et al., *J. Neurobiol.* 31 (3):275-

282 (1996). The magnitude of the signal serves as a measure of the number of apoptotic or necrotic cells.

Notably, the in vivo methods of screening agents for cell death activity of the present invention provide a more sensitive and accurate detection and measurement of cell death in whole embryos in vivo than permitted by existing approaches. Other fluorescent markers of cell death, such as Acridine Orange, pass through the membranes of cells of live embryos much more readily and fluoresce under a variety of conditions than do monomeric cyanine dyes, such as benzothiazolium-4-quinolium dyes. For example, Acridine Orange fluoresces when bound to nucleic acids and when localized in subcellular compartments such as lysozymes. It has also been reported that Acridine Orange does not bind effectively with DNA under some circumstances, including chromatin compaction which is sometimes associated with apoptosis. Thus, Acridine Orange and similar such dyes do not provide as specific a marker of cell death as a benzothiazolium-4-quinolium dye.

Monomeric cyanine dyes (e.g., benzothiazolium-4-quinolium dyes) also provide a higher signal-to-background when bound to nucleic acid than do other fluorescent markers of cell death, such as Acridine Orange. In addition, the fluorescence emission spectra of benzothiazolium-4-quinolium dyes are typically narrower (i.e., emission occurs over a narrow wavelength emission band) than are the emission spectra of other fluorescence labels, such as, e.g., Acridine Orange, which has a very broad fluorescence emission spectrum. The characteristic emission spectra of monomeric cyanine dyes permit the use of two or more additional fluorescence labels simultaneously in conjunction with the quinolium dye, thereby allowing characterization of multiple types of physiological events within the same or different organs or tissues. A broad emission spectrum (e.g., Acridine Orange) severely limits the ability to use multiple fluorescent labels for screening methods described herein due to overlap between the fluorescence emission spectra of the labels. Thus, with the methods of the invention described herein, more than one fluorescent dye can be used together for monitoring multiple cellular and/or molecular phenomena in response to an agent administered to the animal in vivo simultaneously over time. Dyes can be selected to have emission bands that match commercially available filter sets such as that for fluorescein or for detecting multiple fluorophores with several excitation and emission bands.

Furthermore, in contrast with other fluorescent markers of cell death, benzothiazolium-4-quinolium dyes are not toxic; thus, apoptotic or necrotic effects in a living teleost to which the dye has been administered can be monitored over a significant time period, without risk that the teleost will be adversely affected by the dye. In contrast, assays using other types of markers of cell death require that the host be sacrificed and fixed (e.g., TUNEL labeling).

The fluorescent dye is typically administered to the teleost by adding the dye to the media containing the teleost. Alternatively, the dye can be injected directly into the teleost. The dye is typically administered prior to administration of the agent to be screened for cell death activity. This procedure provides superior results over existing approaches, because we have found that if the dye is added after apoptosis has been induced, the dye is less effective in labeling dead or dying cells. One of the apoptotic mechanisms (e.g., the polymerization of components of intracellular membranes and the plasma membrane) may make it difficult or impossible for the dye to enter the cell. As a result, an apoptosing cell may not be labeled. By applying the dye prior to application of the agent, this problem is avoided. The fluorescence emission of the dyes is monitored by using standard fluorometric techniques, including visual inspection, CCD cameras, video cameras, photographic film, or the use of current instrumentation, such as laser scanning devices, fluorometers, photodiodes, quantum counters, photon counters, plate readers, epifluorescence microscopes, scanning microscopes, confocal microscopes, or by means for amplifying the signal, such as a photomultiplier tube.

Unlike other known dyes which involve laborious labeling procedures (e.g., TUNEL labeling), the benzothiazolium-4-quinolium dyes are particularly suitable for high throughput, automated screening methods. The higher signal-to-noise ratio inherent in these dyes and our superior method of administering the dye prior to administration of the agent to be screened for apoptosis enable automated data acquisition, more accurate quantitation of the collected data (e.g., digital imaging), and the possibility of feature extraction/image segmentation of acquired data. These features allow mapping of the apoptosis signal in space/time dimensions that can be correlated with fate map coordinates of the specific teleost's fate map. Such information permits further characterization of the screened agents.

As noted above, cell death activity (e.g., apoptosis and necrosis) can also be detected by digital imaging. Digital imaging is an indispensable tool for biological research due to several advantages when compared to the human eye. Digital imaging involves the collection of images using a charge-coupled device (CCD). The higher sensitivity imaging detector enables one to visualize very low light objects which are not detectable by the unaided human eye. The spectrum sensitivity of the human eye is limited from 400 to 700 nm. In contrast, the spectrum sensitivity range of imaging detectors is more broad, and signals from the range of x-ray to infrared can be detected. Combining digital mapping and pattern recognition software enables the quantification and comparison of multiple data sets and facilitates comparison of contemporaneous and historical controls with experimental teleost animals.

The present invention also provides methods of screening a compound for its effect on cell death activity in vivo in a teleost or in vitro in cells of the teleost over time. Such methods comprise administering the compound to the teleost in vivo or in vitro in cells thereof, detecting a response in the teleost indicating an effect on cell death activity, and further detecting a response in cell death activity in the teleost after a predetermined period of time or time interval. The period of time, which is selected by the practitioner, is typically sufficient for detectable cell death to occur in the presence of the compound. In addition, multiple time points can be examined to detect any pertinent physiological activity. Some such methods further comprise detecting a response in cell death activity (e.g., apoptosis) after a second predetermined time interval using the detection techniques described herein. Such methods are useful in evaluating the effect of an agent (e.g., chemical compound, drug, environmental agent, agricultural compound, toxin, pharmaceutical, cosmeceutical, etc.) on tissues and organs over time in the intact, live teleost.

In yet another aspect, the present invention provides methods of screening an agent for an effect on cell death activity in vivo or in vitro, as described above, which further comprise detecting an increase or decrease in cell death activity in more than one tissue or organ of the teleost simultaneously. In some such methods, the increase or decrease in cell death activity is detected simultaneously in more than one tissue or organ at predetermined time intervals. The effect of a particular compound on various cells, tissues, and organs of the embryo can be monitored and assessed over time. Cell death activity in multiple tissues or organs can be detected by using the detection techniques described throughout this specification.

The present invention also provides automated methods of screening a compound for an effect on cell death activity in vivo or in vitro. The methods of the invention can be performed using a standard microplate well format, with one or more whole teleosts per well of the microplate. This format permits screening assays to be automated using standard microplate procedures and plate readers to detect cell death in the zebrafish in the wells. With this setup, the effect of a specific compound on a large number of teleosts can be ascertained rapidly. In addition, with such format, a wide variety of compounds can be rapidly and efficiently screened for their respective effects on the cells of teleosts (e.g., teleost embryos) contained in the wells. Both sample handling and detection procedures can be automated using commercially available instrumentation and software systems for rapid reproducible application of dyes and compounds and automated screening of target compounds.

The contemporaneous and/or historical control teleosts (which includes teleost tissues, organs, or cells) used with these methods can include those in which at least one inhibitor of apoptotic molecular mechanisms (including, e.g., known or specific inhibitors of apoptotic mechanisms) has been administered to the teleost (or tissues, organs, or cells thereof) at specific stages of development, thereby generating a particular phenotype, such as tissue malformation (e.g., expansion of the central nervous system; malformation of the cloacal/anal pore region; hyperproliferation of cells in any tissues). Agents can then be screened for the ability to induce the same or similar phenotype (i.e., phenotypic response). With such methods, the agent is administered to the teleost as described above; the phenotypic response in the teleost can be detected visually by light microscopy, by fluorescent labeling with unsymmetrical cyanine dyes discussed above, or by labeling with in situ hybridization or antibody staining for selected cell types. Using these types of controls, the agents can be screened for the ability to "phenocopy" the effect of the loss of molecular function(s) or mechanism(s) induced by the apoptotic inhibitor. Phenocopying in the experimental teleost (or tissues, organs, or cells thereof) relates to the duplication or mimicking of the same or similar phenotype observed in the control.

The present invention includes screening methods which rely on detecting enzymatic activity associated with apoptosis. In one aspect, the invention provides methods of screening an agent for apoptotic activity which comprise administering the agent to a teleost and detecting a response in the teleost indicating apoptotic activity by detecting the activity of an enzyme (e.g., cleavage of caspase substrate).

Caspase enzymes, for example, are well characterized proteases that function as triggers, effectors, or mediators in a number of apoptotic pathways. The fluorogenic caspase substrate can be introduced into the teleost by a variety of methods, including, e.g., by injection into the teleost, by dissolving the substrate in the medium containing the teleost. The manner of introduction of the substrate depends upon the particular type and nature of reporter substrate design (e.g., small molecule, plasmid). The fluorogenic caspase substrate can be introduced at the time or, after, or, usually, prior to administration of the agent. Caspase activity (e.g., cleavage of caspase substrate) can be measured by using, for example, commercially available colorimetric or fluorometric enzymatic assays or by using antibodies which detect cleaved substrates (e.g., M30 CytoDEATH antibody; Boehringer Mannheim). Specific patterns of embryo dysgenesis result from the inhibition of naturally occurring apoptotic events during development. Inhibition of caspase activity can cause specific morphological effects including tissue malformation. Such methods can be conducted in vivo using whole teleosts or in vitro using cells of the teleost. Such methods are useful for identifying agents having apoptotic activity that may have potential therapeutic or prophylactic use for treating a variety of diseases, such as cancer.

C. Screening Agents for Cell Death Activity and/or Angiogenesis Activity and/or Toxic Activity Simultaneously The methods for screening agents for cell death activity can be combined with other methods of the present invention, including methods of screening agents for angiogenesis activity (Section II) or toxic activity (Section IV). Because teleosts are transparent, it is possible to assess effects of cell death activity, angiogenesis activity, and/or toxic effects in teleosts in response to an agent simultaneously. Responses can be monitored in one or more tissues or organs and at predetermined time intervals.

As noted previously, these combined methods are useful in assessing multiple effects of an agent, including desired and undesired responses (such as detrimental side effects) and dose levels of the agent effective to promote one activity without promoting the other. The ability to assess multiple activities and responses in an animal due to the administration of an agent is of particular benefit in identifying potential therapeutic compounds and assessing their side effects. Pathological regulation of apoptosis, for example, is associated with a wide variety of human diseases including cancer, heart disease, neurodegenerative disorders, and immune, renal and viral-induced diseases. Essentially all cells are poised to commit suicide from the earliest stages of development. Thus, it is imperative that drugs be exactingly targeted. A balance must also be achieved during treatment with drugs such that only a negligible level of cell death and toxic effects in non-targeted tissues or organs. The combined methods of the invention are useful in assessing the specificity and extent of cell death and deleterious and toxic effects of potential drugs in particular organs and tissues or within the whole animal.

A variety of techniques can be used together or separately to analyze multiple activities/responses, including, e.g., fluorescence microscopy, light microscopy, digital image analyzing, standard microplate reader techniques (colorimetry, fluorometry, including time-resolved fluorometry, and chemiluminescence), radiometric analysis, in situ hybridization, changes in enzymatic activity and levels in the whole teleost, or tissues, organs or cells of the teleost, antibody staining of specific proteins, changes in protein distribution temporally and spatially within the animal, etc.

In one aspect, the present invention provides methods of screening an agent for an effect on cell death activity in vivo or in vitro as described above which further comprise screening the agent for an increase or decrease in toxic activity by detecting a response in the teleost indicating an increase or decrease in toxic activity. In another aspect, the invention provides methods of screening an agent for an effect on cell death activity in vivo or in vitro as described above which further comprise screening the agent for an increase or decrease in angiogenesis activity by detecting a response in the teleost indicating an increase or decrease in angiogenesis activity.

With such combination methods, the contemporaneous and/or historical control teleosts (or tissues, organs, or cells thereof) for the cell death activity screens can include those described above in which at least one inhibitor of apoptotic molecular mechanisms has been administered to the teleost (or tissues, organs, or cells thereof) at specific stages of development, thus generating a particular phenotype. Agents can then be screened for the ability to induce the same or similar phenotype.

Examples

1. Induction of Cell Death in Zebrafish Embryos

Treatment of zebrafish with retinoic acid (RA, vitamin A acid) leads to increased apoptosis in a number of developing tissues, including the neural tube. Ellies et al., *Mech. Dev.* 61:23-36 (1997). Retinoic acid is known to regulate the expression of the Hox gene family. Members of this gene family have been shown to confer positional identity to cells during development. Hunt et al., *Nature* 353:861-864 (1991). Retinoic acid induced apoptosis may be a result of a change in a cell's identity, or a direct effect on the apoptosis pathway. In either case, application of retinoic acid is different stages of development leads to characteristic patterns of cell death (see, e.g., FIGS. 10A-10B).

Normal apoptosis occurs in the zebrafish embryo throughout the complete morphogenesis period of 72 hours; however, high levels of apoptosis can be induced in the 24-hour embryo by administration of retinoic acid to the embryo. In methods of the present invention, retinoic acid is used to generate a reproducible pattern of cell death for assay optimization. Where cell death activity involves apoptosis, assays of the present invention can include a comparison of the effects of apoptosis induced by retinoic acid in zebrafish embryos in vivo (i.e., control) with the effects of a test compound on zebrafish embryos in vivo. The accuracy of such assays can be confirmed by performing the TUNEL assay (described above) on the same zebrafish embryos.

A method of screening a test compound for an effect on cell death activity (e.g., apoptosis or necrosis) in vivo in vertebrate embryos is depicted below:

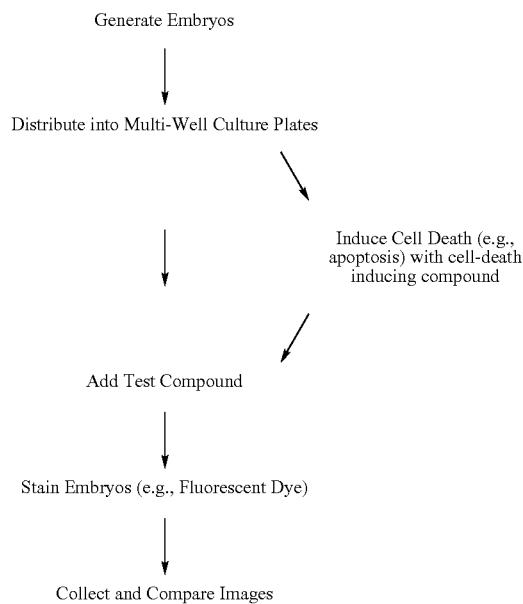

This method can be readily automated using known automated software and instrumentation systems.

With this method, zebrafish embryos are first generated by natural mating and then collected and placed in egg water prepared by combining 5 gram (g) of Instant Ocean Salt with 3 g of calcium sulfate in 25 liters of distilled water. Embryos are then be treated with a 2 mg/ml pronase solution for 1 minute at 28° C. and washed three times in egg water to remove the chorions. The embryos are maintained in the egg media throughout the experiments. Because the zebrafish embryo receives nourishment from an attached yolk ball, no additional maintenance is required. After 12-14 hours of development, embryos are treated with 0.1 µM to 1 µM retinoic acid in 0.5% dimethyl sulfoxide (DMSO) for 2 hours to induce cell death in the forebrain and hindbrain of the zebrafish. Cell death in the forebrain and hindbrain can be detected at approximately 24 hours of development (see FIGS. 10A-10B). Embryos are then be washed twice in egg water and maintained at 28° C. until they reach the appropriate developmental stage for staining.

2. Fluorescent Detection of Cell Death in Live Zebrafish Embryos

To identify cells undergoing cell death, embryos are stained with a membrane-impermeant, nuclear-staining fluorescent dye, such as a dye of the benzothiazolium-4-quinolium dye family. Benzothiazolium-4-quinolium dyes are soluble in DMSO and can be administered to the zebrafish by adding the dyes directly to the medium, which usually contains DMSO. Zebrafish tolerate high levels of DMSO well.

Zebrafish embryos are generated and the chorions are removed as described above. The embryos are divided into 4 groups:

1) Untreated, unstained embryos (autofluorescence+cell death)
2) Treated, unstained embryos (autofluorescence w/induced cell death)
3) Untreated, stained embryos (fluorescent dye+normal cell death)
4) Treated, stained embryos Embryos from group 2 and 4 are treated with retinoic acid at 12 hours of development as described above. At 20 hours of development, individual embryos from each group are placed in single wells of a multi-well culture plate (e.g., 96-well culture plate) in 100 microliter (µl) of egg water. Because zebrafish embryos develop normally in 100 µl of water, test compounds and dyes can be easily added directly to the medium in which the fish is maintained. In this procedure, the fluorescent dye is added to the media of embryos from groups 3 and 4 in 1/5, 1/10, 1/50, 1/100 and 1/200 dilutions. For each dye concentration, embryos are collected at 30-minute intervals for 4 hours. The embryos are then washed twice in tank water for 5 minutes. The embryos are viewed using an epifluorescence microscope equipped with a CCD camera for low light level detection. Images are collected and compared using standard software (e.g., Photoshop, Adobe System). Group 1 embryos reflect the normal level of autofluorescence. Group 2 embryos reflect autofluorescence caused by the apoptotic cells or retinoic acid. Group 3 embryos indicate normally occurring cell death. Group 4 embryos provide the primary baseline for assay development.

To confirm the accuracy of fluorescent detection of cell death (e.g., apoptosis), a conventional TdT-mediated dUTP-biotin nick end labeling assay (designated terminal deoxyuridine nucleotide end labeling or "TUNEL") is performed on the same embryos (Groups 1-4, described above). The TUNEL assay is described in Gavrieli et al., *J. Cell. Biol.* 119:493-501 (1992). This assay is a method of in situ labeling of DNA breaks in nucleic, in tissue sections processed through standard histopathological procedures. The method employs terminal deoxynucleotidyl transferase (TdT) to end label DNA fragments within the nucleic of apoptotic cells. TdT specifically binds to the 3'-OH ends of DNA, ensuring a synthesis of a polydeoxynucleotide polymer. After exposure of nuclear DNA on histological sections by proteolytic treatment, TdT is used to incorporate biotinylated deoxyunridine at sites of DNA breaks. The resulting signal is amplified by avidin-peroxidase, enabling conventional histochemical identification by light microscopy.

Because the zebrafish embryos are transparent, TUNEL staining can be done in whole mount format. Whole embryos are fixed in 4% paraformaldehyde overnight and stained using the TUNEL procedure described by Gavrieli supra. Embryos are rinsed in ddH20 (double distilled water) and 10 mM Tris-HCl, pH 8. Embryos are then pre-treated with TdT buffer (30 mM Trizma base, 140 mM sodium cacodylate, pH 7.2, 1 M cobalt chloride ($CoCl_2$)) for 3 hours at 37° C. Embryos are then washed 3 times for 30 minutes in phosphate-buffered saline with 0.1% Tween (PBST) at pH 7.2. PBST is then replaced with a reaction mixture of TdT buffer containing 40 µM bio-16-dUTP (Enzo Biochemicals) and 0.3 Units/µl of TdT enzyme (IBI/Kodak) overnight at 37° C. The reaction is terminated by washing the embryos in 2× saline-sodium citrate buffer (SSC). Embryos are then rinsed in PBS. Biotinylated nucleotides are detected using a streptavidin complex conjugated to horseradish peroxidase (HRP) according to the manufacturer's protocol (A+B reagents, Vectastain). HRP is detected by incubating the sections in a 3,3'-diaminobenzidine (DAB) solution containing 500 µg/ml DAB, 0.2% $CoCl_2$, 0.2% $NiSO_4(NH_4)2SO_4$-$6H_2O$ and 10% $H_2O_2$ in 1 M phosphate buffer, pH 7.4. Stained embryos are visualized on a compound light microscope.

As an additional test of our cell death detection method, we also examined the ability of the dye to label cells in embryos treated with Ibuprofen, a cyclooxygenase inhibitor, which causes a characteristic pattern of cell death. This pattern consists of a posterior to anterior progression of dying cells as indicated by a progression of opacity changes in the cells of the embryo.

Embryos as 24 hours of development were pretreated for 1 hour with a 100 nanomolar concentration of the fluorescent dye (e.g., benzothiazolium-4-quinolium dye) in embryo media. The embryos were then exposed to 100 µM of Ibuprofen by addition to the media and examined by light and epifluorescence microscopy every 15 minutes for 2 hours. Control embryos were pretreated with the same concentration of dye, but were not exposed to the Ibuprofen. Within 1 hour, fluorescently labeled cells were detected in the posterior tip of the tail in the experimental embryos, but not in the control embryos. At 1 hour and 30 minutes, labeled cells were detected in a large patch, extended from the tip of the tail to the level of the anus. By two hours, fluorescently labeled cells could be seen throughout the embryo, In contrast, no such pattern of labeled cells was observed in the control embryos. This pattern of fluorescently labeled cells was identical to the pattern observed for the opacity changes in the embryo.

3. Rescue of Induced Cell Death Activity

To determine if the teleost model could be used to screen for compounds which blocked or reduced cell death activity, embryos were microinjected with a Caspase 3 inhibitor (Calbiochem #264155) prior to exposure to Ibuprofen.

Specifically, embryos at 24 hours of development were dechorionated and microinjected with either 25 µM Caspase 3 inhibitor or PBS into the yolk. At 26 hours of development, embryos were exposed to 100 µM Ibuprofen by addition to the media. At one hour, opaque cells were observed in embryos injected with PBS, but not in embryos injected with the Caspase inhibitor. At two hours after the addition of Ibuprofen, embryos injected with PBS were completely opaque. In contrast, embryos injected with the Caspase inhibitor were still transparent, however, opaque cells had begun to appear in the most posterior region of the tail in these embryos. By 24 hours after the introduction of Ibuprofen, all of the experimental embryos were dead.

4. Screening Compounds for an Effect on Cell Death Activity

A wide variety of compounds can be analyzed for their potential effect on cell death activity (e.g., apoptotic or necrotic activity) by using methods of the present invention. Therapeutic or prophylactic drugs, chemicals, toxins, and pharmaceuticals are among those that can be tested for their effects on cell death activity, including their ability to inhibit or trigger apoptosis.

Compounds to be screened can be obtained from various sources, including the National Cancer Institute's Natural Product Repository, Bethesda, Md.

A compound to be tested can be administered to a teleost (e.g., zebrafish) in vivo by dissolving the compound in the solution or medium containing the teleost. The compound is absorbed by the teleost. Alternatively, the compound can be injected directly into the teleost.

When screening compounds for their effects on apoptotic activity, it is useful to compare an assay utilizing teleost embryos to which the test compound has been administered with embryos to which retinoic acid has been administered. For such comparative assays, teleost embryos are divided into four groups:
1) No retinoic acid, no test compound (normal control)
2) Retinoic acid, no test compound (induced cell death control)
3) No retinoic acid, test compound
4) Retinoic acid, test compound Screening methods are performed as described above. Specifically, zebrafish embryos belonging to groups 2 and 4 are treated with retinoic acid under identical conditions, as described above, to induce the same degree of apoptosis. Zebrafish embryos belonging to groups 3 and 4 are then exposed to the test compound. All embryos are then stained with the dye and images are collected using an epifluorescence microscope (NIKON E600) equipped with a CCD camera for low light level detection. Zebrafish embryos from each group are then compared using image and analysis software. Group 1 embryos serve as (normal) control embryos. Group 2 embryos provide a control for the level of apoptosis induced by retinoic acid. Group 3 embryos demonstrate the ability of the test compound to induce apoptosis. Group 4 embryos represent the ability of the test compound to induce or suppress apoptosis relative to retinoic acid. Absolute changes in the signal area of apoptosis and the number of apoptotic cells are used to determine if the test compound has had an effect on apoptotic activity.

Notably, methods of the present invention are performed in live, transparent teleost embryos. The effect of a test compound on cell death activity (e.g., apoptotic or necrotic activity) in vivo can be determined over time by examining the above-identified zebrafish embryo groups at 24-hour intervals, for a period of up to 4 days. The effect of a compound on the death of cells of a particular organ (e.g., brain) or tissue of a teleost can be examined over time. Organ-specific and tissue-specific patterns of cell death can be identified. Furthermore, the persistence and duration of the effect of the compound can be determined by methods of the invention. In addition, the effect of a compound on either or both the entire whole embryo or specific organs and tissue systems (e.g., the cardiovascular system, the enteric system and the musculature system) can be determined in vivo simultaneously or independently. Because teleosts, such as zebrafish, are easy to generate and the assay is readily reproducible, a large number of test compounds can be easily and quickly screened for their respective effects on and regulation of cell death activity, including apoptosis and/or necrosis.

With methods utilizing benzothiazolium-4-quinolium dye, one cannot distinguish between a potential effect a particular compound may have on apoptotic processes and necrotic processes. In a developing embryo, necrotic cell death rarely occurs unless the embryo is damaged by nonphysiological injury caused by, for example, physical manipulation. To eliminate nonphysiological injury to an embryo (and thus to eliminate any cell death resulting from necrosis), dechorionated embryos are maintained in agar coated wells. The agar coating prevents abrasions to the ectoderm of the embryos. Such abrasions can occur when the embryos contact plastic surfaces. To prevent further nonphysiological injury to embryos, each embryo is not handled once it is placed into a well of the multi-well culture plate. Staining, compound exposure, and observations on the embryos can all be performed in the multi-well culture plate without manipulating the embryos, thereby reducing the possibility of necrotic damage to the embryos. Specific fluorogenic substrates which report enzymatic activity (e.g., caspase enzymatic activity) can be used in transparent teleost embryo and can aid in distinguishing between apoptotic and necrotic activity.

Because teleost embryos, such as zebrafish, can be maintained in small fluid volumes (e.g., 100 µl) for the first four to five days of development, single embryos can be kept in individual wells of a multi-well (e.g., 96-well) culture plate. Alternatively, multiple embryos (e.g., 10 embryos) can be kept in each well of a 24- or 48-well culture plate, or the like. This makes it possible to detect signals, including, e.g., fluorescent, colorimetric, radioactive and chemiluminescent signals using standard microtiter plate readers and to automate methods of AP staining and detecting a variety of compounds for their effects on cell death activity.

In addition to automating detection, sample handling can be automated for rapid reproducible application of dyes and compounds to the teleosts using methods described herein. To increase the throughput of a compound application, currently available robotic systems (such as the BioRobot 9600 from Qiagen, the Zymate from Zymark or the Biomek from Beckman Instruments)—most of which use the multi-well culture plate format—can be used with methods of the invention. Well-known and commercially available instrumentation system can be employed to automate in situ hybridization and data recording and retrieval systems and other aspects of the screening methods of the invention.

The present invention also provides methods of screening a compound for an effect on cell death activity in vivo which comprise administering the compound to a teleost in vivo and detecting a response in the teleost indicating an effect on cell death activity, wherein a library of compounds is screened for an effect on cell death activity, including apoptotic and necrotic activity. In some such methods, the library of compounds comprises natural compounds. In other such methods of the invention, the library of compounds comprises synthetic compounds. In yet other methods of the invention, the library is a combinatorial library. Methods of the invention are useful to screen compound and chemical libraries for molecules which repress or trigger cell death, including repressing or triggering apoptosis or necrosis.

IV. Methods of Screening an Agent for Toxic Activity

A. Whole Animal Toxicity Testing

The predominant methods for toxicity testing use cell-based assays to evaluate the potential impact of different compounds on human and animal health. The cytotoxic effect of chemicals on mammalian cells is primarily measured by cell viability and unscheduled DNA synthesis. Because these toxicity screens are designed to evaluate the in vitro effect of a compound against cellular targets, they are limited in their ability to predict effects at the organism level, including lethality. In contrast, use of whole animals for toxicity testing addresses the limitations of cell-based assays and permits simultaneous evaluation at the molecular and cellular levels.

Whole embryo testing has previously been performed on invertebrates, including fruitfly and nematode (Eisses, *Teratog. Carcinog. Mutagen* 9:315-325 (1989); Hitchcock et al., *Arch. Environ. Contam. Toxicol.* 33:252-260 (1997)). However, because invertebrates are not closely related to humans and lack many of the same organs and enzymes, the use of such results as predictors of toxic effects in humans are limited. Embryo toxicity testing in mammals falls into two categories: 1) culture assays using either rat or mouse embryos, and 2) in utero assays in which compounds are injected into the peritoneum of a pregnant mouse or rat. Although the whole-embryo mouse and rat culture technique is a validated method for toxicity testing in vertebrates (Chatot et al., *Science* 207:1471-1473 (1980); Circurel and Schmid, *Xenobiotica* 18:617-624 (1988)), toxicity testing using this method is complicated and only a limited number of expensive assays can be performed. Embryos must be carefully explanted with the visceral yolk sac and ectoplacental cone intact at 8.5 days of development. Embryo culture time is also limited to 48 hours (Bechter et al., *Teratol.* 44:29A (1991)). In addition, due to the complexity of culture conditions, the incidence of both false positives and false negatives is high (Guest et al., *Can. J. Physiol. Pharmacol.* 72 (1):57-62 (1994)). The in utero approach avoids these issues; however, this approach is complicated by the fact that the compounds being tested can be metabolized in the liver of the mother. Further, although the in utero approach is useful for examining prenatal effects, it is not helpful in evaluating toxic effects of a compound on postnatal development. The frog embryo system is another commonly used model for in vitro toxicity testing; however, because frog embryos are not transparent it is very difficult to examine toxic activities against particular tissues and organs over time or simultaneously. A method which permits the screening an agent for toxic activity in multiple different organs and tissues of an animal simultaneously and/or in the whole animal in vivo is needed.

B. Toxic Activity Screening Methods

The present invention provides methods of screening an agent for a toxic activity in an intact, whole animal and in tissues and organs of whole animals in vivo or cells in in vitro using cells of the animal. Such activity can be assessed relative to contemporaneous and/or historical control teleosts (or teleost tissues, organs, or cells) to which the agent has not been administered. Such methods comprise administering the agent to a teleost and detecting a response in the teleost indicating the activity. Such methods are useful for rapidly, comprehensively, and reproducibly screening for and predicting toxic responses, including harmful and lethal effects on developing organs and tissues in whole teleosts, due to particular agents.

The zebrafish is among the preferred teleosts for these methods. As outlined in detail above, zebrafish offer a number of advantages for toxicity testing, including that zebrafish are transparent (thus facilitating observation and analysis of multiple tissues and organs simultaneously), develop rapidly, are easy and inexpensive to generate and maintain, and amenable to high throughput toxicity screens. In addition, the morphological and molecular bases of tissue and organ development are generally either identical or similar to other vertebrates, including man, and thus toxicity screens of compounds in zebrafish provide relevant information about the effect of compounds in humans. Moreover, we have determined that teleosts exhibit dose-responsiveness to toxicity and thus zebrafish and the toxicity screening methods described herein are useful in determining the effects of particular doses of agents on particular organ and tissue systems and the sensitivity of particular organs and tissues to such doses.

As described above, the compound to be screened can be administered to the teleost by diffusion simply adding it to the media containing the teleost or by microinjection or similar techniques which would be known to one of ordinary skill in the art.

The present invention includes in vivo methods for screening agents for a toxic effect or activity on one or more organs (e.g., the kidney, pancreas, cardiovascular system, central nervous system, liver, etc.) or tissues simultaneously or independently. Also included are in vitro methods in which an agent is administered to a culture of cells of the animal and the response indicating activity is detected in the cells. All such methods can be used to screen a wide range of agents and compounds, including, among other things, chemical compounds, pharmaceuticals, therapeutics, environmental and agricultural agents, industrial agents, pollutants, cosmeceuticals, synthetic or natural compounds, drugs, organic compounds, lipids, glucocorticoids, peptides, antibiotics, chimeric molecules. sugars, carbohydrates, etc. These agents and compounds can be screened singly or as mixtures, including complex mixtures.

The methods of the present invention allow for investigation of molecular methods for assessing key liver and kidney enzymes as biomarkers for organ toxicity. Subtractive library techniques and multiple enzymatic assays, in combination with drugs of known toxicity, can be used to identify new genes involved in drug response and metabolic activation phenomena and thus contribute to establishing and validating new biomarkers.

Toxic effects and activity resulting from administration of a compound to an animal (e.g., teleost) can be indicated by a variety of responses in the animal, including, but not limited to, e.g., molecular changes, genetic mutations, developmental defects, developmental delay, genotoxicity, reproductive toxicity, organ toxicity or dysgenesis, behavioral toxicity, teratogenicity, death of the animal etc.) Responses indicating toxic activity can be detected in the whole teleost or in at least one tissue or organ of the teleost. The response can be detected in multiple tissues and organs simultaneously or separately over time at predetermined time intervals. For example, the response can be detected in at least two different tissues, at least two different organs, or in at least one organ and at least one tissue. In in vitro methods, the response is detected in one or more cells of the teleost.

Additionally, a response indicating toxic activity can be detected as a change in a gene expression (mRNA) profile for one or more cells, tissues, organs of the animal, or the whole entire animal, by extracting and measuring the level(s) of one or more mRNAs expressed in such cell(s), tissue(s), organ(s) or the entire teleost at a certain time following agent administration and/or under a specific set of conditions. To do this, subtractive library experiments can be performed. mRNA from the control (untreated) and experimental (treated) embryos are extracted at an early and late response period. The subtractive libraries are constructed with the polymerase chain reaction (PCR)-Select cDNA Subtraction System (CLONTECH Laboratories, Inc.). Those genes from the embryo that are differentially expressed as a consequence of the exposure to the compound are selectively isolated, cloned and characterized using standard procedures. The cDNAs are used to construct a cDNA microarray.

A response indicating toxic activity can also be detected as a change in a protein expression profile for one or more cells, tissues, organs of the animal, or the whole entire animal, by extracting and measuring the level(s) of one or more different proteins expressed in such cell(s), tissue(s), organ(s), or the entire animal at a certain time following compound administration and/or under a particular set of conditions. In this protein-based approach, differences in post-translational modification or processing such as cleavage can be examined using two-dimensional polyacrylamide gel electrophoresis. Extracts from control embryos and those exposed to compounds can be directly compared in the same gel by tagging each extract with a different fluorophore prior to electrophoretic separation. The tags have no effect on the relative migration of labeled proteins during electrophoresis. Proteins that appear unmodified in both samples appear as spots composed of both fluorescent dyes. Proteins that differ between the two samples, as a result of cleavage, phosphorylation, etc., fluoresce as tagged in the original extracted sample.

One of ordinary skill in the art would recognize that a variety of techniques can be used together or separately to generate a signal (e.g., in situ hybridization, antibody staining of specific proteins, etc.) and to detect and assess responses (e.g., colorimetry, fluorescence microscopy, light microscopy, digital image analyzing, standard microplate reader techniques, fluorometry, including time-resolved fluorometry, and chemiluminescence, visual inspection, CCD cameras, video cameras, photographic film, or the use of current instrumentation such as laser scanning devices, fluorometers, photodiodes, quantum counters, plate readers, epifluorescence microscopes, scanning microscopes, confocal microscopes, flow cytometers, capillary electrophoresis detectors, or by means for amplifying the signal such as a photomultiplier tube.

C. Screening Agents for Toxic Activity and/or Angiogenesis Activity and/or Cell Death Activity Simultaneously The methods for screening agents for toxic activity described herein can be combined with other methods of the present invention, including methods of screening agents for angiogenesis activity (Section II) and cell death activity (Section III). As noted previously, with transparent teleosts, it is possible to assess such multiple activities and the responses resulting from such activities in the whole teleost or in one or more tissues or organs simultaneously and at predetermined time intervals. Assays combining toxicity screening with screening for cell death activity are useful as discussed previously for identifying deleterious and lethal responses resulting from agent administration, proper dosage amounts, and in developing effective therapeutics and treatment programs.

A variety of techniques can be used together or separately to analyze multiple activities and responses, including fluorescence microscopy, light microscopy, digital image analyzing, standard microplate reader techniques (colorimetry, fluorometry, including time-resolved fluorometry, and chemiluminescence), in situ hybridization, antibody staining of specific proteins, enzymatic changes, changes in protein distribution temporally and spatially in the teleost, etc.

In one aspect, the present invention provides a method of screening an agent for a toxic activity as described above which further comprises screening the agent for an effect on cell death activity by detecting a response in the teleost indicating an effect on cell death activity (as discussed above). Tissue and organ specific patterns of cell death can be evaluated in addition to examining various markers to analyze organ toxicity. Cells undergoing cell death can be identified by a variety of means, including those discussed above (e.g., using a membrane-impermeant, nuclear-staining dye from the benzothiazolium-4-quinolium dye family, the TUNEL assay, or calorimetric or fluorometric enzymatic assay of caspase activity).

In another aspect, the invention provides a method of screening an agent for a toxic activity as described above which further comprises screening the agent for an increase or decrease in angiogenesis by detecting a response in the teleost indicating an increase or decrease in angiogenesis activity.

Examples

1. Screening Compounds for Toxic Activity on Liver and Kidney in Zebrafish

A. Methods
1) Embryo Collection

Wildtype zebrafish embryos were generated by natural pair-wise mating, sorted for viability, and collected as described in Section II for screening methods for angiogenesis activity. Embryos before being sorted for viability. Because the fish embryo receives nourishment from an attached yolk sac, no additional maintenance was required.

2) Compound Screening

As discussed above, a variety of compounds can be screened using the methods described for toxic activity on whole animals (e.g., teleosts) and specific organs and tissues. The developmental toxicity effects of therapeutic/pharmacologic compounds can also be studied; results with such compounds using teleosts can be compared with the results obtained by NCI using mammalian models. By such comparison, the use of the methods and animal models of the invention for predictive assays for developmental toxicity effects of potential therapeutic compounds can be assessed.

3) Maintenance of Embryos and Administration of Compounds

Fertilized zebrafish embryos were obtained by natural spawning in our aquaculture facility. To reduce variations between batches, randomized samples of embryos from 3 or 4 independent matings were used. The test medium was prepared by combining 5 g of Instant Ocean Salt with 3 g of $CaSO_4$ in 25 liters of distilled water, according to Westerfield, supra. The embryos were maintained in the test medium throughout the experiments. Embryos at 24 hours of development (with chorion) were exposed continuously for five days to chemical compounds at different concentrations of the chemical compounds and controls. In general, the concentrations ranged from 100 nanomolar (nM) to 100 micromolar (µM). Tests were repeated four times for each series of dilutions, and a standard deviation was calculated for each treatment (see "Statistical Methods" section). Ten embryos per concentration were exposed in a total volume of 1 ml (constant ratio of 100 µl/embryo) using a 24 multi-well plate. (Other sizes of multi-well plates, such as 96-well plates can also be used to facilitate screening). The compounds were renewed daily. In all cases, 0.1% of dimethyl sulfoxide (DMSO) was used as a carrier solvent during the treatment. Controls with and without 0.1% DMSO were performed in all experiments. This approach has long been used to introduce anesthetics and other chemicals into fish embryos (Westerfield, supra).

Experiments were carried out at a constant temperature (28-28.5° C.) in the dark to protect the compounds from decomposition due to light exposure. Dead embryos were removed daily, counted, and used to calculate the Median Lethal Concentration (LC50, see "Statistical Methods" section herein). Each day, surviving embryos were analyzed visually under a dissecting binocular microscope (Zeiss, amplification 30-50x). Macroscopic malformations (such as axial defects, embryolethality, growth inhibition, general malformations, including microcephaly, macrocephaly, tail truncation, tail malformation, loss of axial structures, such as somites, etc.) were observed, classified, and counted to assess whole animal toxicity. Compounds that were lethal or induced these or any noted malformations or disruptions during development (e.g., during the first 5 days of development) were further examined for toxic effects on organs. The embryonic developmental stage that is affected by the toxic compound can be determined. Organ toxicity can be assessed in surviving embryos using in situ hybridization, enzymatic assays, and immunochemistry procedures.

For therapeutic drugs screened for toxic effects, the Median Effective Concentration (EC50) (the median concentration needed to caused a desirable effect on a target) can be determined. The Therapeutic Window (TW) (e.g., LC50/EC50) can also be determined; compounds exhibiting a high Therapeutic Window, such as 100 or 1,000, are good potential drug candidates because toxicity at the therapeutic concentration is low.

4) Tissue and Organ Toxicity Testing
a) In Situ Hybridization

To assay specific tissue and organ degeneration, whole mount in situ hybridization with RNA probes labeled with digoxigenin (Boehringer Mannheim) can be used. Probes which stain early embryonic tissues include MyoD, for the paraxial mesoderm during somitogenesis; brachyury, for the notochord. Probes which specifically stain organs include krx20 and pax2 for detection of abnormal development of the caudal midbrain and anterior hindbrain; c-ret for the presumptive brain, spinal cord and excretory system (developing kidney; nephric duet, and pronephros); and pes for optic tectum, liver primordium, and gut. In situ hybridization is carried out as follows: embryos are fixed with 4% paraformaldehyde in PBS and hybridized at 65° C. For visual inspection under a microscope, alkaline phosphate-conjugated anti-digoxigenin antibody is used to detect signals following staining with NBT/X-phosphatase (Boehringer Mannheim). Toxicity effects on tissue and organ development and function (e.g., liver and kidney), the expression and inducibility of a constitutive isozyme LMC2 and dioxin-inducible isozyme LM4B of cytochrome (Cyt.) P-450 in different organs and tissues by immunohistochemical localization can be analyzed by using methods described in Buchmann et al., *Toxicol. Appl. Pharmacol.* 123:160-169 (1993).

Automated in situ hybridization image analysis is readily performed using alkaline phosphatase-conjugated anti-digoxigenin antibody to detect signals after staining with NBT/X-phosphatase.

b) Assessing Toxic Activity in the Liver by Staining

Toxic activity in the liver of the treated whole animal can be assessed visually by using a rapid colorimetric staining procedure. This procedure is based on the use of a streptavidin (avidin) conjugated reporter enzyme, such as peroxidase, to detect naturally biotinylated carboxylase enzymes in the liver, gut, and digestive tube of whole animals, such as zebrafish embryos. These biotinyl-lysine containing enzymes, such as acetyl-CoA carboxylase and other carboxylases, are predominantly located in the liver and digestive tube. As a result, staining is organ specific (FIG. 11). Quantitative biotinylated assessment of the liver can be made. By visual detection of biotinylation, size and location of the liver can be determined.

Zebrafish embryos (4, 5 or 6 days old) were fixed with 4% paraformaldehyde for 1 hour at room temperature and treated with methanol 100% overnight at −20° C. The embryos were rehydrated and washed with PBST. After washing with PBST, the embryos were incubated in blocking solution (3% BSA, 100 mM NaCl in PBST) for 1 hour and treated with a bleaching solution (5% Formamide, 0.5×SSC, $H_2O_2$ 10%) for 20 minutes under natural light illumination. After bleaching, the embryos were incubated for a second time with the same blocking solution for 1 hour and incubated with streptavidin conjugated peroxidase (Pierce) (dilution 1:100 in the same blocking solution) with shaking at room temperature for 2 hours. The embryos were then washed twenty minutes three times with PBST and stained for peroxidase with two different dyes: Diaminobenzidine (DAB) (Pierce) (insoluble) to assess liver staining and 2,2'-Azino-bis(3-Ethylbenz-thiazoline-6-sulfonic acid) (ABTS) (Sigma) (soluble) to measure a quantitative visual signal using a colorimetric method. The DAB staining solution used comprised: 1 ml of DAB stock solution (5 mg of Diaminobenzidine/ml in PBS, pH 7.4), 9 ml of PBS, 10 µl of $H_2O_2$ (30%). Normally, specific liver staining was visualized in 1-5 minutes. Staining for the DAB solution was stopped by several washes with water. The ABTS colorimetric method used 10 ml of ABTS solution (10 mg in 33 ml of 0.1 M Citric Acid/OH, pH 4.35) plus 10 µl of hydrogen peroxide (30% stock) and was performed for 30 minutes at room temperature with at least 5 embryos per condition (1 ml of ABTS solution/5 embryos). The ABTS staining was stopped with 20% SDS/50% N'N-Dimethyl Formamide. The ABTS signal was detected by measuring the absorbance of the solution at 405 nanometer (nm) using a spectrophotometer. For each condition, four repetitions were performed and the standard deviation "S" calculated as indicated in "Statistical Methods" section below.

c) Assessing Toxic Activity in the Kidney by Staining

Toxic activity in the kidney (Pronephros) can be assessed visually by calorimetric staining of the kidney of the treated whole animal (e.g., zebrafish). Zebrafish pronephros express high levels of the enzyme alkaline phosphatase that can be easily assayed using a chromogenic dye. To stain kidneys in zebrafish embryos, embryos were fixed with 2% paraformaldehyde overnight at 4° C. and then treated with methanol 100% for 30 minutes at room temperature. The embryos were rehydrated and equilibrated in NTMT buffer (50 mM $MgCl_2$, 100 mM NaCl, 100 mM Tris/HCl, pH 9.5, 0.1% Tween 20) at room temperature and then stained with stain solution (75 mg/ml NBT and 50 mg/ml X-phosphate, equilibrated in the same buffer). Normally, specific kidney staining was visualized in 10-20 minutes (FIG. 14). This staining method was used to assess the toxic activity of aspirin and dexamethasone on kidney (see below).

d) Assessing Enzymatic Activity

The methodology for assessing enzymatic activity involves in the exposure of the teleost embryos to different compounds at different times (hour to days) with the subsequent in vitro analysis of their different enzyme activities. The embryos are incubated in a multi-well plate in the presence or not (i.e., controls) of different compounds. After exposure, they are used to obtained cell lysate preparations. The enzymes are assayed by the use of calorimetric or fluorometric dyes in end-point or kinetic experiments. The plates are read in an appropriate microplate reader. Multienzymatic microarrays can be constructed.

5) Assessing Organ Toxic Activity of Aspirin and Dexamethasone

In feasibility studies, aspirin and dexamethasone were screened for toxic activity on zebrafish embryos using the methods of the invention described herein. Aspirin, a general inhibitor of cyclooxygenases (Bosman, *Skin Pharmacol.* 7:324-334 (1994)), was previously shown to produce toxicity in a variety of organs in mammal embryos, including the kidney (Ungvary et al., *Teratology* 27 (2):261-69 (1983)). Dexamethasone, an immunosuppressor (Iida et al., *Carcinogenesis* 19:1191-1202 (1998)), was previously shown to produce liver and gastrointestinal toxicity and to be hepatotoxic in children undergoing cancer treatment (Wolff et al., *Anticancer Res.* 18 (4B):2895-99 (1998)).

Results are presented in Table 4. As with aspirin, for dexamethasone the LC50 obtained with zebrafish embryos was similar to the values previously described for mice and rats (Table 4). Liver and gastrointestinal toxicity and a dose-response effect were also observed (FIGS. 12A-12B). The quantitative colorimetric endpoint method discussed above was used to measure the effect of drug treatment on the liver (FIG. 13). Treatment with 100 µM dexamethasone reduced the colorimetric signal by about 70%, compared with the untreated embryos (control, 0% dexamethasone, FIG. 13). The change in color correlated well with the reduction in size previously observed in the liver using a chromogenic dye (FIG. 12B, bottom), suggesting the reproducibility and accuracy of the assay. The method was quantitative (with good confidence limits), rapid, and easy to perform.

The method can be automated using known instrumentation and techniques automated toxic screening.

TABLE 4

| | Five-Day Zebrafish Toxicity Testing Compared with Mammalian Models[1] | | | |
|---|---|---|---|---|
| | Zebrafish | | Mammalian models | |
| Compound tested | $LD_{50}$[2] (mg/liter) | Specific toxicity observed | $LD_{50}$ (mg/kg) | Specific toxicity (from the literature[3]) |
| 1. Aspirin (Clycooxigenase inhibitor) | 101 | teratogen, kidney, muscle contraction, erratic movements | 250 (mice, or.)[4] 200 (rats, or.) 167 (mice, i.p.)[5] | kidney, ureter, cardiovascular, craniofacial, musculoskeletal |

TABLE 4-continued

Five-Day Zebrafish Toxicity Testing Compared with Mammalian Models[1]

| | Zebrafish | | Mammalian models | |
|---|---|---|---|---|
| Compound tested | $LD_{50}$[2] (mg/liter) | Specific toxicity observed | $LD_{50}$ (mg/kg) | Specific toxicity (from the literature[3]) |
| 2. Dexamethasone (immunosuppressor) | 324 | liver, gastro-intestinal | 410 (mice, i.p.) 54 (rats, i.p.) | liver, gastro-intestinal |

[1]Including mice and rats.
[2]The $LD_{50}$ was calculated as indicated in "Statistical Methods."
[3]Data was obtained from TOXNET Web Search and other sources.
[4]or. = orally
[5]ip. = intraperitoneal 6) Statistical Methods
a) Estimation of LC50

For the concentrations tested with aspirin and dexamethasone in these studies, there was no partial lethality and the geometric mean of the parameters "no mortality" (0%) and "mortality" (100%) of the effect concentration was taken as the LC50 and binomial confidence limits were calculated according to Stephan, "Methods for Calculating LD50" in *Aquatic Toxicology and Hazard Evaluation* (F. L. Mayce and J. L. Hamelink eds.) ASTM STP 634, pp. 65-84. Amer. Soc. Testing Materials, Philadelphia, Pa. (1977).

b) Standard Deviation

The colorimetric liver stain method described above was used to obtain qualitative data (i.e., changes in the size, presence, or location of the organ) and to study the significance of the variations found in each treatment. For each condition, four repetitions were performed and the statistical value, with its standard deviation, was used to prepare graphics using Microsoft Excel 97 or similar known, standard software/graphics programs.

7) Teratogenic Effects

Information about additional toxic responses/effects indicating toxic activity of a compound, such as, e.g., growth inhibition and teratogenesis, including microcephality, macrocephality, tail truncation, tail malformation, can be evaluated by visual inspection using a dissecting microscope (Zeiss, amplification 30-50×). Multiple toxic responses and effects can be assessed rapidly and simultaneously in transparent teleost embryos.

8) Assessment of Additional Biomarkers

Commercially available antibodies can be used to detect expression and inducibility of different kidney and liver enzymes by immunohistochemistry. With these biomarkers, the toxicity of drugs and compounds, including those having known toxicity, can be investigated. The toxic effects of new drugs to be used in the subtractive library screen can also be readily assessed by the methods described herein. Examples of such antibodies include, e.g., anti-Proton Pump H+/K+ ATPase (kidney, Panvera Corporation); anti-LMC2 and anti-dioxin-inducible isozyme LM4B of cytochrome P-450 (kidney and liver), as previously described (Buchman et al., *Toxicol. Appl. Pharmacol.* 123:160-69 (1993)); anti-Glutathione S-Transferase (kidney, liver, Panvera Corporation).

2. Identifying Organ Specific Genes Involved in Compound Toxicity Responses Using Subtractive Library Techniques As a predictive method for drug toxicity, a multi-parametric toxicity test would be very valuable and useful. Subtractive library experiments are useful in developing such an approach. Such methodology allows the identification of genes that are differentially expressed in a target organ as a result of chemical/drug exposure. Currently, the genes/pathways involved in drug/chemical toxicity response and drug/chemical metabolic activation are difficult to assay primarily due to the lack of available probes and substrates. Additional information regarding organ drug toxicity can be obtained by isolating new genes in the animal (e.g., teleost) using the subtractive library method. The genes are cloned, the expression profiles of the genes are evaluated, and their significance as markers for toxicity is compared with data previously obtained in mammals.

A. Subtractive Library Techniques

Genes which are differentially expressed in a target organ as a result of drug/chemical exposure can be identified by using subtractive library techniques as follows. Using selected compounds from our LC50 and organ toxicity methods and analyses described above, zebrafish embryos are treated to induce organ toxicity. At different time points during drug treatment, the liver and/or kidney (treated and controls) are dissected. This material is used to prepare subtractive libraries to isolate new genes differentially expressed in treated and control embryos. Subtractive library techniques (e.g., Clontech, Palo Alto, Calif.) are used to selectively isolate genes. The Clontech PCR-Select system uses suppression PCR and requires only one round of subtractive hybridization to subtract and equalize cDNAs. In addition, the technique requires very low amounts of poly A+RNA prepared from two types of tissue under comparison; normally 0.5-2.0 μg. Recently, this technique was used to isolate several caffeine up-regulated genes from the pre-B cell line 1-8, including IGF-1B, and a predicted homologue of the natural killer cell antigen, NKR-P1 (Hubank and Schatz, *Nucleic Acids Res.* 22: 5640-5648 (1994)).

The genes identified by the subtractive library technique are selected, and the expression pattern of these genes in the embryos during compound/drug exposure can be evaluated. The expression pattern can be compared with the pattern found in mammalian homologues under similar conditions. Genes that serve as "good" indicators or marker of toxicity (e.g., organ toxicity) can be identified and selected.

B. Transgenic Teleosts

Adequate regulatory regions upstream from the target genes with predictive toxicity value response can be used to construct transgenic teleosts (e.g., zebrafish) carrying reporter genes. The 5' upstream region of these genes is analyzed in order to use the regulatory region to control the expression of reporter genes in transgenic zebrafish. In this approach, genes isolated using subtractive library techniques are used to analyze the 5' regulatory region. To construct plasmids carrying a reporter gene, such as the Green Fluorescence Protein (GFP) under the control of those regulatory regions, those upstream regulatory regions that are adequate in size (1 or 2 kilobases) and expression profile are employed. These plasmids are used to produce transgenic fish as described in Long et al., *Development* 124:4105-4111 (1997). For example, because zebrafish are transparent, cells in transgenic zebrafish that express GFP (a reporter gene in specific organs and tissues) can be detected in vivo using standard fluorescence-based detection techniques; specifically, when cells expressing GFP are illuminated with blue or ultraviolet (UV) light, a bright green fluorescence is observed. Light-stimulated GFP fluorescence technique does not require co-factors, substrates or additional gene products and therefore screenings can be performed in vivo, and using the same embryos, toxicity effects can be monitored over time using, e.g., a fluorescence plate reader. Using this screening method, many genes involved in a drug response which would otherwise be difficult to assay can be easily assessed.

C. Zebrafish cDNA Microarrays cDNA microarray technology can be used to profile complex combinations of gene expression in drug toxicity response and metabolic activation phenomena. Gene expression of specific organ toxicity can be monitored using a microarray of selected zebrafish genes isolated by the subtractive library techniques discussed above and other sources of genes. The cDNA arrays are simple and permit direct readout of hybridization results; thus, they constitute an ideal technique for studying gene expression patterns in tissues undergoing drug treatment at different timepoints (Heller et al., *Proc. Natl. Acad. Sci. USA* 94:2150-2155 (1997)).

V. Screening Automation

The multi-parametric methodology described above can be automated using standard instrumentation and computer software programs, permitting the screening of hundreds of agents per week. These methods combine the physiological advantages of the teleost and simplicity of agent addition with the ease of sample handling and detection provided by microtiter plates and associated dispensing and detection apparatus. The methods are premised, in part, on the observation that teleosts can be cultured and develop normally within the confined space of microtiter wells notwithstanding the accumulations of waste products and low availability of oxygen due to the confined space. Accordingly, large numbers of agents can be screened in parallel in the wells of a microtiter plate containing fertilized embryos. As for other screening methods discussed above, because teleost embryos develop normally in 100 µl of water, agents and dyes can easily be added to the medium. Furthermore, because transparent teleost embryos become opaque when they die, embryo lethality is comparatively straightforward to identify using a standard microtiter plate reader to calculate the LC50. In addition, a GFP transgenic fish can be monitored over time in a microplate reader.

An exemplary scheme for performing high throughput screening is shown in. FIG. 15. Zebrafish embryos are contacted with agents to be screened for sufficient time for the agent to elicit a response indicative of a pharmacological activity in the zebrafish. The amount of time depends on the assay and can range from 1 hour to 7 days. Different wells can be used to test different agents, and/or to test the same agent at different concentrations. In some methods, each well contains a single zebrafish and in some methods, each well contains multiple zebrafish. After treatment, wells are analyzed to determine continued viability of zebrafish (e.g., by determining absorbance at 550 nm). Death of zebrafish results in high absorbance. Wells containing agents resulting in high lethality are not further pursued, but the identity of such agents can be stored in a computer file.

Wells containing viable zebrafish are then assayed for pharmacological activity of the agents being tested. This activity is often a change in concentration of a cellular marker or in the number of cells expressing a cellular marker. This activity can be detected using a substrate processed by the enzyme to generate an optically detectable product. After performing the assay, the plates are read for an optical signal indicating pharmacological activity. Agents showing good activity in the assay are then subjected to a confirmatory assay. This assay can be performed in a microtiter format as before, or can be performed by a different format on a teleost (e.g., a microscopic assay), or can be performed on a higher organism. In some methods, the confirmatory assay detects the same response as the primary assay but by a different means. For example, the primary assay can detect an increase in enzyme activity colorimetrically using a microplate reader, and the confirmatory assay can detect the same enzyme activity on a micrograph. Agents showing good activity are also tested for toxicity and lethality. These assays can be performed in a microtiter format or using other methods described above. Suitable enzymes whose activities are indicative of a toxicity response in the heart or liver, and substrate for detecting them are described in the Examples that follow.

The equipment used in the above assays typically includes a multiwell plate, apparatus for dispensing embryos, apparatus for dispensing small volumes to the wells, apparatus for mixing fluids in the wells, apparatus for washing the wells, a coding to label wells and the plate, a plate reader for detecting an optical signal from the wells and for reading the code and a computer for controlling the other apparatus and for storing data. For dispensing teleosts, an automated particle handling device equipped with a light scattering detection system which can contribute about 1 mm particles and distinguish dead embryos (white) from live embryos (transparent) is suitable (BD Biosciences, Bedford, Mass.). To add and remove liquid (e.g., media, washing solutions, labeling reagent solutions), an automatic microplate pippetting and washing workstation (Biomek, Beckman-Coulter, Zymark, Hopkinton, Mass.; Packard Bioscience, Groningen, The Netherlands) is suitable. The type of plate reader depends on the nature of the measurement to be made (i.e., fluorescence, chemiluminescence, colorimetric or radioactive via scintillation counting). Some commercially available plate readers can detect multiple types of signal. Multi-well plates typically have 96 wells, but larger or smaller number of wells can be used. In a standard plate, each well has a volume of about 300 µl but larger or smaller volume wells can be used. Typically, zebrafish are cultured in a volume less than 1 ml, sometimes less than 500 µl, sometimes 50-200 µl, and preferably about 100 µl. Several laboratory and robotic systems have been developed for the purpose of processing microtiter plates. These devices are designed to increase laboratory throughput and many of these devices also provide positive sample identification through the use of analytical software and barcode labels. The correlation between identity of agents and wells can be referred to as a correspondence regime. Examples of suitable equipment are described below.

The assays are typically performed on whole teleosts. The teleosts can be natural or transgenic. The teleosts are living when contacted with agents. In some methods, teleosts are killed before detecting signal. In such methods, the agent being tested is typically removed. Teleosts can then be fixed or lysed to facilitate detection of signal. In some methods, the teleosts remain living throughout the assay including detection of optical activity (such as GFP). In such methods, a series of measurements of signal can be made over time on the same teleosts. In such methods, the agent being tested and the labeling reagent used to test response can be left in contact with the teleost throughout the assay. In some methods, in which an optical signal is generated within a teleost, the teleost should be sufficiently transparent that the optical signal can be detected in the whole teleosts. In other methods, the signal diffuses out of the teleost, or can be induced to do so by treatment with lysing agents. In such methods, transparency of the teleost is not necessary.

The extent or rate of appearance of a signal depends on the response of a teleost to an agent, and the response is in turn an indicator of a pharmacological activity of the agent. For example, modulation of angiogenesis is a pharmacological activity, an increase or decrease in alkaline phosphatase activity is a cellular response indicative of angiogenesis, and an OD405 reading due to processing of the alkaline phosphatase substrate pNPP is an optical signal that depends on the cellular response. Similarly, modulation of apoptosis is a pharmacological activity, an increase or decrease in caspases activity is a response indicative of modulation of apoptosis and various substrates of caspases are suitable labeling reagents for generating an optical signal dependent on the response.

In general, a pharmacological activity is a property of an agent that indicates that the agent is, or may be, useful for treatment and/or prevention of a disease. Thus, pharmacological activity includes prophylactic and therapeutic activities as defined herein. In general, responses indicative of pharmacological activity can include: 1) a increase or decrease in the number of cells or the concentration a cellular marker, such as an enzyme or secondary metabolite in a cell, 2) the modulation of a cellular pathway, for example, by binding of an agent to a cellular receptor, or 3) the promotion or inhibition of a physiological event such as cell growth or differentiation. Examples of cellular markers that can be detected include nucleic acids and proteins and enzymes. Nucleic acids can be detected by a hybridization assay using a probe nucleic acid. Usually, the probe nucleic acid is labelled although secondary labelling schemes are also possible. Proteins can be detected using antibodies that specifically bind to the proteins. In some methods, the antibody is directly labelled and in other methods a secondary labelling scheme is used. Enzymes can be detected using a substrate processed by the enzyme to generate an optically detectable product. Modulation of cellular proliferation can be determined from corresponding modulation of component molecules, particularly constitutive expressed proteins, or nucleic acids.

Optical signals useful for monitoring cellular response include color, fluorescence, chemiluminescence, opacity, and radioactivity, the latter can be detected via scintillant induced light scattering. Responses can be detected by light scattering or photon counting or other methods. In some methods, a product having an optical signal is generated by a reaction within cells of the teleosts, and is an indication of the level of a particular enzyme catalyzing the reaction. In other methods, the labelling reagent is attached directly to an agent, such as antibody, that binds to a cellular molecule. In some methods, the labelling reagent is attached to a secondary-labelling reagent that binds to a primary reagent, which in turn binds to a cellular molecule.

Usually some wells of the multiwell plate are occupied by positive and negative controls. Positive controls can be agents (s) known to have the pharmacological activity being tested for and negative controls, agent(s) known to lack the pharmacological activity. In some methods, multiple positive and/or negative controls are distributed at different locations on the plate.

Microplate assays can also be used to monitor absorbance, excretion, metabolism or intracellular distribution of a agent in teleosts. In such methods, the wells provide a means to contain teleosts while a agent redistributes between media and the teleosts, and/or is metabolized within the teleost. Initially, the agent can be in the medium only, in the teleost only, or in both the teleost and the medium. After culturing the teleost for a period, the amount of the agent in the medium, or the teleost or both is determined. A decrease in the amount of agent in the medium over the incubation period is a measure of absorption of the agent and allows calculation of an absorption rate. An increase in the amount of agent in the medium over the incubation period is a measure of excretion of the agent and allows calculation of an excretion rate. An increase in amount of agent in the teleosts over the incubation period reflects a net absorption. A decrease in amount of agent in the teleost over the incubation period reflects a net excretion. By performing the assay with different initial concentrations of agent in the media and the teleosts, it is possible to calculate the rates of both of these processes. In methods in which the detection assay distinguishes between the agent and metabolic products of the agent, it is also possible to calculate a metabolism rate.

In some methods, the agent itself generates an optically detectable signal or can be labelled with a secondary labelling reagent that gives rise to such a signal. The combined amount of agent in medium and teleost is detected with microplate reader. After detection, the medium is discarded and the amount of agent within the teleosts is detected.

In some methods, when the agent is not labeled, the amount of agent in media can be determined by extracting the medium with chloroform (most small molecule agents are soluble in chloroform) or other organic solvent to isolate the agent, and quantifying the agent by HPLC/MS designed for automation. The agent within teleosts can be extracted with an organic solvent such as chloroform. The extracted agent and its metabolite can be analyzed by HPLC/MS designed for an automation system. In some methods, the teleost is fixed after culturing with the agent, and the location of agent within the teleost is determined by microscopic examination.

Examples

A. Procedure for High Throughput Screening

1. Synchronized embryos are distributed into 96-well assay plate. Embryos developmental stage (age) can be synchronized by treating the adult fish with propidium iodide, and stimulating them to lay egg in a predicted time frame. Embryos can be distributed using an automated particle handling devices equipped with a light scattering detection system (BD Biosciences, Bedford, Mass.). The particle handling device should preferably be capable of dispensing up to 600 µm particles. Alternatively a liquid dispenser fitted with large bore pipette tip can be used to dispense embryos into microtiter wells automatically.

2. 100 µl of diluted compounds are added to each well (in fish water). An automatic microplate pippetting and washing workstation (Zymark, Hopkinton, Mass.; Packard Bioscience, Groningen, The Netherlands) can be used. A simple bar code system to identify each plate (Decitek, Westborough, Mass.).

3. Plates are incubated at 28° C. for designated time period in an incubator.

4. Plates are assessed for dead embryos. Such assessment can be performed by visual inspection or by quantitative determination of absorbance at 550 nm. Dead embryos become opaque and disintegrate, and cause the clear culture solution to become turbid. This turbid solution usually absorbs light at 550 nm. Absorbances at 550 nm exceeding a threshold are scored as dead embryos, and this information is recorded in a lethal compound data base using the bar code system to read the identity of compounds causing lethality. Wells containing lethal compounds are eliminated from subsequent analysis steps.

5. The plate is washed to remove residual compound and fish water. In this and other wash steps, a vacuum manifold with adjustable vacuum pressure to remove the washing solution, and prevent the embryo tissue loss.

6. 100 µl ice cold 70% EtOH is added to each well.

7. The 70% EtOH is removed.

8. 100 µl of 100% EtOH is added.

9. The wells are incubated at −20° C. for 30 minutes in a −20° C. freezer

10. The 100% EtOH is removed.

11. 100 µl of appropriate buffer is added. The mixture is incubated for 10 min at room temperature. The procedure is then repeated 2 more times.

12. The above buffer is removed.

13. 100 µl substrate solution for an enzyme assay is added. The mixture is incubated at room temperature for designated time period 14. 100 µl of stopping solution is added.

15. A colored metabolic product resulting from an enzymic activity being measured is read at the appropriate wavelength in an automatic microplate reader (Biotek, Inc. Winooski, Vt.)

B. Assays for Pharmacological Activity

1. Detecting Angiogenesis

Angiogenesis was monitored by quantitative analysis of endogenous alkaline phosphatase (EAP) levels using the following procedure.

a. Embryos were dehydrated through 70% EtOH, then 100% EtOH b. Embryos were incubated in 100% EtOH c. Embryos were re-hydrated and equilibrated by 1M diethanolamine buffer pH 9.8 d. 100 µl of 0.5 mg/ml p-nitrophenyl phosphate (pNPP kit #37620, Pierce) was added as substrate e. incubation time was determined by testing (see following results)

f. 50 µL of 2N NaOH was added to stop the enzyme reaction g. OD at 405 nm was recorded by a ELISA plate reader We used normal zebrafish embryos at 24, 48 and 72 hours post fertilization with known patterns of vessel development as controls to established the optimal conditions for distinguishing different stages of vessel development quantitatively. Since the enzyme substrate (pNPP) comes in a fixed concentration, we defined the optimal incubation time for assessing different quantities of the enzyme. FIG. 16A shows a typical enzymatic kinetic curve between the OD reading and the substrate incubation time. A linear relationship can be established between the 20 and 40 minute time points. Based on this same data, the OD reading vs. embryo age for each incubation time were replotted to determine the optimal incubation time (FIG. 16B). 30 minutes is the optimal incubation time for distinguishing the difference in EAP level for embryos at 24, 48 and 72 hpf.

To demonstrate a correlation between results using the quantitative enzyme assay and microscopic observation of vessel development, a separate set of experiments was performed. Embryos, processed as described above, were measured directly for OD (405 nm) after incubating with pNPP for 30 minutes without adding the stopping reagent (2N NaOH). The OD results were similar to those with stopping agent added. The soluble substrate pNPP was washed off afterwards and the embryos were re-equilibrated into NTMT buffer and re-stained, as described in vessel staining for microscopic examination. The image is shown in FIG. 17. This result shows that the enzyme assay detects differences in vessel development, similar to results using microscopy.

The enzyme assay was then used to assess the effect of different concentrations of SU5416 on the embryos. Embryos with intact chorion at 24 hpf were collected and distributed into a 96-well plate. SU5416 at 0, 0.25, 0.5, 0.75, 1.0 and 1.5 µM (0.1% DMSO as carrier) was added directly into fish water and embryos were incubated continuously for 2 days at 28° C. At the end of the incubation, SU5416 was washed off using fish water, and embryos were dehydrated into EtOH and processed, as previously described. 24 hpf (day 1), embryos without chorion were used as the baseline (0%), and 72 hpf (day 3) normal embryos were used as 100% control.

The plot shown in FIG. 18 demonstrates a clear dose response curve; 50% of vessel development is inhibited with a 1.6 µM concentration of SU5416. It also indicates that the agent carrier (0.1% DMSO) does not cause a significant effect on vessel development. The OD measurement of the vessel development in these SU5416 treated embryos was also correlated by microscopy. Although there was a direct correlation, as expected, the quantitative enzyme assay was more sensitive.

2. Detecting Liver/Gut Toxicity

Several carboxylase enzymes containing biotin covalently bound as the coenzyme are present in the liver and gut of zebrafish embryos (Gregolin, et al, 1968).] The specific expression of these enzymes in the liver and gut in both control and agent treated embryos was observed by binding to avidin detected by microscopy. These parameters were then used to develop an ELISA-type assay to measure the level of carboxylase, which reflects liver and gut formation/function. The process involves the following steps.

(1) embryos are dehydrated through 70% EtOH, then 100% EtOH (2) embryos are incubated in 100% EtOH (3) endogenous peroxidase activity is suppressed by adding 25 µl of peroxidase suppressor (Prod. #35000, Pierce) for 30 minutes (4) Embryos are washed with PBS, pH 7.4 three times, 10 minutes each (5) Embryos are incubated with 100 µl of Avidin-Biotin-horseradish peroxidase (A-B-HRP) (Kit #32050, Pierce) for 1 hour (6) Excess A-B-HRP is washed off with PBS (7) Equilibrate embryos into 1M citrate buffer pH 5.0

(8) The embryos are incubated with 100% HRP substrate 3,3',5,5'-tetramethylbenzidine (TMB, kit #34021, Pierce) at various time interval to determine the optimal incubation time (9) 100 µl of 1M $H_2SO_4$ is added to stop the reaction

(10) OD at 450 nm is recorded to determine the carboxylase level

The linear relationship between the OD (450 nm) reading and incubation time is established, and the optimal substrate incubation time determined (at the mid-point in the linear range). OD (450 nm) is plotted against embryo stage. The slope between two points defines the difference in OD reading (ΔOD) between embryos at different stages. The sharpest slope gives the greatest difference in OD measurement, which is most useful in distinguishing the difference in carboxylase level, and reflects the difference in organ development. This parameter is used to determine the optimal embryonic stage for agent testing.

Correlation of quantitative measurement and qualitative observation of liver/gut is also performed based on the principle described above. Embryos 24 hours post fertilization (hpf) to 144 hpf are assayed at the determined optimal substrate incubation time as above, except, instead of adding 1M H2SO4 to stop the enzymatic reaction, the supernatant is removed from each well and transferred to a new plate to be measured for OD at either 370 nm or 652 nm. The embryos are washed in PBST (PBS plus 0.1% Tween 20) to remove residual TMB substrate and re-equilibrated for DBA staining. The DBA staining solution is prepared following the manufacturer's recommended protocol (1 ml of 0.5% DBA stock solution, 9 ml of PBS, 10 μl of 30% H2O2). Specific liver & gut staining is visualized in 1-5 minutes. Staining is stopped by several washes with water. Embryos are visualized on a dissecting microscope (Zeiss Stemi 2000-C). The size of the visualized image of liver/gut is compared to OD measurements.

Additional enzymes and their substrates that can be used to assess liver function in this format include:

TABLE 5

| Enzyme | Substrate | Source |
|---|---|---|
| Cytochrome P450 1A1 | methoxyresorufin | Sigma |
| Superoxide Dismutase | 5,6,6a,11b-tetrahydro-3,9,10 trihydoxybenzo[c]fluorene | Calbiochem Kit |
| Glutathione-S-transferase P1-1 | 5-((4'-(S-Glutathionyl))-2',3' 5',6'-tetrafluorobenzoylamino) fluoresein | Molecular Probes, |
| Glutathione peroxidase | Glutathione Proxidase Assay kit | Calbiochem Kit |

3. Detecting Heart Toxicity

Heart toxicity can be determined using specific heart proteins, tropomyosin and cardiac myosin heavy chain, as markers. Antibodies against these proteins are used as ligands for these markers. The antibodies are conjugated with horse radish perodixase (HRP), which is quantified by incubating with the substrate TMB. The steps are similar to those described in liver/gut toxicity assay, embryos are blocked by 0.2% bovine serum albumin (BSA) in PBS, then incubated with primary antibody against the specific protein for 2 hours at room temperature, washed in PBST to remove unbound primary antibody, secondary antibody conjugated with HRP is added instead of A-B-HRP.

4. Detecting Apoptosis

In response to a variety of apoptotic signaling cascades, caspases, which are normally present in the cell as pro-enzymes (zymogens), are either cleaved or auto-catalytically activated by intracellular sequestration. Caspase activity plays a pivotal role in the initiation and execution phases of apoptosis. The presence of caspase activity can be monitored in the embryonic zebrafish using commercially available fluorogenic and colorimeteric caspase substrates specifically engineered to penetrate the cell.

All reagents (fluorescent stains, chemical agents, and 'pre-treatment' apoptosis inducers for anti-apoptotic screen) are added directly to the fish water in 96 well plates. DMSO (0.2% unless otherwise indicated) was used as a vehicle or carrier. Controls 1) with tested agent alone, 2) without tested agent, but equivalent amount of carrier plus dye, and 3) no treatment, are usually carried out in parallel.

After brief period of recuperation, the embryos are analyzed with a microplate reader.

TABLE 6

| Enzyme | Substrate | Source |
|---|---|---|
| Caspase 1 | AC-YVAD-AMC | Calbiochem |
| | AC-YVAD-pNA | Calbiochem |
| Caspase 3 | AC-DEVD-AMC | Calbiochem |
| | AC-DEVD-pNA | Calbiochem |
| Caspase 2 | Z-VDVAD-AFC | Calbiochem |
| Caspase 4 | AC-LEVD-AFC | Calbiochem |
| Caspase 5 | AC-WHED-AFC | Calbiochem |
| Caspase 6 | AC-VEID-AMC | Calbiochem |
| | AC-VEID-pNA | Calbiochem |
| Caspase 8 | Z-IETD-AFC | Calbiochem |
| | AC-IETD-pNA | Calbiochem |
| Caspase 9 | Ac-LEHD-AFC | Calbiochem |

5. Detecting Change in Cellular Receptor Expression

The processes described above can be modified by adding a embryo lysing step after the agent incubation to improve the accessibility of receptors to ligands. Ligands for the specific cellular receptors can be either labeled by fluorescent dye or conjugated with horse radish peroxidase and assessed by the enzymatic reaction.

VI. Methods of Screening an Agent for an Activity in the Brain or Central Nervous System A. Central Nervous System The central nervous system (CNS), which includes the brain and spinal cord, represents the largest part of the nervous system. Together with the peripheral nervous system, the CNS has a fundamental role in the control and coordination of behavior and all essential functions of an animal. The CNS is contained within the dorsal cavity, with the brain within the cranial subcavity, and the spinal cord in the spinal cavity. The spinal cord carries signals from the body to the brain, where they are analyzed and interpreted. Response signals are then passed from the brain through the spinal cord and to the rest of the body.

Neurons, the cells that carry signals throughout the nervous system, are the basic functional unit of the nervous system. All neurons have the same physical parts: the cell body, dendrites and one axon. Neurons carry electrical signals known as impulses in only one direction. There are three types of neurons. (1) Sensory neurons carry impulses from the sense organs (receptors) to the brain and spinal cord. Receptors detect external or internal changes and send the information to the central nervous system in the form of impulses by way of the sensory neurons. (2) Motor neurons carry impulses from the brain and spinal cord to specific organs (e.g., muscles or glands). Muscles and glands are two types of effectors. (3) Interneurons connect sensory and motor neurons and carry impulses between them. These neurons are found entirely within the CNS.

In vertebrate embryos, neural development involves several steps and starts with the induction and patterning of the neural plate during gastrulation. The CNS originates from the neural plate, a specialised region of the ectoderm. The neural plate folds and forms the neural tube. The whole neural tube will differentiate into its two major subdivisions: spinal cord and brain.

Due to its relative simplicity as well as similarity to other vertebrates, the CNS in the zebrafish provides a powerful tool in assessing CNS diseases and toxicity. During zebrafish embryogenesis the brain rudiment is already visible at the end of gastrulation (9 hpf) as a distinctly thickened structure. Within the next 20 hours the primary organization and morphology of the zebrafish brain is established (Kimmel et al., *Devl. Dyn.* 203:253-310 (1995)). Neurulation of the zebrafish differs slightly from that of other vertebrates. In mammals, neurulation proceeds by invagination of the neural plate whereas in zebrafish, neurulation proceeds by the formation of a dense nerve rod, which then forms a lumen by caviation (Schmitz et al. *Dev. Biol.* 202:250-259 (1993)). Following the neural tube formation, however, the anterior end of the embryonic neural tube in every vertebrate, from fish to human, subdivide into three primary brain vesicles, forebrain, midbrain and hindbrain.

As in other vertebrates, the zebrafish forebrain consists of the telencephalon, optic vesicles, hypothalamus, ventral and dorsal thalamus and pretectum. The telencephalon in mammals includes cerebral cortex, olfactory bulb and basal ganglia. The midbrain (mesencephalon) consists of the tectum and torus tegmentum, which contain major relay centers for sensory information, and the tegmentum, which contains motor nuclei, especially those involved in eye movement. The midbrain also contains the substantia nigra, a group of dopamine-producing neurons that control movement and is the region affected in Parkinson's disease. The most rostral part of hindbrain, the isthmus rhombencephali (rhombencephalon), contains the cerebellar primordium dorsally.

During somitogenesis, sections of the neural tube giving rise to midbrain and isthmus fold up as two clearly separable domains, forming the midbrain-hindbrain boundary. This boundary region becomes an organizer involved in subsequent patterning of the brain. Hindbrain segmentation occurs at 18 somites (Schier et al., *Development* 123:165-178, (1996)). By 24-28 hpf, the zebrafish brain has the typical morphology of embryonic vertebrate brains (Kimmel et al., *Annu. Rev. Neurosci.* 16:707-732 (1993)).

Neurons of the zebrafish spinal cord develop in two waves; the first, or primary wave, occurs shortly after gastrulation and consists of relatively few, large neurons (Eisen, *Development* S2:141-147, (1991)). Primary neurons include all functional classes and are responsible for initial axon path finding. The subsequent wave of secondary neurons produces fewer, finer neurons and interneurons and motor neurons exclusively. There are 3 types of glial cells in zebrafish, including oligodendrocytes that myelinate neurons in larval and adult spinal cord. As in other vertebrates, motorneurons, oligodentrocytes and probably also secondary neurons, arise from same set of cells in the ventral spinal cord on both sides of the floor plate (reviewed in Lewis and Eisen, *Prog. Neurobiol.* 69 (6):419-449, (2003)).

The spinal cord and trunk of all vertebrate embryos are organized into segments called somites; this segmental organization results in a predictable repeating pattern of neurons. By 18-20 hpf each segment contains 18 neurons in 3 classes: mechanosensory neurons, interneurons and primary motor neurons (Kuwada et al., *J. Comp. Neurol.* 302 (2):617-628 (1990)). Because of the simplicity of this segmental organization, it is possible to identify individual neurons and follow specific axons during pathfinding.

Spatial and temporal expression patterns of regulatory genes such as those involved in the hedgehog and nodal signaling pathways, followed by the Fgf, wnt and hox family members are highly conserved between zebrafish and mammals Wilson et al., (2002)). In many cases, function has also been shown to be conserved, suggesting common mechanisms control vertebrate CNS patterning. Several genes specifying functional regionalization in the mammalian brain are conserved in zebrafish; for example, Zash-1a (Wullimann and Mueller, *Brain Res. Gene Expr. Patterns* 1:187-192 (2002)) and hlx1 (Hjorth et al., *Int. J. Dev. Biol.* 46 (4):583-96 (2002)). In addition, genes involved in neurotransmitter metabolism have recently been described, including tyrosine hydroxylase and the dopamine transporter (Holzschuh et al., *Mech. Dev.* 101:237-243 (2001)), as well as a regulator of noradrenergic neuronal gene expression, Tfap2a (Holzschuh et al., *Development* 130 (23):5741-5754 (2003)).

B. Blood Brain Barrier

The blood brain barrier (BBB) is the network of capillaries that controls the passage of substances from the blood into the brain and other parts of the central nervous system (CNS). In mammals, the BBB is made of specialized endothelial cells, pericytes embedded in the basal membrane, perivascular macrophages and astrocyte endfeet (Gloor et al., *Brain Res. Rev.* 258-264 (2001); Ballabh et al., *Neurobiol. Dis.* 16:1-13 (2004)). While allowing essential substances including nutrients to transit into the CNS, the BBB functions as a primary physical barrier to harmful substances. In its neuroprotective role, the BBB also provides protection for the CNS against common infections by keeping out pathogens.

Unlike peripheral capillaries that permit some level of free exchange of molecules through the pores, the BBB strictly limits transport into the brain by physical barriers (Cordon-Cardo et al., *Proc. Natl. Acad. Sci. USA* 86:695-698 (1989); Ghersi-Egea et al., *J. Neurochem.* 62:1089-1096 (1994); Drion et al., *J. Neurochem.* 67:1688-1693 (1996); Engelhardt, *Cell Tissue Res.* 314:119-129 (2003)). The main physical characteristic which differentiates endothelial cells in the BBB from those in peripheral capillaries is that BBB endothelial cells are organized much more tightly due to the presence of tight junctions (zonula occludens) (Wolburg and Lippoldt, *Vasc. Pharmacol.* 38 (6):323-337 (2002)). Tight junctions securely join the plasma membranes of BBB endothelial cells, leaving no gaps for the passage of fluid or molecules between endothelial cells, and thereby creating a physical barrier (Engelhardt, supra).

In addition to tight junctions, the BBB also functions as an enzymatic barrier in which a variety of enzymes in BBB endothelial cells, astrocytes, and pericytes (e.g., endopeptidase, aminopeptidases, carboxypeptidases, and cholinestaerases) effectively degrade or inactivate substrates that have entered the BBB (Pardridge, *Molec. Interventions* 3:90-103 (2003)).

It has been widely accepted that the BBB prevents virtually all molecules with a molecular weight higher than 500 Daltons from traversing its capillary wall. However, some small molecules which can cross the plasma membrane by means of lipid solubility (e.g., steroid-based hormones, ethanol and carbon dioxide), as well as those that have a molecular weight less than 400-500 Daltons are able to transit across the BBB by passive diffusion (Pardridge, supra). All other molecules capable of crossing the BBB are strictly dependent on transport systems such as carrier-mediated transport, receptor-mediated transcytosis (e.g., antibody vehicle) or absorption mediated transcytosis (Greig et al., *J. Pharmacol. Exp. Ther.* 245:581-586 (1988); Bobo et al., *Proc. Natl. Acad. Sci. USA* 91:2618-2622 (1994); Pardridge, supra).

The BBB not only functions as a diffusion barrier to molecules but also actively mediates transport of molecules between the blood and the brain. In mammals, xenobiotic transporters, including efflux and uptake transporters, have been shown to mediate drug transport cross the BBB. Three groups of transporters are: (1) the active efflux transporter (AET); (2) carrier-mediated transporter (CMT); and (3) receptor-mediated transporter (RMT). By imposing selective transports, these BBB transporters function as gate keepers to regulate influx or/and efflux of substances between the blood and the CNS. These BBB transporters are localized in both the luminal (on the blood side of the capilliary) and abluminal (on the brain side of the capillary) enthothelial membranes. The luminal and abluminal membranes are separated by about 300 nm of the endothelial cytoplasm. Thus, molecules must traverse two membranes in order to reach the brain without being targeted by digestive enzymes and efflux transporters.

Efflux transporters are of particular interest for drug development because of their importance in uptake, distribution and excretion of drugs (i.e., the concentration of a drug in the CNS is greatly affected by actions of efflux pumps). In mammals, P-glycoprotein (P-gp) is known to be the most significant active efflux transporter responsible for maintaining a functional blood-brain barrier (Schumacher and Mollgard, Histochem. Cell Biol. 108 (2):179-182 (1997)). P-gp is a ATP-dependent drug transport protein encoded by the multidrug resistance gene (MDR1/MRP1). P-gp expression is known to be an early marker of the blood-brain barrier in the developing human brain (Schumacher and Mollgard, supra). The factors that make P-gp a key determinant of drug entry into the brain or the CNS are location, potency, and broad multi-specificity (Begley, Curr. Pharm. Des. 10:1295-1312 (2004)). First, the ubiquitous localization of P-gp at both luminal and abluminal sides of the BBB supports P-gp's role as a barrier to drug entry because abluminal P-gp removes substrates from the CNS into the endothelial cytoplasm and luminal P-gp from the endothelial cell into the vascular space (Stewart et al., J. Histochem. Cytochem. 44:679-685 (1996); Demeule et al., Vascul. Pharmacol. 38:339-348 (2002)). Second, powerful ATP energy driven pumping bolsters the export capacity. Third, the remarkably wide range of specificity of P-gp ensures that it handles a large number of compounds (Bauer et al., Exp. Biol. Med. 231:118-127 (2005)). As a result, inhibition of P-gp activity or down-regulation of P-gp expression leads to prolonged retention of drugs in the CNS (Schinkel et al., Cell 77:491-502 (1994); van Asperen et al., J. Natl. Cancer Inst. 88:994-999 (1996); Rittierodt et al., Pathobiology 71 (3):123-128 (2004)).

1. Delivery of Drugs into the Brain and CNS is Limited by the Blood Brain Barrier A major challenge for treatment of most CNS disorders is overcoming the difficulty of delivering therapeutic agents to specific regions of the CNS. For treating a variety of CNS disorders, the BBB, therefore, presents the most difficult obstacle in designing a CNS therapeutic agent. In order for an agent to transit the BBB, it must possess the following characteristics: (1) a molecular weight (MW) less than 400-500 daltons; (2) lipid soluble; and (3) not a substrate for a BBB active efflux transporter or the digestive enzymes (Pardridge, NeuroRx 2 (1)-3-13 (2005)).

Moreover, most biotechnology-based therapeutics, such as monoclonal antibodies (mAbs), recombinant proteins, antisense RNA, gene therapeutics and polypeptides, and the like, cannot cross the BBB due to their molecular mass, which exceeds the 500 Dalton threshold, as well as their lipid insolubility (Pardridge, supra). It is generally believed that virtually all large molecules, and 98 percent of small molecules, do not transit the BBB (Pardridge, supra). To date, very few brain disorders, including depression, schizophrenia, chronic pain, and epilepsy, are known to be responsive to small molecule treatments. The major brain disorders, including Alzheimer's disease, Parkinson's disease, Huntington's disease, amyotrophic lateral sclerosis (ALS), multiple sclerosis (MS), brain cancer, stroke, brain injury, autism, lysosomal storage disorder, inherited ataxias, and blindness, are largely refractory to small molecule drugs. The majority of therapeutics are impermeable to the BBB and must be delivered invasively either via direct injection or by implanting a medication dispensing device into the brain or cerebrospinal fluid (CSF).

As the population ages, the number of patients with CNS diseases is increasing. It is easy to predict that the cost and demand for CNS treatments will rise over the next decade. Despite the large number of patients with CNS disorders and the fact that only a small number of therapeutic agents can transit the BBB, there are only a few pharmaceutical companies that have research programs focused on drug targeting to the CNS, in part due to the difficulty in designing and testing potential therapeutics that can transit the BBB.

2. Disadvantages of Conventional BBB Permeability Assays

Currently, there is no efficient in vivo model for assessing drug transport across the BBB. Many potential drugs that show efficacy in cell culture systems, subsequently fail in animal testing or clinical trials due to their inability to penetrate the BBB (Pardridge, supra). An effective assay that can predict drug transport in the BBB in humans is a priority for drug development for brain diseases. Methods currently available for assessing drug transport across the BBB include: 1) in silico predictive models; 2) cell-free systems; 3) cell culture systems, and 4) in vivo models.

1) In silico predictive models: Computer models are used to predict BBB transport of small molecules, based on physico-chemical properties of the drug, including molecular weight, hydrogen bonding, lipid solubility, molecular weight, and polar surface area. These models are typically validated by one of three measurements: (1) drug distribution into cerebrospinal fluid (CSF); (2) intra-cerebral dialysis fibers; and/or (3) the brain-plasma ratio (logBB). However, there are disadvantages that limit the predictive power of in silico models. First, the capillary endothelium of the BBB and choroid plexus (the blood—CSF) exhibit different expression profiles of transporter genes with different transport properties. For example, azidothymine (AZT), a treatment for HIV-1 infection in the CNS (neuro-AIDS), is readily transported into the CSF, but is blocked from transiting across the BBB (Takasawa et al., J. Pharmacol. Exp. Ther. 182:1509-1517 (1997)). Second, insertion of a dialysis fiber into brain tissue may cause various injuries to the brain or disrupt the intact BBB, thereby exposing the brain to undesirable substances.

2) Cell-free systems: Several cell-free systems have been used to predict passive permeability across the BBB, including the octanol-water partition coefficient assay. In this approach, the octanol-water phase boundary represents only a physical interface. Further, the hydrophilic/lipophilic conditions, which have not been standardized, were employed. As a result, a high variability of data exists in the literature (Lohmann et al., J. Drug Targeting 10:263-267 (2002)). The cell free system using lipid mono- and/or bi-layer vesicles appear to be superior to other cell-free systems because this system attempts to mimic the biological environment. The major draw back of this cell free assay, however, is that it cannot predict transport mechanisms other than passive diffusion because the assay focuses only on the lipid moiety of the membrane while disregarding the complexity of membrane associated and soluble enzymes which may affect the property of drugs.

3) Cell culture systems (in vitro models): To estimate the characteristic of a drug relating to BBB penetration, isolated brain capillaries and mixed cell culture systems (primary, immortalized endothelial cells and endothelial astrocyte co-culture) have also been established as in vitro BBB and blood-cerebrospinal fluid barrier (BCSFB) models. To determine cellular accumulation or transport of labeled substrates, radio- or fluorescein-labeled P-gp substrates are used. Although these studies have provided significant information on the molecular mechanisms of drug efflux, in vitro systems may not predict in vivo effects. Isolated brain capillaries cannot be used to examine the trans-endothelial transport of substrates because in vitro systems provide no information regarding which side of the endothelium the labeled substrates accumulate (e.g., the CNS or vascular space).

On the other hand, immortalized cells culture systems exhibit the advantages of high yield, homogeneity and easy quantitative analysis. Yet, all in vitro assays have failed to correlate to in vivo assays due to significant down-regulation of transport functions found in cultured cells (Regina et al., *J. Neurochem.* 71:705-715 (1998); Terasaki et al., *Drug Disc. Today* 8:944-954 (2003)). Further, non-cerebral-derived epithelial cell lines, such as Caco-2 and MDCK, exhibit poor correlation to the BBB because they lack certain essential BBB characteristics such as tight junctions (Lundquist et al., *Pharm. Res.* 19:976-981 (2002)). Another popular BBB cell culture model relies on bovine brain microvessel endothelial cells (BBMEC) co-cultured with primary astrocytes (Bachmeier and Miller, *Pharm. Res.* 22: 113-121 (2005)). This cell culture system exhibits many of the BBB components such as tight junctions as well as efflux and influx transporters. This model, however, exhibits attendant donor to donor variability and high inter-laboratory variability. Moreover, these cell lines lack intact metabolic machinery, which makes it difficult to assess the effects caused by drug metabolites.

4) In vivo models: In vivo drug permeation through the BBB can be performed in rodents using radiolabeled materials, immunohistochemistry, HPLC and microprobe/liquid chromatography approach. In the mouse brain uptake assay (MBUA), the test substance is directly injected into the mouse tail vein. Usually, concentrations of the test substance in plasma and the brain are measured after 5 minutes. In the rat micro-dialysis assay, probes are inserted into the jugular vein of the brain striatum and concentrations of the test substance in brain, blood and muscle are recorded over 3 hours, and analyzed by liquid chromatography (non-labeled substrates) or using a scintillation counter (radiolabeled substrates). These in vivo assays are extremely long, laborious and expensive.

3. The Blood Brain Barrier in Zebrafish and Other Fish

It has not been established previously whether zebrafish possesses a blood brain barrier (BBB). In zebrafish, initial neurulation occurs during the late stage of gastrulation, namely 9 hours post fertilization (hpf) (Wilson et al., *Recent Probl. Cell Diff.* 40:181-205 (2002)). By 30 hpf, four separate brain ventricles form and are visible throughout embryonic development (Wilson et al., supra). By 3 dpf, an extensive vasculature surrounding the brain can be observed and continues remodeling throughout development (Lawson and Weinstein, *Dev. Biol.* 248:307-318 (2002)). These data were collected from zebrafish embryos cultured at 28° C. However, it is well known in the art that the rate of embryonic development of the zebrafish may change depending on the growth conditions (e.g., the water temperature), as well as the strain (Westerfield, supra).

There is evidence supporting that the BBB exists in some species of fish. For example, in teleosts, several studies have analyzed the flow of blood, as well as neural amino acid, into the brain. The brain tissue in catfish *Ictalurus punctatus*, has been found receive less than 1% of total blood flow, suggesting that a certain type of barrier exists between the periphery capillary and the brain (Schultz et al., *J. Fish Biol.* 54:1275-1286 (1999)). Furthermore, rainbow trout has been shown to possess a specialized neural tryptophan transport system which is saturable and stereo-specific for large neutral amino acids (Aldegunde et al., *J. Exp. Zool.* 282:285-289 (1998)). In elasmobranches, the existence of a transport system for neural amino acid, namely glycine, has been demonstrated in the dogfish (Abbott et al., *J. Physiol.* 25P (1988)).

C. Methods of Screening an Agent for an Activity in the Brain or CNS

The present invention provides methods of screening an agent for an activity in the brain or central nervous system (CNS) in a vertebrate animal, such as a teleost, preferably a zebrafish, in vivo. The term "activity" as used herein refers to a process, function, or activity of the living organism. Such an activity can be a biological activity that normally occurs in the organism, or it can be an activity that occurs in response to the agent being administered to the organism. An activity in the brain or CNS includes, for example and not for limitation, developmental defects as defined in Section II above, cell death activity (i.e., apoptosis or necrosis) as defined in Section III above, and toxic activity as defined in Section IV above. The methods are applicable for use in zebrafish that are transparent or translucent (i.e., optically clear) at the embryonic, larval, or adult stage.

In one aspect, the invention provides methods of screening an agent for an activity in the brain or CNS in a zebrafish in vivo. Some such methods of screening involve screening an agent for an activity in the brain or CNS of a zebrafish based on the knowledge as to whether the agent is able to penetrate, diffuse, or be transported into the brain or CNS of the zebrafish, and whether the BBB of the zebrafish has been formed and/or is functional to transport molecules out of the brain or CNS.

First, an agent known for its ability to transit the BBB of an organism may be examined in zebrafish in which the BBB has fully developed, thereby allowing assessment of its ability to exert a desired activity. An agent known for its ability to transit the BBB of an organism may also be examined in zebrafish in which the BBB has not yet formed.

Second, an agent known for its inability to transit the BBB may be examined in zebrafish embryos that have not yet formed a functional BBB. Alternatively, the agent may be directly delivered to the brain or CNS in zebrafish in which the BBB has formed, thereby testing the agent's ability to exert the desired activity without impediment associated with its inability to transit the BBB.

Third, an agent unknown for its ability to transit the BBB of an organism may be tested in zebrafish embryos whose BBB has not yet formed (i.e., zebrafish prior to 3 dpf). This approach allows the assessment of the agent's property relating to a desired biological activity. If the agent exhibits the desired biological activity, it can be further tested for its ability to exert the desired biological activity using zebrafish embryos in which the BBB has fully developed. If the agent is able to exert the desired activity in zebrafish with a functional BBB (i.e., zebrafish at least 3 dpf), it may be concluded that the agent can transit the BBB. If not, it may be concluded that the agent is unable to transit the BBB. Alternatively, the agent may be directly delivered to the brain or CNS in zebrafish in which the BBB has formed, thereby testing the agent's ability to exert the desired activity without impediment associated with its inability to transit the BBB.

The invention is applicable to screening for an agent wherein the agent is assessed for a biological effect that alters an activity or function in the brain or CNS, and the biological effect can be therapeutic, prophylactic, or toxic.

The invention is applicable to screening for an agent to determine whether the agent exerts a beneficial (e.g., therapeutic or prophylactic) or harmful (e.g., toxic or drug side effects to the CNS) biological effect.

A variety of methods to test for the presence of the BBB in early development of the zebrafish were performed to demonstrate the feasibility of using zebrafish as an in vivo model for screening drugs for an activity in the brain or CNS.

1. The Presence of Tight Junctions in 3 dpf Zebrafish

The first level of physical barrier in the BBB is presented by the endothelial tight junction. Tight junctions are the closely associated areas of two endothelial cells whose membranes are joined together forming a virtually impermeable barrier to fluid. They perform three vital functions: (1) they hold cells together; (2) they block the movement of integral membrane proteins; and (3) they prevent the passage of molecules through the paracellular space (the space between the cells). Thus, in order for an agent to penetrate the BBB, materials must actually enter the endothelial cells either via diffusion or the transport systems.

The presence of tight junctions between BBB endothelial cells in 3 dpf zebrafish embryos cultured under standard conditions as described above was demonstrated using immunostaining (FIG. 19). ZO-1 is a component of tight junctions formed between endothelial cells in the mammalian brain. A mouse monoclonal antibody against rat ZO-1 (Sigma, St. Louis, Mo.) was used in whole mount immunostaining. Zebrafish embryos at 3 dpf were fixed in Dent's fixative (DMSO: MeOH=1:4) for at least 3 hours at room temperature or overnight at 4° C. Embryos were dehydrated to 100% methanol and incubated for at least 1 hour at −20° C. Embryos were then rehydrated step-wise to 100% PBST (0.1% Tween-20 in PBS). Embryos were treated with 1M $NH_4Cl$ for 2-3 hours at room temperature to quench autofluorescence. Embryos were washed in PBST twice for 30 minutes each at room temperature by gentle shaking. Embryos were then washed with PBST three times for 10 minutes each. Embryos were incubated in blocking solution for 1 hour at room temperature with gentle shaking. Embryos were then incubated with primary antibody at 4° C. overnight. Embryos were washed extensively with large volume of PBST, at least 4 times for 1 hour each. Embryos were then incubated with secondary antibody for 2 hours at room temperature. Embryos were washed with PBST twice and three times with PBS for 10 minutes in each wash. Embryos were equilibrated into citrate buffer (pH 5) for at least 20 minutes. Citrate buffer was drained off and HRP substrate TMB (100 µl) was added. Embryos were incubated for 30 minutes. The reaction was stopped with 2M $H_2SO_4$ and embryos were examined under a fluorescence microscope.

Fluorescence microscopy was performed using a Zeiss M2bio fluorescence microscope (Carl Zeiss Microimaging Inc., Thornwood, N.Y.), equipped with a rhodamine cube and a green FITC filter (excitation: 488 nm, emission: 515 nm), and a chilled CCD camera (Axiocam MRM, Carl Zeiss Microimaging Inc., Thornwood, N.Y.). 1.6×, 10× and 20× objective archromats and 10× eye pieces were used for the magnification. The system is also equipped with a z-motorized stage, deconvolution software and 4-D reconstruction software (Axiovision, Carl Zeiss Mircroimaging Inc., Thornwood, N.Y.), which permits reconstruction of 3-D objects and analysis of Z-stacks. Images were processed with Axiovision software Rel 4.0 (Carl Zeiss Microimaging Inc., Thornwood, N.Y.), and the Adobe Photoshop 6.0 computer program (Adobe, San Jose, Calif.). All procedures were performed according to the manufacturer's specifications.

As shown in FIG. 19, whole mount ZO-1 antibody immunostaining revealed that tight junctions form in the 3 dpf zebrafish brain (brown spots) adjacent to the mesencephalic vein (MsV), middle cerebral vein (MCeV), and prosencephalic artery (PrA) (Arrows). This result demonstrates that tight junctions are present in zebrafish at 3 dpf, but are not seen in zebrafish at 2 dpf (data not shown).

2. Evans Blue Extravasation/Exclusion Assay

Evans blue (MW=961 Daltons) has been widely used as a vital dye to investigate vascular structures and injuries, and the Evans blue dye extravasation assay has been used in other organisms to determine BBB permeability. Injected into circulation, this dye is confined to the blood vessels within the zebrafish brain at 3 dpf, but freely diffuses through vessels and tissue outside the brain (FIG. 20). No such impediment to diffusion through any vessels is seen at zebrafish embryos at 2 dpf (FIG. 20). This result, in combination with the presence of tight junction shown in FIG. 19 above, clearly indicates that a functional BBB forms in zebrafish and is capable of excluding molecules larger than 961 Daltons as early as 3 dpf. Because the BBB is formed gradually with time, the size of compounds that are excluded by the BBB may get smaller as the formation of the BBB progresses beyond 3 dpf. Furthermore, it is well known in the art that zebrafish development (e.g., embryonic development) is affected by the conditions under which the zebrafish is cultured, in particular the water temperature, and can be controlled to some extent by varying such conditions. For example, a zebrafish embryo develops more rapidly at higher temperatures (e.g., 35° C.) and more slowly at lower temperatures (e.g., 18° C.) than it does at a standard temperature (i.e., 28° C.), as used herein. Accordingly, the time of formation of a functional BBB system as described herein may vary depending upon the particular growth conditions under which the zebrafish are maintained, as well as the zebrafish strain.

3. Agents to be Screened

Agents to be screened for an activity in the brain or CNS in vivo in teleosts, preferably zebrafish, are described in Section I (B) above.

4. Administration of Agents

Agents to be screened for an activity in the brain or CNS in vivo in teleosts, preferably zebrafish, can be administered as described in Section I (C) above.

Examples

As provided hereinabove in Sections II, III and IV, several compounds were screened for in vivo activity in the brain or CNS of zebrafish embryos, cultured under standard conditions, at various times post-fertilization. The results are summarized below in which the compounds tested are classified according to the knowledge, at the time of testing, of their ability to transit the BBB.

1. Compounds Known to Transit the Blood Brain Barrier

As shown in Table 7 below, several compound known in the art to transit the BBB in mammalian organisms were tested for, and demonstrated, biological activity in the brain or CNS of zebrafish embryos cultured under standard conditions when administered for various periods of time, including prior to 3 days post-fertilization or after at least 3 days post-fertilization.

2. Compounds Known not to Transit the Blood Brain Barrier

As shown in Table 7 below, several compound known in the art not to transit the BBB in mammalian organisms were tested for biological activity in the brain or CNS of zebrafish embryos cultured under standard conditions when administered for various periods of time, including prior to 3 days post-fertilization or after at least 3 days post-fertilization. Neither VEGF nor dexamethasone demonstrated any activity in the brain or CNS of zebrafish embryos.

3. Compounds not Known to Transit the Blood Brain Barrier

As shown in Table 7 below, compounds that were unknown as to their ability to transit the BBB in mammalian organisms were tested for biological activity in the brain or CNS of zebrafish embryos cultured under standard conditions when administered for various periods of time up to 3 days post-fertilization. Some compounds from the NCI and MIT compound libraries demonstrated developmental defects in the brain or CNS of zebrafish embryos.

ability to alter or modify the compound-induced brain or CNS disease or disorder. Two examples of such a strategy are provided below.

1) Compound Effects in a Zebrafish Model of Parkinson's Disease 2 day post-fertilization zebrafish embryos cultured under standard conditions as described above were used to examine effects of deprenyl on dopaminergic neuron activity. Zebrafish embryos were treated with 0.1% DMSO (control), 200 μM 6-hydroxydopamine (6OHDA), or 200 μM 6-hydroxydopamine plus 200 μM deprenyl (FIG. 21). Zebrafish embryos were fixed and then immunostained using anti-hydroxylase antibody to examine dopaminergic neurons (DA) in diencephalons. 6OHDA induces DA neuron loss which mimics neuron loss observed in Parkinson's disease. 6OHDA treatment induced DA neuron loss in zebrafish, however, deprenyl treatment prevented 6OHDA-induced DA neuron loss (FIG. 21).

2) Compound Effects in a Zebrafish Model of Multiple Sclerosis 4-day post-fertilization zebrafish embryos cultured under standard conditions as described above were used to examine effects of 4-methylcatechol on integrity of the myelin sheath. Zebrafish embryos were treated with 0.1% DMSO (control), 6.5 mM acrylamide, or 6.5 mM acrylamide plus 5 μM 4-methylcatechol (4-MC) (FIG. 22). The myelin sheath was examined in the CNS (oligodendrocytes: 0) and in the PNS (Schwann cells: S) by in situ hybridization using riboprobes against myelin basic protein (MBP). 4-MC is a potent stimulator of nerve growth factor (NGF) synthesis. Acrylamide treatment decreased expression of MBP in oligodendrocytes and Schwann cells, mimicking the loss of MBP expression and reduced myelin sheath integrity seen in multiple sclerosis patients. As shown in FIG. 22, 4-MC treatment was able to rescue the acrylamide-induced loss of MBP.

TABLE 7

| Compound Type | Compound Name | Treatment | Activity* |
| --- | --- | --- | --- |
| 1. Compounds known to transit the BBB | Fumagillin derivative TNP-470, some MIT compounds | 24 hpf-72 hpf, soaking | Developmental delay, axial defects |
| | Some NCI compounds | 24 hpf-72 hpf, soaking | Developmental delay, axial defects, cranial defects |
| | Retinoic Acid | 24 hpf for 24 hours; 12-14 hpf for 2 hours | Apoptosis |
| | Ibuprofen | 24 hpf for 2 hours | Apoptosis |
| | Aspirin | 24 hpf-120 hpf | Toxicity (teratogen, kidney, muscle contraction, erratic meovements) |
| 2. Compounds known not to transit the BBB | VEGF | 24 hpf-72 hpf, microinjection into the blood stream | Angiogenesis, no observed effect in brain or CNS |
| | Dexamethasone | 24 hpf-72 hpf, soaking; 24 hpf-120 hpf, soaking; 96 hpf-120 hpf, soaking | Toxicity (liver and gastrointestinal) |
| 3. Compounds with unknown ability to transit the BBB | Majority of NCI compounds | 24 hpf-72 hpf, soaking | Developmental delay, axial defects, cranial defects |
| | Some MIT compounds | 24 hpf-72 hpf, soaking | Developmental delay, axial defects |

*Compounds were tested for the following activities: developmental defects (i.e., developmental delay, axial defects, cranial defects) in Section II; apoptosis in Section III; and toxic activity (e.g., organ-specific toxicity, growth inhibition, teratogenesis) in Section III.

4. Zebrafish Models of Brain or CNS Diseases or Disorders

To date, very few brain diseases or disorders, including depression, schizophrenia, chronic pain, and epilepsy, are known to be responsive to small molecule treatments. The major brain disorders, including, Alzheimer's disease, Parkinson's disease, Huntington's disease, amyotrophic lateral sclerosis (ALS), multiple sclerosis (MS), brain cancer, stroke, brain injury, autism, lysosomal storage disorder, inherited ataxias, and blindness, have been largely refractory to small molecule drugs. One strategy to identify new small molecule drugs to treat brain or CNS diseases or disorders is to administer a compound to a teleost, preferably a zebrafish, in which the compound induces a phenotype that mimics a brain or CNS disease or disorder, and then screen agents for their 5. Screening for Neurotoxicity or Neuroprotective Activity in Zebrafish 3-day post-fertilization zebrafish embryos cultured under standard conditions as described above were used to screen for neuroprotectants in vivo. Zebrafish embryos were treated with L-hydroxyglutaric acid (LGA), which caused oxidation and apoptosis in zebrafish. Zebrafish embryos were treated with vehicle alone (A), 50 mM LGA alone (B), or 50 mM LGA plus D-methonine (D-Met, 1 µM) (C), indole-3-carbinol (1 µM) (D), deferoxamine (DFO, 1 µM) (E), dihydroxybenzoate (DHB, 1 µM) (F), deprenyl (0.1 µM) (G), N(G)-nitro-L-arginine methyl ester (LNAME, 1 µM) (H), N-acetyl L-cystein (L-NAC, 5 µM) (I), 2-oxothiazolidine (OTC, 10 µM) (J), lipoic acid (10 µM) (K), minocycline (10 µM) (L), isatin (100 µM) (M), cortisone (10 µM) (N), ascorbic acid (100 µM) (O), α-tocopherol (100 µM) (P), or buthionine sulfoximine (BSO, 10 µM) (Q) (FIG. 23). BSO was used as a negative control.

After exposure for 24 hours, zebrafish were washed with fish water three times, and immersed in 1 µg/ml acridinium chloride hemi-[zinc chloride] (Sigma-Aldrich) (AO) in fish water for 60 min. Zebrafish were rinsed thoroughly in fish water three times (5 min/wash), and anaesthetized with 0.5 mM 3-aminobenzoic acids ethyl ester, 2 mM $Na_2PO_4$ (ME-SAB), then oriented on their ventral side and mounted with meythlcellulose in a depression slide for observation by fluorescence microscopy to examine brain apoptosis. All images were focused in the dorsal brain region (anterior on top, posterior on bottom, dorsal on front) and inverted. Apoptotic cells displayed a punctate fluorescent staining pattern (black dots). D-Met, DFO, DHB, deprenyl, L-NAME, L-NAC, OTC, lipoic acid, minocycline, isatin and cortisone exhibited protection from the effects of LGA, whereas indole-3-carbinol, ascorbic acid and α-tocopherol showed no significant protection from LGA, at the concentrations tested (FIG. 23). Dose-response curves of neuroprotectants at different concentrations (0-250 µM) were generated (data not shown). One-way ANOVA and Dunnett's t-test were used to determine the significance: D-Met, DFO, DHB, deprenyl, L-NAME, L-NAC, OTC, lipoic acid, minocycline, isatin and cortisone exhibited significant protection ($P<0.05$), whereas indole-3-carbinol, ascorbic acid and α-tocopherol, which are not BBB permeable, showed no significant protection ($P>0.05$).

D. Methods of Screening an Agent for an Ability to Affect Blood Brain Barrier Permeability The present invention provides methods of screening an agent for its ability to exert an activity on the permeability of the blood brain barrier (BBB) of a vertebrate animal, such as a teleost, preferably a zebrafish, in vivo. The term "activity" as used herein refers to a process, function, or activity of the living organism. An activity can be a biological activity that normally occurs in the organism, or it can be an activity that occurs in response to the agent being administered to the organism. The methods are applicable for use in zebrafish that are transparent or translucent (i.e., optically clear) at the embryonic, larval, or adult stage.

In one aspect, the invention provides methods of screening an agent for an ability to affect BBB permeability in a zebrafish in vivo. Some such methods of screening involve screening an agent for an ability to affect BBB permeability in a zebrafish based on the knowledge as to whether the agent is able to penetrate, diffuse, or be transported into the brain or CNS of the zebrafish, and whether the BBB of the zebrafish has been formed and/or is functional to transport molecules out of the brain or CNS.

1. The BBB Efflux/Influx Assay

A reproducible fluorescent method was developed to detect drug influx and efflux across the BBB. Efflux transporters are of particular interest for drug development because of their importance in uptake, distribution and excretion of drugs. The best known and most widely studied efflux transporter is P-glycoprotein (P-gp), which is an ATP-dependent drug transporter encoded by the multidrug resistance gene (MDR1/MRP1). P-gp is the most important active efflux transporter and responsible for the majority of efflux transportation in the BBB (Tsuji et al., *Life Sci.* 51:1427-1437 (1992); Stewart et al., *J. Histochem. Cytochem.* 44:679-685 (1996); Schinkel, *Adv. Drug Deliv. Rev.* 36:179-194 (1999)). Inhibition of P-gp leads to drug retention in the CNS. For example, MDR1a knockout mice lacking P-gp showed a hundred-fold increase in drug absorption and decrease in drug elimination in the CNS, indicating the importance of P-gp in drug efflux (Schinkel et al., *Cell* 77:491-502 (1994); van Asperen et al., *J. Natl. Cancer Inst.* 88:994-999 (1996)). Enhanced drug sensitivity has also been observed in collie dogs with a homozygous deletion of the MDR1 gene and a premature termination of P-gp (Mealey et al., *Pharmacogentics* 11:723-733 (2001)). In addition, a number of preclinical and clinical studies have shown that polymorphisms of MDR genes can be a factor in the overall outcome of pharmacotherapy (Bauer et al., Exp. Biol. Med. 231:118-127 (2005)). In dogfish shark, xenobiotic efflux pumps, MRP2, have been identified in brain capillaries which are sensitive to different glycoprotein inhibitors and substrates, similar to the responses exhibited by those in mammals (Miller et al., *Am. J. Reg. Integ. Comp. Physiol.* 282:R191-R198 (2002)).

Design of drugs that are not P-gp substrates is one strategy to increase drug permeability to the CNS. Finding compounds that are P-gp specific inhibitors is another strategy because inhibitors may be useful in increasing drug permeability to the brain in a co-treatment drug regimen (Kemper et al., *Eur. J. Cancer* 40:1269-1274 (2004)). To develop a predictive zebrafish BBB assay to determine if drugs are potential P-gp inhibitors, two P-gp fluorescent substrates, rhodamine 123 and FITC-HRP, were administered to zebrafish in the presence of known P-gp modulators (i.e., inhibitors).

2. Expression of P-gp (MRP1) in Zebrafish

To confirm whether the zebrafish possesses a BBB and expresses P-gp, expression of MRP1 was assessed in zebrafish cultured under standard conditions as described above at 24 hpf (FIG. 24). Whole mount in situ hybridization was performed to examine expression of MRP1 RNA using sense (negative control) and anti-sense riboprobes. As shown in FIG. 24A, the sense RNA probe did not detect any signals. In contrast, the anti-sense RNA probe detected expression of MRP1 in the brain and spinal cord regions at 24 hours (FIG. 24B).

1) Riboprobe labeling: This procedure utilized plasmid vectors containing SP6, T3, or T7 promoters for RNA polymerase. Zebrafish EST sequence was purchased from Research Genetics (currently Invitrogen, Carlsbad, Calif.). The vector was linearized depending on whether or not 'sense' or 'antisense' RNA is required. The full length cDNA (EST clone) was used as template to synthesize digoxigenin-labeled RNA probes according to the manufacturer's protocol (Boehringer Mannheim Biochemicals, Indianapolis, Ind.).

2) Whole mount in situ hybridization: Embryos were fixed with 4 percent paraformaldehyde in PBS and re-hydrated with PBST. The RNA probes were hybridized at 65° C. in hybridization solution (50% formamide, 5×SSC, 0.1% Tween 20, 0.05 mg/ml Heparin, 0.5 mg/ml tRNA, 10 mM sodium Citrate buffer pH 6.0). Alkaline phosphatase-conjugated anti-digoxigenin antibody was used to detect signals. For staining, embryos were equilibrated in NTMT buffer (0.1 M Tris/HCl pH 9.5, 50 mM MgCl, 0.1 M NaCl, 0.1% Tween 20) at room temperature. Once the embryos were equilibrated, 4.5 µl of 75 mg/ml NBT (Nitro Blue Tetrazolium) and 3.5 µl of 50 mg/ml BCIP (5-Bromo-4-Chloro-3-Indolyl-Phosphate) per ml were added to the staining solution. The staining reaction was stopped by washing the embryos with PBST. Embryos were then examined on a stereo-dissecting microscope.

3. Expression of Transporter Genes in Zebrafish

Table 8 below summarizes RNA expression data demonstrating the expression in zebrafish of transporter genes that are known to be involved in regulating BBB function in other organisms, further indicating the presence of a functional BBB in zebrafish.

air-pressure controlled microinjector (WPI, Sarasota, Fla.). The distribution of fluorescent dyes was recorded at both 15 minutes and 4 hours after microinjection in the same animals to monitor efflux using epifluorescence microscopy.

2) Fluorescence microscopy and image analyses: All fluorescence microscopy was performed using a Zeiss M2Bio fluorescence microscope (Carl Zeiss Microimaging Inc., Thornwood, N.Y.), equipped with a rhodamine cube and a green FITC filter (excitation: 488 nm, emission: 515 nm), and a chilled CCD camera (Axiocam MRM, Carl Zeiss Microimaging Inc., Thornwood, N.Y.). Screens were routinely performed using: 1.6×, 10× and 20× objective archromats and 10× eye pieces. The system is also equipped with a z-motorized stage, deconvolution software and 4-D reconstruction software (Axiovision, Carl Zeiss Microimaging Inc., Thornwood, N.Y.), which permits reconstruction of 3-D objects and analysis of Z-stacks. Images were processed with

TABLE 8

| Protein Product | Gene name | Function | Accession # |
| --- | --- | --- | --- |
| P-glycoprotein (multidrug resistance protein) | MDR1/MRP1 | Efflux transport | BI533101 |
| Multidrug resistance associated protein 2 | MRP2 | Efflux transport | BC056740 |
| Blood-brain barrier specific anion transporter 1 (Organic anion transporting polypeptide 1C1) | SlC21;14 | Efflux transport | CA472133 |
| Organic anion transporting polypeptide 2 | OATP 2 | Efflux transport | AI353630 |
| Breast cancer resistance protein | BCRP1 or ABCG2 | Efflux transport | AL920536 |
| Glucose carrier, L1 amino acid transporter | GLUT1 | Uptake carrier | AW175259 |
| Large neutral amino acid transporter | LAT1 | Uptake carrier | BI887805 |

4. Efflux Machinery and Inhibition of Zebrafish P-gp by Verapamil

To confirm that zebrafish P-gp is sensitive to inhibition to known mammalian P-gp inhibitors, 3-dpf zebrafish cultured under standard conditions as described above were incubated with vehicle alone (A and B) or 30 µM verapamil for 24 hours (C and D) (FIG. 25). Verapamil is a commonly known P-gp inhibitor in in vivo rodent BBB models (Henthorn et al., *Pharmacology* 289:1084-1089 (1999)).

In control (vehicle alone), after 4 hours, the fluorescent dye entered blood vessels including the peripheral blood vessel (data not shown) and exhibited a less intense staining pattern, indicating active efflux transport of FITC-HRP (FIG. 25B). In contrast, with verapamil treatment, after 4 hours, the fluorescent dye was retained in the brain region and exhibited strong staining throughout the brain (FIG. 25D), indicating that verapamil inhibited P-gp efflux in zebrafish. Similar results were obtained in efflux studies using another common P-gp substrate, rhodamine 123 (data not shown). Two compounds, caffeine and phenyloin, which are known to transit the BBB by a P-gp independent pathway (i.e., passive diffusion), were also used as negative controls. Treatment of zebrafish with these P-gp independent compounds did not affect P-gp efflux (data not shown). Together, these data provide supporting evidence that a functional BBB exists in zebrafish during early zebrafish development and that zebrafish P-gp is functionally equivalent to P-glycoproteins found in mammals.

1) Microinjection of dye: FITC-HRP (100 µM), a fluorescent P-gp efflux substrate, was delivered by microinjection (Meng et al., *Meth. Cell Biol.* 60:133-148 (1997)) into the brain region (injection site is the middle line of the hindbrain ventricle) of 4 dpf zebrafish following the drug treatment. Other vital dyes (e.g., rhodamine 123) can be also employed for the same purpose. Microinjection was performed using an Axiovision software Rel 4.0 (Carl Zeiss Microimaging Inc., Thornwood, N.Y.) and the Adobe Photoshop 6.0 computer program (Adobe, San Jose, Calif.). All procedures were performed according to the manufacturer's instructions.

3) Morphometric analysis: Fluorescence intensity in the brain was measured using Scion Image System (Scion Corporation, Frederick, Md.). Images of the dorsal side in each animal were obtained using the same exposure time and fluorescence gain. Ten animals for each treatment were quantified and intensity of fluorescent signals was averaged. Retention and efflux of fluorescent dye in the brain regions was quantified by comparing the fluorescence signals at 15 minutes after dye injection (SS: 0: staining signals at zero time point), and at 4 hours after dye injection (SS4: staining of signal at the end of time point) (FIG. 26). Retention of fluorescent signals (RFS) in each animal was calculated using the following formula:

RFS=SS4/SS0×100%.

A working example of morphometric analysis is provided in FIG. 26 in which the fluorescent signals in the brain were quantified. In controls, SS0 was 9,658,955 (A) and SS4 was 541,787 (B); the RFS was 5.6%, indicating that most of fluorescent dye in the brain had been eliminated. With verapamil treatment, the SS0 was 10,085,802 (C), SS4 was 5,575,444 (D), and the RFS was 55.3%. Compared to untreated control (B), verapamil increased RFS from 5.6% to 55.3% (D), a significant 10-fold increase in fluorescence retention. This result suggested that verapamil impaired P-gp function, thereby increasing retention of fluorescent dye in the zebrafish brain.

4) Statistics: All data were presented as mean±SE (standard error of the mean). Student's t-test was employed to compare drug treated fish with the controls. Efficacy was defined as $P<0.05$, $n=5$. All the variables were independent. In addition, analysis of variance between groups (ANOVA) was used to compare drug effects for multiple comparisons. One-factor ANOVA was used first and Tukey HSD pair wise comparison post hoc tests was used next to determine significant differences between treatments. P values<0.05 was considered significant.

5) Embryo handling: Zebrafish were generated by natural pair-wise mating in our aquaculture facility, as described by Westerfield, The Zebrafish Book: a Guide for the Laboratory use of Zebrafish, The University of Oregon Press (1993). 4-5 pairs were set up for each mating; on average 100-150 embryos per pair will be generated. Embryos were maintained in embryo water (5 g of Instant Ocean Salt with 3 g of $CaSO_4$ in 25 liters of distilled water) at 28° C. for approximately 24 hours before sorting for viability. Because the fish embryo receives nourishment from an attached yolk ball, no additional maintenance was required. To preserve optical clarity, fish water containing 0.003% PTU (1-phenyl-2-thiourea, Sigma, St Louis, Mo.) was employed during the entire experimental period because low concentration of PTU has been shown to cause depigmentation, but no significant effect on any biological function (Westerfield, supra). Alternatively, if PTU causes unexpected problems, an albino zebrafish, which has mutated pigmentation, can be used.

5. Zebrafish P-gp Efflux Assay

The P-gp transporter can transport a wide range of structurally unrelated compounds. To examine the pharmacologic response of zebrafish P-gp, different classes of compounds can be employed. Zebrafish at least 3-dpf can be treated for 24 hours by soaking with different concentrations of test agents, 0 (vehicle control), 1, 10, 100 and 1000 µM. Each agent can be tested in 10 animals. After 24 hours drug treatment, the P-gp efflux assay is performed. To determine time course response, initially two time points after injection is assessed: 15 min. and 4 hours. If necessary, other time points, for example and not for limitation, 2, 6, 8, 16, 24 hours or longer time, can be recorded for the same animals.

The rationale for this approach is that if the function of P-gp is compromised in the presence of P-gp inhibitors, efflux of FITC-HRP or rhodamine-123 should decrease and the dye will accumulate in the zebrafish brain. In contrast, in the presence an agent which has no effect on P-gp function (P-gp non-inhibitor), efflux of FITC-HRP or rhodamine-123 should resemble that of negative controls (e.g., P-gp independent compounds: caffeine and phenyloin).

6. Agents to Be Screened

Agents to be screened for in vivo activity in the brain or CNS in teleosts, preferably zebrafish, are described in Section I (B) above.

7. Administration of Agents

Agents to be screened for in vivo activity in the brain or CNS in teleosts, preferably zebrafish, can be administered as described in Section I (C) above.

8. Administration of Dyes

Dyes used in methods of screening agents for an ability to affect in vivo BBB permeability in teleosts, preferably zebrafish, can be administered as described in Section I (D) above.

A dye can be rhodamine-123 or FITC-HRP or any equivalents thereof.

A dye can be administered alone, in conjunction with a variety of solvents (e.g., 10% EtOH, Saline, dimethylsulfoxide or the like) or carriers (including, e.g., peptide, lipid or solvent carriers), or in conjunction with other compounds.

The dye efflux assay is performed on zebrafish embryos of age at least 3 dpf in which a functional BBB with active P-gp have been established.

9. Morphometric Analysis

Although qualitative, visual assessment of staining is sufficient for assessing significant changes in efflux of fluorescent substrate, quantitative information is desirable for dose-response analysis and comparison of efficacy. The aim of quantitative analysis is to assign a value (or range of values) to the visual photomicrograph which can provide a measure of efflux of fluorescent substrate.

To quantify the fluorescence intensity within the brain region, the fluorescence images of the brain from each animal (anterior on the top; posterior on the bottom; dorsal on the front) can be obtained using Scion Image System (Scion Corporation, Frederick, Md.) or any equivalents thereof. Images of the brain in each animal can be obtained using the same exposure time and fluorescence gain.

The sum of staining signals (SS) in the midbrain can be quantified by image analysis (e.g., Scion Image) which measures positive staining signals in the midbrain using strict logarithms in defined areas and signal threshold.

Multiple animals for each treatment can be employed to obtain an average of the staining signals (the average fluorescent intensity).

The retention of fluorescent dye in the brain region can be further quantified by the following calculation:

$$\text{fluorescent signals(SS)} = \text{staining area} \times \text{average fluorescent intensity}.$$

Analytic parameters including signal threshold, stained area and background can be further defined for automated high-content analysis. Because all quantitative analysis inherently includes some method based errors, a preferred embodiment is the variable frame method instead of the fixed frame method in order to minimize errors in quantifying the fluorescence signals.

The dye efflux in each animal can be further calculated by comparing the fluorescent signals within the brain at 15 min after dye injection (SS0: staining signals at zero time point; 15 min is required for sample preparation and fluorescence imaging), and fluorescent signals at 4 hours after dye injection (SS4: staining of signals at the end of time point). Although the preferred method is to measure the fluorescent intensity at the initial time point and 4 hours following the administration of dye, the fluorescent intensity within the brain can be obtained in various time points depending on the conditions of the assay.

The retention of fluorescent signals (RFS) in each animal is further refined by normalizing the amount of injected fluorescent dye.

The retention of fluorescent signals (RFS) in each animal is further calculated using the following formula:

$$RFS = SS4/SS0 \times 100\%.$$

The RFS of drug treated animal (RFSc) can be compared to RFS of untreated control (RFSd) to evaluate drug effects on efflux. Significant inhibition of P-gp is defined as $\geq 200\%$ increase in RFS in the brain (RFSd $\geq 2 \times$ RFSc) after drug treatment.

A dose response curve for each compound can be generated by drawing a correlation between RFS and drug concentration (RFS vs. concentration).

Dye efflux kinetics for a test agent can be obtained by measuring the fluorescent intensity of dye in a time course manner, thereby identifying an optimal efflux time point inherently associated with the test agent.

A working embodiment of morphometric analysis is provided in FIG. 26 wherein fluorescent signals in the brain was quantified.

An exemplary flow chart of screening method for compounds having an effect on blood brain barrier (BBB) permeability in zebrafish as quantified by morphometric analysis is provided in FIG. 27. In this screening method, the compounds are optionally assayed for an activity in the brain or CNS of zebrafish. The assays to screen the compounds for an activity in the brain or CNS and ability to affect BBB permeability can be performed simultaneously, sequentially in either order, or separately, depending on whether the compounds are known to transit the BBB, known not to transit the BBB, or it is not known whether the compounds transit the BBB. Compounds known to transit the BBB may be screened for an activity in the brain or CNS using zebrafish embryos of any age. Such compounds can be assayed for their effect on BBB permeability simultaneously, sequentially in either order, or separately. Compounds known not to transit the BBB, and compounds not known as to their ability to transit the BBB, may be screened for an activity in the brain or CNS using zebrafish embryos of age less than 3 dpf (i.e., before the formation of the BBB). Such compounds can be assayed for their effect on BBB permeability sequentially, with the BBB permeability assay performed second, or separately.

Example

1. Effect of N-acetyl-L-aspartyl-L-glutamate (NAAG) on Blood Brain Barrier Permeability in Zebrafish 4 day zebrafish embryos cultured under standard conditions as described above were used to examine effects of N-acetyl-L-aspartyl-L-glutamate (NAAG), an agonist at group II metabotropic and NR1/NR2D-containing N-methyl-D-aspartate (NMDA) ionotropic glutamate receptors, on BBB integrity. Rhodamine 123 was injected to the tail veins to detected BBB integrity. In control zebrafish, Rohdamine 123 was observed in the blood vessels at 15 min and 4 hours after injection indicating a functioning BBB system (FIG. 28, left panels). In contrast, Rhodamine 123 was observed in brain tissue 4 hours after injection, indicating increased BBB permeability in response to NAAG (FIG. 28, right panels). This data further demonstrates that zebrafish embryos are useful for screening agents for their ability to affect BBB permeability in vivo.

While the foregoing invention has been described in some detail for purposes of clarity and understanding, it will be clear to one skilled in the art from a reading of this disclosure that various changes in form and detail can be made without departing from the true scope of the invention. The above examples are provided to illustrate the invention, but not to limit its scope; other variants of the invention will be readily apparent to those of ordinary skill in the art and are encompassed by the claims of the invention. The scope of the invention should, therefore, be determined not with reference to the above description, but instead should be determined with reference to the appended claims along with their full scope of equivalents. All publications, references, and patent documents cited in this application are incorporated herein by reference in their entirety for all purposes to the same extent as if each individual publication or patent document were so individually denoted.

What is claimed is:

1. A method of screening an agent in vivo for an activity in the brain or central nervous system (CNS) and an ability to transit the blood brain barrier, the method comprising:
   (a) administering the agent, without regard to whether the agent penetrates the blood brain barrier, to a zebrafish embryo, wherein the zebrafish embryo is an embryo of at least the late stage of gastrulation but having not yet developed a blood brain barrier comprising tight junctions when initially contacted with the agent, whereby when cultured at a standard temperature of about 28° C. the zebrafish embryo is aged at least about nine hours post fertilization but less than three days post fertilization when initially contacted with the agent;
   (b) detecting a response in the brain or CNS of the agent-treated zebrafish of step (a) in vivo;
   (c) comparing the response in the brain or CNS of the agent-treated zebrafish of step (a) with a response in the brain or CNS of an untreated or control zebrafish, wherein a difference in the response in the brain or CNS of the agent-treated zebrafish of step (a) compared to the response in the brain or CNS of the untreated or control zebrafish is indicative of the agent having activity in the brain or CNS;
   (d) if the agent is determined by step (c) to have activity in the brain or CNS, administering the agent to a zebrafish having a blood brain barrier comprising tight junctions when initially contacted with the agent, whereby when cultured at a standard temperature of about 28° C. the zebrafish is aged at least three days post fertilization when initially contacted with the agent;
   (e) detecting a response, if any, in the brain or CNS of the agent-treated zebrafish of step (d); and
   (f) comparing the response in the brain or CNS of the agent-treated zebrafish of step (d) with a response in the brain or CNS of an untreated or control zebrafish, wherein a difference in the response in the brain or CNS of the agent-treated zebrafish of step (d) compared to the response in the brain or CNS of the untreated or control zebrafish is indicative of the agent having an ability to transit the blood brain barrier.

2. The method of claim 1, wherein the agent is administered to the zebrafish embryo by dissolving the agent in the media containing the zebrafish embryo.

3. The method of claim 1, wherein the method is performed in a multi-well format.

4. The method of claim 3, wherein a single zebrafish embryo occupies at least some of the wells.

5. The method of claim 1, wherein the zebrafish embryo is aged at least about 12 hours post fertilization when cultured at a standard temperature of about 28° C.

6. The method of claim 1, wherein the zebrafish embryo is aged at least about 18-20 hours post fertilization when cultured at a standard temperature of about 28° C.

7. The method of claim 1, wherein the zebrafish embryo is aged at least about 24 hours post fertilization when cultured at a standard temperature of about 28° C.

8. The method of claim 1, wherein the zebrafish embryo is aged at least about 24-28 hours post fertilization when cultured at a standard temperature of about 28° C.

9. The method of claim 1, wherein the zebrafish embryo is aged at least about 30 hours post fertilization when cultured at a standard temperature of about 28° C.

10. The method of claim 1, wherein the zebrafish embryo is aged at least about 2 days post fertilization when cultured at a standard temperature of about 28° C.

11. The method of claim 1, wherein the zebrafish embryo is cultured at about 28° C.

12. The method of claim 1, wherein the zebrafish embryo is cultured at a higher temperature than the standard temperature.

13. The method of claim 1, wherein the zebrafish embryo is cultured at a lower temperature than the standard temperature.

14. The method of claim 1, wherein the agent is administered to the zebrafish embryo by dissolving the agent in the media containing the zebrafish embryo.

15. The method of claim 1, wherein the agent is a small molecule.

16. The method of claim 1, wherein the agent is a nucleic acid, peptide, protein, glycoprotein, carbohydrate, lipid, or glycolipid.

17. The method of claim 1, wherein the zebrafish embryo is a wild-type strain.

18. The method of claim 1, wherein the zebrafish of step (d) did not develop from the zebrafish embryo administered the agent in step (a).

* * * * *